(12) United States Patent
Wendt et al.

(10) Patent No.: US 8,377,884 B2
(45) Date of Patent: Feb. 19, 2013

(54) VARIANTS OF C-TYPE NATRIURETIC PEPTIDES

(75) Inventors: Daniel J. Wendt, Walnut Creek, CA (US); Mika Aoyagi-Scharber, Mill Valley, CA (US); Sean Bell, San Rafael, CA (US); Dong Wei, San Francisco, CA (US); Joshua R. Bliesath, Escondido, CA (US); Emil D. Kakkis, Novato, CA (US)

(73) Assignee: Biomarin Pharmaceutical Inc., Novato, CA (US)

( * ) Notice: Subject to any disclaimer, the term of this patent is extended or adjusted under 35 U.S.C. 154(b) by 0 days.

(21) Appl. No.: 12/744,079

(22) PCT Filed: Nov. 21, 2008

(86) PCT No.: PCT/US2008/084270
§ 371 (c)(1),
(2), (4) Date: Aug. 23, 2010

(87) PCT Pub. No.: WO2009/067639
PCT Pub. Date: May 28, 2009

(65) Prior Publication Data
US 2010/0331256 A1 Dec. 30, 2010

Related U.S. Application Data

(60) Provisional application No. 60/989,497, filed on Nov. 21, 2007, provisional application No. 61/061,488, filed on Jun. 13, 2008.

(51) Int. Cl.
*A61K 38/00* (2006.01)
*A61K 38/16* (2006.01)
*A61K 38/10* (2006.01)

(52) U.S. Cl. ..................... 514/16.7; 514/21.3; 514/21.4; 530/324; 530/300

(58) Field of Classification Search ........................ None
See application file for complete search history.

(56) References Cited

U.S. PATENT DOCUMENTS

| | | | |
|---|---|---|---|
| 5,252,714 A | 10/1993 | Harris et al. | |
| 5,352,770 A * | 10/1994 | Matsuo | 530/326 |
| 5,434,133 A | 7/1995 | Tanaka et al. | |
| 5,583,108 A * | 12/1996 | Wei et al. | 514/9.7 |
| 5,665,704 A * | 9/1997 | Lowe et al. | 514/9.7 |
| 5,846,932 A | 12/1998 | Lowe et al. | |
| 6,020,168 A | 2/2000 | Matsuo et al. | |
| 6,034,231 A | 3/2000 | Tanaka et al. | |
| 6,136,040 A | 10/2000 | Ornitz et al. | |
| 6,265,632 B1 | 7/2001 | Yayon et al. | |
| 6,407,211 B1 * | 6/2002 | Burnett et al. | 530/350 |
| 6,743,425 B2 | 6/2004 | Nakao | |
| 7,256,253 B2 * | 8/2007 | Bridon et al. | 530/300 |
| 7,276,481 B2 | 10/2007 | Golembo et al. | |
| 7,648,962 B2 * | 1/2010 | James et al. | 514/1.1 |
| 2011/0269684 A1 * | 11/2011 | Burnett et al. | 514/12.4 |
| 2012/0164142 A1 * | 6/2012 | Crine et al. | 424/134.1 |

FOREIGN PATENT DOCUMENTS

| | | |
|---|---|---|
| EP | 0466174 A1 | 1/1992 |
| EP | 0497368 A1 | 8/1992 |
| EP | 1743653 A1 | 1/2007 |
| WO | WO-94/20534 A1 | 9/1994 |
| WO | WO-00/61631 | 10/2000 |
| WO | WO-02/074234 A2 | 9/2002 |
| WO | WO-2004/047871 A2 | 6/2004 |

OTHER PUBLICATIONS

Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
Yasuda et al 2010. Endocrine J. 57:659-666.*
Agoston et al., C-type natriuretic peptide regulates endochondral bone growth through p38 MAP kinase-dependent and -independent pathways, *BMC Dev. Biol.*, 7:18 (2007).
Aigner et al., Apoptosis and cellular vitality: issues in osteoarthritic cartilage degeneration, *Arthritis Rheum.*, 46:1986-96 (2002).
Alfonzo et al., Characterization of a G protein-coupled guanylyl cyclase-B receptor from bovine tracheal smooth muscle, *J. Recept. Signal Transduct. Res.*, 26:269-97 (2006).
Anand-Srivastava et al., Cytoplasmic domain of natriuretic peptide receptor-C inhibits adenylyl cyclase. Involvement of a pertussis toxin-sensitive G protein, *J. Biol. Chem.*, 271:19324-9 (1996).
Bartels et al., Mutations in the transmembrane natriuretic peptide receptor NPR-B impair skeletal growth and cause acromesomelic dysplasia, type Maroteaux, *Am. J. Hum. Genet.*, 75:27-34 (2004).
Barton et al., Endothelium-independent relaxation and hyperpolarization to C-type natriuretic peptide in porcine coronary arteries, *J. Cardiovasc. Pharmacol.*, 31:377-83 (1998).
Bellus et al., Hypochondroplasia: molecular analysis of the fibroblast growth factor receptor 3 gene, *Ann. NY Acad. Sci.*, 785:182-7 (1996).
Bennett et al., Extracellular domain-IgG fusion proteins for three human natriuretic peptide receptors. Hormone pharmacology and application to solid phase screening of synthetic peptide antisera, *J. Biol. Chem.*, 266:23060-7 (1991).

(Continued)

*Primary Examiner* — Shulamith H Shafer
(74) *Attorney, Agent, or Firm* — Marshall, Gerstein & Borun LLP

(57) ABSTRACT

The present invention provides variants of C-type natriuretic peptide (CNP) comprising one or more deletions; additions of and/or substitutions with natural amino acids, unnatural amino acids and/or peptidomimetics (including peptide bond isosteres); amino acid extensions; and/or other chemical moieties such as, e.g., poly(ethylene glycol) and hydrophobic acids. The CNP variants are useful as therapeutic agents for the treatment of diseases responsive to CNP, including but not limited to bone-related disorders such as, e.g., skeletal dysplasias and achondroplasia, and vascular smooth muscle disorders such as, e.g., restenosis and arteriosclerosis.

24 Claims, 6 Drawing Sheets

OTHER PUBLICATIONS

Brandt et al., Neutral endopeptidase regulates C-type natriuretic peptide metabolism but does not potentiate its bioactivity in vivo, *Hypertension*, 30:184-90 (1997).

Caliceti et al., Pharmacokinetic and biodistrilbution properties of poly(ethylene glycol)-protein conjugates, *Adv. Drug Deliv. Rev.*, 55:1261-77 (2003).

Chauhan et al., Release of C-type natriuretic peptide accounts for the biological activity of endothelium-derived hyperpolarizing factor, *Proc. Natl. Acad. Sci. USA*, 100:1426-31 (2003).

Chen et al., C-type natriuretic peptide: the endothelial component of the natriuretic peptide system, *J. Cardiovasc. Pharmacol.*, Suppl 3:S22-8 (1998).

Chusho et al., Dwarfism and early death in mice lacking C-type natriuretic peptide, *Proc. Natl. Acad. Sci. USA*, 98:4016-21 (2001).

Coffin et al., Abnormal bone growth and selective translational regulation in basic fibroblast growth factor (FGF-2) transgenic mice, *Mol. Biol. Cell*, 6:1861-73 (1995).

Colvin et al., Skeletal overgrowth and deafness in mice lacking fibroblast growth factor receptor 3, *Nat. Genet.*, 12:390-7 (1996).

Cunningham et al., Production of an atrial natriuretic peptide variant that is specific for type A receptor, *EMBO J.*, 13:2508-15 (1994).

Davis, Biochemistry. Mimicking posttranslational modifications of proteins, *Science*, 303:480-2 (2004).

Furuya et al., Structural requirements of C-type natriuretic peptide for elevation of cyclic GMP in cultured vascular smooth muscle cells, *Biochem. Biophys. Res. Commun.*, 183:964-9 (1992).

Furuya et al., C-Type natriuretic peptide is a growth inhibitor of rat vascular smooth muscle cells, *Biochem. Biophys. Res. Commun.*, 177:927-31 (1991).

Gardner et al., Molecular biology of the natriuretic peptide system: implications for physiology and hypertension, *Hypertension*, 49:419-26 (2007).

Genbank Accession No. NP_002512, natriuretic peptides B preproprotein [*Homo sapiens*], dated Jul. 18, 2010.

Genbank Accession No. NP_006163, atrial natriuretic factor preproprotein [*Homo sapiens*], dated Jul. 18, 2010.

Genbank Accession No. NP_077720, C-type natriuretic peptide precursor [*Homo sapiens*], dated Jul. 18, 2010.

Hama et al., Detection of C-type natriuretic peptide in human circulation and marked increase of plasma CNP level in septic shock patients, *Biochem., Biophys. Res. Commun.*, 198:1177-82 (1994).

He et al., Allosteric activation of a spring-loaded natriuretic peptide receptor dimer by hormone, *Science*, 293:1657-62 (2001).

He et al., Structural determinants of natriuretic peptide receptor specificity and degeneracy, *J. Mol. Biol.*, 361:698-714 (2006).

Hofmann et al., Recent advances in the application of expressed protein ligation to protein engineering, *Curr. Opin. Biotechnol.*, 13:297-303 (2002).

Horio et al., Gene expression, secretion, and autocrine action of C-type natriuretic peptide in cultured adult rat cardiac fibroblasts, *Endocrinology*, 144:2279-84 (2003).

Horton et al., Standard growth curves for achondroplasia, *J. Pediatr.*, 93:435-8 (1978).

Hunt et al., Bioactivity and metabolism of C-type natriuretic peptide in normal man, *J. Clin. Endocrinol. Metab.*, 78:1428-35 (1994).

Igaki et al., Effects of intravenously administered C-type natriuretic peptide in humans: comparison with atrial natriuretic peptide, *Hypertens. Res.*, 21:7-13 (1998).

International Preliminary Report on Patentability for corresponding International Application No. PCT/US08/84270, dated May 25, 2010.

International Search Report and Written Opinion for corresponding International Application No. PCT/US2008/084270, dated May 28, 2009.

Itoh et al., C-type natriuretic peptide ameliorates monocrotaline-induced pulmonary hypertension in rats, *Am. J. Respir. Crit. Care Med.*, 170:1204-11 (2004).

Jin et al., Novel analog of atrial natriuretic peptide selective for receptor-A produces increased diuresis and natriuresis in rats, *J. Clin. Invest.*, 98:969-76 (1996).

Kenny et al., Hydrolysis of human arid pig brain natriuretic peptides, urodilatin, C-type natriuretic peptide and some C-receptor ligands by endopeptidase-24.11, *Biochem. J.*, 291 (Pt 1):83-8 (1993).

Klinger et al., C-type natriuretic peptide expression and pulmonary vasodilation in hypoxia-adapted rats, *Am. J. Physiol.*, 275:L645-52 (1998).

Koller et al., Molecular biology of the natriuretic peptides and their receptors, *Circulation*, 86:1081-8 (1992).

Koller et al., Selective activation of the B natriuretic peptide receptor by C-type natriuretic peptide (CNP), *Science*, 252:120-3 (1991).

Krejci et al., Interaction of fibroblast growth factor andl C-natriuretic peptide signaling in regulation of chondrocyte proliferation and extracellular matrix homeostasis, *J. Cell Sci.*, 118:5089-100 (2005).

Levin et al., Natriuretic peptides, *N. Engl. J. Med.*, 339:321-8 (1998).

Maack, Role of atrial natriuretic factor in volume control, *Kidney Int.*, 49:1732-7 (1996).

Maack et al., Physiological role of silent receptors of atrial natriuretic factor, *Science*, 238:675-8 (1987).

Matsukawa et al., The natriuretic peptide clearance receptor locally modulates the physiological effects of the natriuretic peptide system, *Proc. Natl. Acad. Sci. USA*, 96:7403-8 (1999).

Melo et al., Chronic regulation of arterial blood pressure by ANP: role of endogenous vasoactive endothelial factors, *Am. J. Physiol.*, 275:H1826-33 (1998).

Murthy et al., Identification of the G protein-activating domain of the natriuretic peptide clearance receptor (NPR-C), *J. Biol. Chem.*, 274:17587-92 (1999).

Murthy et al., Gi-1/Gi-2-dependent signaling by single-transmembrane natriuretic peptide clearance receptor, *Am. J. Physiol. Gastrointest. Liver Physiol.*, 278:G974-80 (2000).

Nakao et al., Molecular biology and biochemistry of the natriuretic peptide system. I: Natriuretic peptides, *J. Hypertens.*, 10:907-12 (1992).

Nakao et al., Molecular biology and biochemistry of the natriuretic peptide system. II: Natriuretic peptide receptors, *J. Hypertens.*, 10:111-4 (1992).

Naski et al., Repression of hedgehog signaling and BMP4 expression in growth plate cartilage by fibroblast growth factor receptor 3, *Development*, 125:4977-88 (1998).

Oefner et al., Structure of human neutral endopeptidase (Neprilysin) complexed with phosphoramidon, *J. Mol. Biol.*, 296:341-9 (2000).

Ogawa et al., Crystal structure of hormone-bound atrial natriuretic peptide receptor extracellular domain: rotation mechanism for transmembrane signal transduction, *J. Biol. Chem.*, 279:28625-31 (2004).

Ohbayashi et al., Neutral endopeptidase 3.4.24.11 inhibition potentiates the inhibitory effects of type-C natriuretic peptide on leukotriene D4-induced airway changes, *Clin. Exp. Pharm. Physiol.*, 25:986-91 (1997).

Okahara et al., Shear stress induces expression of CNP gene in human endothelial cells, *FEBS Lett.*, 373:108-10 (1995).

Olney et al., Heterozygous mutations in natriuretic peptide receptor-B (NPR2) are associated with short stature, *J. Clin. Endocrinol. Metab.*, 91:1229-32 (2006).

Olney, C-type natriuretic peptide in growth: a new paradigm, *Growth Horm. IGF Res.*, 16 Suppl A:S6-14 (2006).

Pagano et al., Cytoplasmic domain of natriuretic peptide receptor C constitutes Gi activator sequences that inhibit adenylyl cyclase activity, *J. Biol. Chem.*, 276:22064-70 (2001).

Perlman et al., Glycosylation of an N-terminal extension prolongs the half-life and increases the in vivo activity of follicle stimulating hormone, *J. Clin. Endocrinol. Metab.*, 88:3227-35 (2003).

Pitkin et al., Charge and lipophilicity govern the pharmacokinetics of glycopeptide antibiotics, *Antimicrob. Agents Chemother.*, 29:440-4 (1986).

Qian et al., Local expression of C-type natriuretic peptide suppresses inflammation, eliminates shear stress-induced thrombosis, and prevents neointima formation through enhanced nitric oxide production in rabbit injured carotid arteries, *Circ. Res.*, 91:1063-9 (2002).

Rose et al., Natriuretic peptide C receptor signalling in the heart and vasculature, *J. Physiol.*, 586:353-66 (2008).

Rousseau et al., Missense FGFR3 mutations create cysteine residues in thanatophoric dwarfism type I (TD1), *Hum. Mol. Genet.*, 5:509-12 (1996).

Rousseau et al., Mutations in the gene encoding fibroblast growth factor receptor-3 in achondroplasia, *Nature*, 371:252-4 (1994).

Sato et al., Therapeutic peptides: technological advances driving peptides into development, *Curr. Opin. Biotechnol.*, 17:638-42 (2006).

Schiller et al., Synthesis and activity profiles of atrial natriuretic peptide (ANP) analogs with reduced ring size, *Biochem. Biophys. Res. Commun.*, 138:880-6 (1986).

Shiang et al., Mutations in the transmembrane domain of FGFR3 cause the most common genetic form of dwarfism, achondroplasia, *Cell*, 78:335-42 (1994).

Sudoh et al., C-type natriuretic peptide (CNP): a new member of natriuretic peptide family identified in porcine brain, *Biochem. Biophys. Res. Commun.*, 168:863-70 (1990).

Suga et al., Receptor selectivity of natriuretic peptide family, atrial natriuretic peptide, brain natriuretic peptide, and C-type natriuretic peptide, *Endocrinology*, 130:229-39 (1992).

Tamura et al., Critical roles of the guanylyl cyclase B receptor in endochondral ossification and development of female reproductive organs, *Proc. Natl. Acad. Sci. USA*, 101:17300-5 (2004).

Tavormina et al., Thanatophoric dysplasia (types I and II) caused by distinct mutations in fibroblast growth factor receptor 3, *Nat. Genet.*, 9:321-8 (1995).

Vehaskari et al., Glomerular charge and urinary protein excretion: effects of systemic and intrarenal polycation infusion in the rat, *Kidney Int.*, 22:127-35 (1982).

Wang et al., A mouse model for achondroplasia produced by targeting fibroblast growth factor receptor 3, *Proc. Natl. Acad. Sci. USA*, 96:4455-60 (1999).

Wang et al., Bone-targeting macromolecular therapeutics, *Adv. Drug Deliv. Rev.*, 57:1049-76 (2005).

Wei et al., Vascular actions of C-type natriuretic peptide in isolated porcine coronary arteries and coronary vascular smooth muscle cells, *Biochem. Biophys. Res. Commun.*, 205:765-71 (1994).

Werle et al., Strategies to improve plasma half life time of peptide and protein drugs, *Amino Acids*, 30:351-67 (2006).

Wilkie et al., Functions of fibroblast growth factors and their receptors, *Curr. Biol.*, 5:500-7 (1995).

Wu et al., Furin-mediated processing of Pro-C-type natriuretic peptide, *J. Biol. Chem.*, 278:25847-52 (2003).

Yamashita et al., Concentration of mRNA for the natriuretic peptide receptor-C in hypertrophic chondrocytes of the fetal mouse tibia, *J. Biochem.*, 127:177-9 (2000).

Yasoda et al., Overexpression of CNP in chondrocytes rescues achondroplasia through a MAPK-dependent pathway, *Nat. Med.*, 10:80-6 (2004).

Yeung et al., Binding of CNP-22 and CNP-53 to cultured mouse astrocytes and effects on cyclic GMP, *Peptides*, 17:101-6 (1996).

\* cited by examiner

Bars from left to right:

| 1 | control (no CNP, no FGF2) |
|---|---|
| 2 | CNP (0.2 uM) continuous |
| 3 | CNP (0.2 uM) 1 hr once daily |
| 4 | CNP (0.2 uM) 2 hr once daily |
| 5 | FGF2 (5 ng/mL) continuous |
| 6 | FGF2 + CNP (0.2 uM) continuous |
| 7 | FGF2 + CNP (0.2 uM) 1 hr daily |
| 8 | FGF2 + CNP (0.2 uM) 2 hr daily |

SEQUENCE LISTING

```
<160> NUMBER OF SEQ ID NOS: 144

<210> SEQ ID NO 1
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: wtCNP-22
<220> FEATURE:
<221> NAME/KEY: DISULFID
<222> LOCATION: (6)..(22)
<223> OTHER INFORMATION: Cysteines in positions 6 and 22 form cyclic
      domain via disulfide bond

<400> SEQUENCE: 1

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 2
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CNP-17

<400> SEQUENCE: 2

Cys Phe Gly Leu Lys Leu Asp Arg Ile Gly Ser Met Ser Gly Leu Gly
1               5                   10                  15

Cys
```

```
<210> SEQ ID NO 3
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CNP-27

<400> SEQUENCE: 3

Gly Ala Asn Lys Lys Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 4
<211> LENGTH: 53
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CNP-53

<400> SEQUENCE: 4

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
    50

<210> SEQ ID NO 5
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Gly is optionally modified with an amino acid
      sequence derived from a natriuretic polypeptide, a non-natriuretic
      polypeptide
<220> FEATURE:
<221> NAME/KEY: MOD_RES
<222> LOCATION: (22)..(22)
<223> OTHER INFORMATION: Cys is optionally modified with an amino acid
      sequence derived from a natriuretic polypeptide, a non-natriuretic
      polypeptide

<400> SEQUENCE: 5

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 6
<211> LENGTH: 22
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MISC_FEATURE
<222> LOCATION: (1)..(1)
<223> OTHER INFORMATION: N-terminus is modified with a synthetic or
      natural polymeric group or combination thereof
<220> FEATURE:
<221> NAME/KEY: MOD_RES
<222> LOCATION: (4)..(4)
<223> OTHER INFORMATION: Xaa is Lys or a conservative amino acid
      substitution thereof, any natural or unnatural amino acid or any
      amino acid that does not have a reactive primary amine on a side
      chain, Arg, Gly, 6-hydroxy-norleucine, citrulline (Cit), Gln, Glu
      or Ser
<220> FEATURE:
<221> NAME/KEY: MOD_RES
<222> LOCATION: (10)..(10)
<223> OTHER INFORMATION: Xaa is Lys or a conservative amino acid
      substitution thereof, any natural or unnatural amino acid or any
      amino acid that does not have a reactive primary amine on a side
      chain, Arg, Gly, 6-hydroxy-norleucine, citrulline (Cit), Gln, Glu
      or Ser
<220> FEATURE:
<221> NAME/KEY: MISC_FEATURE
<222> LOCATION: (22)..(22)
<223> OTHER INFORMATION: C-terminus is optionally modified with a
      synthetic or natural polymeric group or combination thereof

<400> SEQUENCE: 6

Gly Leu Ser Xaa Gly Cys Phe Gly Leu Xaa Leu Asp Arg Ile Gly Ser
1               5                   10                  15

Met Ser Gly Leu Gly Cys
            20

<210> SEQ ID NO 7
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 7

Gly Ala Asn Lys Lys
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 8

Gly Ala Asn Arg Arg
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 9

Gly Ala Asn Pro Arg
1               5

<210> SEQ ID NO 10
<211> LENGTH: 5
<212> TYPE: PRT
<213> ORGANISM: Artificial Sequence
```

```
<220> FEATURE:
<223> OTHER INFORMATION: Synthetic Polypeptide

<400> SEQUENCE: 10

Gly Ala Asn Gln Gln
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 11

Gly Ala Asn Ser Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 12

Gly Ala Asn Arg Gln
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 13

Gly Ala Asn Arg Met
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 14

Gly Ala Asn Arg Thr
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 15

Gly Ala Asn Arg Ser
1               5

<210> SEQ ID NO 16
<211> LENGTH: 13
<212> TYPE: PRT
<213> ORGANISM: Artificial Sequence
<220> FEATURE:
<223> OTHER INFORMATION: Synthetic Polypeptide
```

```
<400> SEQUENCE: 16

Ala Ala Trp Ala Arg Leu Leu Gln Glu His Pro Asn Ala
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 17

Ala Ala Trp Ala Arg Leu Leu Gln Glu His Pro Asn Ala Arg
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 18

Asp Leu Arg Val Asp Thr Lys Ser Arg Ala Ala Trp Ala Arg
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 19

Gln Glu His Pro Asn Ala Arg Lys Tyr Lys Gly Ala Asn Lys Lys
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 20

Gln Glu His Pro Asn Ala Arg Lys Tyr Lys Gly Ala Asn Arg Arg
1               5                   10                  15

<210> SEQ ID NO 21
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 21

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys
                20                  25                  30

<210> SEQ ID NO 22
<211> LENGTH: 31
<212> TYPE: PRT
<213> ORGANISM: Artificial Sequence
<220> FEATURE:
```

<223> OTHER INFORMATION: Synthetic Polypeptide

<400> SEQUENCE: 22

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Arg Arg
            20                  25                  30

<210> SEQ ID NO 23
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 23

Ser Leu Arg Arg Ser Ser
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 24

Asn Ser Phe Arg Tyr
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 25

Ser Pro Lys Met Val Gln Gly Ser Gly
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 26

Met Val Gln Gly Ser Gly
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 27

Lys Val Leu Arg Arg Tyr
1               5

<210> SEQ ID NO 28
<211> LENGTH: 6
<212> TYPE: PRT
<213> ORGANISM: Artificial Sequence

```
<220> FEATURE:
<223> OTHER INFORMATION: Synthetic Polypeptide

<400> SEQUENCE: 28

Lys Val Leu Arg Arg His
1               5

<210> SEQ ID NO 29
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 29

Gly Gln His Lys Asp Asp Asn Pro Asn Leu Pro Arg
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 30

Gly Val Pro Gln Val Ser Thr Ser Thr
1               5

<210> SEQ ID NO 31
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 31

Gly Glu Arg Ala Phe Lys Ala Trp Ala Val Ala Arg Leu Ser Gln
1               5                   10                  15

<210> SEQ ID NO 32
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 32

Gly Gln Pro Arg Glu Pro Gln Val Tyr Thr Leu Pro Pro Ser
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Amino acid extention

<400> SEQUENCE: 33

Gln Glu His Pro Asn Ala Arg Lys Tyr Lys Gly Ala Asn Lys Lys
1               5                   10                  15

<210> SEQ ID NO 34
<211> LENGTH: 37
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CNP-22 with amino acid extention
<220> FEATURE:
<221> NAME/KEY: MISC_FEATURE
<222> LOCATION: (19)..(19)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Glu or Ser
<220> FEATURE:
<221> NAME/KEY: MISC_FEATURE
<222> LOCATION: (25)..(25)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Glu or Ser
<220> FEATURE:
<221> NAME/KEY: MISC_FEATURE
<222> LOCATION: (37)..(37)
<223> OTHER INFORMATION: C-terminus is optionally modified with a
      synthetic, natural or combination polymeric group

<400> SEQUENCE: 34

Gln Glu His Pro Asn Ala Arg Lys Tyr Lys Gly Ala Asn Lys Lys Gly
1               5                   10                  15

Leu Ser Xaa Gly Cys Phe Gly Leu Xaa Leu Asp Arg Ile Gly Ser Met
            20                  25                  30

Ser Gly Leu Gly Cys
        35

<210> SEQ ID NO 35
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CNP22 (K4R)

<400> SEQUENCE: 35

Gly Leu Ser Arg Gly Cys Phe Gly Leu Lys Leu Asp Arg Ile Gly Ser
1               5                   10                  15

Met Ser Gly Leu Gly Cys
            20

<210> SEQ ID NO 36
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: GANRR-CNP22(K4R) - CNP27(Arg4)

<400> SEQUENCE: 36

Gly Ala Asn Arg Arg Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 37
<211> LENGTH: 27
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MISC_FEATURE
<223> OTHER INFORMATION: GANPR-CNP22(K4R) - CNP27(Pro4) - Analog CI

<400> SEQUENCE: 37

Gly Ala Asn Pro Arg Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 38
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: ER-CNP22

<400> SEQUENCE: 38

Glu Arg Gly Leu Ser Lys Gly Cys Phe Gly Leu Lys Leu Asp Arg Ile
1               5                   10                  15

Gly Ser Met Ser Gly Leu Gly Cys
            20

<210> SEQ ID NO 39
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BA - ER-CNP22(K4R)

<400> SEQUENCE: 39

Glu Arg Gly Leu Ser Arg Gly Cys Phe Gly Leu Lys Leu Asp Arg Ile
1               5                   10                  15

Gly Ser Met Ser Gly Leu Gly Cys
            20

<210> SEQ ID NO 40
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: R-CNP22

<400> SEQUENCE: 40

Arg Gly Leu Ser Lys Gly Cys Phe Gly Leu Lys Leu Asp Arg Ile Gly
1               5                   10                  15

Ser Met Ser Gly Leu Gly Cys
            20

<210> SEQ ID NO 41
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AZ - R-CNP22(K4R)
```

```
-continued

<400> SEQUENCE: 41

Arg Gly Leu Ser Arg Gly Cys Phe Gly Leu Lys Leu Asp Arg Ile Gly
1               5                   10                  15

Ser Met Ser Gly Leu Gly Cys
            20

<210> SEQ ID NO 42
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CNP22 (K4R)(K10R)

<400> SEQUENCE: 42

Gly Leu Ser Arg Gly Cys Phe Gly Leu Arg Leu Asp Arg Ile Gly Ser
1               5                   10                  15

Met Ser Gly Leu Gly Cys
            20

<210> SEQ ID NO 43
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CNP-22 (Cys6-Phe7 variable bond)
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -CH2-NH-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -C(=O)-N(R)- where R is methyl, ethyl, n-propyl, isopropyl,
      cyclopropyl, n-butyl, isobutyl, sec-butyl or tert-butyl
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -C(=O)-NH-CH2-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -CH2-S-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -CH2-S(O)n where n is 1 or 2
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -CH2-CH2-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -CH=CH-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -C(=O)-CH2-
<220> FEATURE:
<221> NAME/KEY: MOD_RES
```

```
<222> LOCATION: (6)..(7)
<223> OTHER INFORMATION: Cys6-Phe7 peptide bond (-C(=O)-NH-) replaced
      with -CH(CN)-NH-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -CH(OH)-CH2-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -O-C(=O)-NH-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with NHC(=O)NH-

<400> SEQUENCE: 43

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 44
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (7)..(7)
<223> OTHER INFORMATION: Xaa is 3-amino-2-phenylpropionic acid or D-Phe

<400> SEQUENCE: 44

Gly Leu Ser Lys Gly Cys Xaa Gly Leu Lys Leu Asp Arg Ile Gly Ser
1               5                   10                  15

Met Ser Gly Leu Gly Cys
            20

<210> SEQ ID NO 45
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CNP22 - modified Cys6
<220> FEATURE:
<221> NAME/KEY: MOD_RES
<222> LOCATION: (6)..(6)
<223> OTHER INFORMATION: Xaa is Cys, homocysteine, penicillamine,
      2-mercaptopropionic acid, or 3-mercaptopropionic acid.

<400> SEQUENCE: 45

Gly Leu Ser Lys Gly Xaa Phe Gly Leu Lys Leu Asp Arg Ile Gly Ser
1               5                   10                  15

Met Ser Gly Leu Gly Cys
            20

<210> SEQ ID NO 46
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
```

```
<222> LOCATION: (1)..(1)
<223> OTHER INFORMATION: N-terminus is optionally modified with a bone
      or cartilage targeting compound, a biphosphonate, polyAsp,
      polyGlu, osteopontin, osteocalcin, or sialoprotein peptides,
      polymers, PEG, carbohydrates, hydrophobic acids, or amino acids
<220> FEATURE:
<221> NAME/KEY: MOD_RES
<222> LOCATION: (4)..(4)
<223> OTHER INFORMATION: Xaa is Lys or a conservative amino acid
      substitution thereof, any natural or unnatural amino acid or any
      amino acid that does not have a reactive primary amine on a side
      chain, Arg, Gly, 6-hydroxy-norleucine, citrulline (Cit), Gln, Ser,
      or Glu
<220> FEATURE:
<221> NAME/KEY: MISC_FEATURE
<222> LOCATION: (6)..(7)
<223> OTHER INFORMATION: Cys6-Phe7 peptide bond may be replaced with
      peptide bond isosteres
<220> FEATURE:
<221> NAME/KEY: MOD_RES
<222> LOCATION: (7)..(7)
<223> OTHER INFORMATION: Xaa is L-Phe, D-Phe, 3-amino-2-phenylpropionic
      acid, or N-alkylated derivatives of Phe
<220> FEATURE:
<221> NAME/KEY: MOD_RES
<222> LOCATION: (8)..(8)
<223> OTHER INFORMATION: Xaa is Gly, tert-butyl-Gly (tBu-Gly), Thr, Ser,
      Val or Asn
<220> FEATURE:
<221> NAME/KEY: MOD_RES
<222> LOCATION: (9)..(9)
<223> OTHER INFORMATION: Xaa is Leu, Ser, or Thr
<220> FEATURE:
<221> NAME/KEY: MISC_FEATURE
<222> LOCATION: (9)..(10)
<223> OTHER INFORMATION: Peptide bond between positions 9 and 10 may be
      replaced with peptide bond isosteres
<220> FEATURE:
<221> NAME/KEY: MOD_RES
<222> LOCATION: (10)..(10)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Ser or Glu
<220> FEATURE:
<221> NAME/KEY: MISC_FEATURE
<222> LOCATION: (11)..(12)
<223> OTHER INFORMATION: Leu11 and Asp12 peptide bond may be replaced
      with peptide bond isosteres
<220> FEATURE:
<221> NAME/KEY: MOD_RES
<222> LOCATION: (14)..(14)
<223> OTHER INFORMATION: Xaa is Ile, or tBu-Gly
<220> FEATURE:
<221> NAME/KEY: MISC_FEATURE
<222> LOCATION: (14)..(15)
<223> OTHER INFORMATION: Peptide bond between position 14 and Gly15 may
      be replaced with peptide bond isosteres
<220> FEATURE:
<221> NAME/KEY: MOD_RES
<222> LOCATION: (17)..(17)
<223> OTHER INFORMATION: Xaa is Met, Val, Asn, beta-Cl-Ala,
      2-aminobutyric acid (Abu) or 2-amino-isobutyric acid (Aib)
<220> FEATURE:
<221> NAME/KEY: MOD_RES
<222> LOCATION: (20)..(20)
<223> OTHER INFORMATION: Xaa is Leu, norleucine (Nle), homoleucine
      (Hleu), Val, tert-butyl-Ala (tBu-Ala), Ser, Thr, or Arg
<220> FEATURE:
<221> NAME/KEY: MISC_FEATURE
<222> LOCATION: (20)..(21)
<223> OTHER INFORMATION: Peptide bond between position 20 and Gly21 may
      be replaced with peptide bond isosteres
<220> FEATURE:
<221> NAME/KEY: MISC_FEATURE
<222> LOCATION: (22)..(22)
<223> OTHER INFORMATION: C-terminus is optionally modified with a bone
      or cartilage targeting compound, a bisphosphonate, polyAsp,
      polyGlu, osteopontin, osteocalcin or sialoprotein peptides, or
      amino acid sequences derived from non-CNP polypeptides
```

-continued

```
<400> SEQUENCE: 46

Gly Leu Ser Xaa Gly Cys Xaa Xaa Xaa Xaa Leu Asp Arg Xaa Gly Ser
1               5                   10                  15

Xaa Ser Gly Xaa Gly Cys
            20

<210> SEQ ID NO 47
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N-terminus is optionally modified with a
      peptide sequence containing one to five amino acids from a
      natriuretic or non-natriuretic polypeptide
<220> FEATURE:
<221> NAME/KEY: MOD_RES
<222> LOCATION: (4)..(4)
<223> OTHER INFORMATION: Xaa is Lys or a conservative amino acid
      substitution thereof, any natural or unnatural amino acid or any
      amino acid that does not have a reactive primary amine on a side
      chain, Arg, 6-hydroxy-norleucine, citrulline (Cit), Gln, Ser, or
      Glu
<220> FEATURE:
<221> NAME/KEY: MOD_RES
<222> LOCATION: (6)..(6)
<223> OTHER INFORMATION: Xaa is Cys or decarboxy Cys
<220> FEATURE:
<221> NAME/KEY: MISC_FEATURE
<222> LOCATION: (6)..(7)
<223> OTHER INFORMATION: Peptide bond between positions 6 and 7 may be
      replaced with -CH2-NH-
<220> FEATURE:
<221> NAME/KEY: MISC_FEATURE
<222> LOCATION: (6)..(7)
<223> OTHER INFORMATION: Peptide bond between positions 6 and 7 may be
      replaced with -C(=O)-N(R)- where R is methyl, ethyl, n-propyl,
      isopropyl, cyclopropyl, n-butyl, isobutyl, sec-butyl or tert-butyl
<220> FEATURE:
<221> NAME/KEY: MISC_FEATURE
<222> LOCATION: (6)..(7)
<223> OTHER INFORMATION: Peptide bond between positions 6 and 7 may be
      replaced with -C(=O)-NH-CH2-
<220> FEATURE:
<221> NAME/KEY: MISC_FEATURE
<222> LOCATION: (6)..(7)
<223> OTHER INFORMATION: Peptide bond between positions 6 and 7 may be
      replaced with -CH2-S-
<220> FEATURE:
<221> NAME/KEY: MISC_FEATURE
<222> LOCATION: (6)..(7)
<223> OTHER INFORMATION: Peptide bond between positions 6 and 7 may be
      replaced with -CH2-S(O)n where n is 1 or 2
<220> FEATURE:
<221> NAME/KEY: MISC_FEATURE
<222> LOCATION: (6)..(7)
<223> OTHER INFORMATION: Peptide bond between positions 6 and 7 may be
      replaced with -CH2-CH2-
<220> FEATURE:
<221> NAME/KEY: MISC_FEATURE
<222> LOCATION: (6)..(7)
<223> OTHER INFORMATION: Peptide bond between positions 6 and 7 may be
      replaced with -CH=CH-
<220> FEATURE:
<221> NAME/KEY: MISC_FEATURE
<222> LOCATION: (6)..(7)
<223> OTHER INFORMATION: Peptide bond between positions 6 and 7 may be
      replaced with -C(=O)-CH2-
<220> FEATURE:
<221> NAME/KEY: MISC_FEATURE
<222> LOCATION: (6)..(7)
<223> OTHER INFORMATION: Peptide bond between positions 6 and 7 may be
      replaced with -CH(CN)-NH-
<220> FEATURE:
```

```
<221> NAME/KEY: MISC_FEATURE
<222> LOCATION: (6)..(7)
<223> OTHER INFORMATION: Peptide bond between positions 6 and 7 may be
      replaced with -CH(OH)-CH2-
<220> FEATURE:
<221> NAME/KEY: MISC_FEATURE
<222> LOCATION: (6)..(7)
<223> OTHER INFORMATION: Peptide bond between positions 6 and 7 may be
      replaced with -O-C(=O)-NH-
<220> FEATURE:
<221> NAME/KEY: MISC_FEATURE
<222> LOCATION: (6)..(7)
<223> OTHER INFORMATION: Peptide bond between positions 6 and 7 may be
      replaced with -NHC(=O)NH-
<220> FEATURE:
<221> NAME/KEY: MOD_RES
<222> LOCATION: (7)..(7)
<223> OTHER INFORMATION: Xaa is L-Phe, D-Phe, 3-amino-2-phenylpropionic
      acid, or N-alkylated derivatives of Phe
<220> FEATURE:
<221> NAME/KEY: MOD_RES
<222> LOCATION: (8)..(8)
<223> OTHER INFORMATION: Xaa is Gly, tert-butyl-Gly (tBu-Gly), Val, Ser,
      Thr or Asn
<220> FEATURE:
<221> NAME/KEY: MOD_RES
<222> LOCATION: (9)..(9)
<223> OTHER INFORMATION: Xaa is Leu, Ser, or Thr
<220> FEATURE:
<221> NAME/KEY: MISC_FEATURE
<222> LOCATION: (9)..(10)
<223> OTHER INFORMATION: Peptide bond between positions 9 and 10 may be
      replaced with peptide bond isosteres
<220> FEATURE:
<221> NAME/KEY: MOD_RES
<222> LOCATION: (10)..(10)
<223> OTHER INFORMATION: Xaa is Arg, Gly, 6-hydroxy-norleucine,
      citrulline (Cit), Gln, Ser or Glu
<220> FEATURE:
<221> NAME/KEY: MISC_FEATURE
<222> LOCATION: (11)..(12)
<223> OTHER INFORMATION: Leu11 and Asp12 peptide bond may be replaced
      with peptide bond isosteres
<220> FEATURE:
<221> NAME/KEY: MOD_RES
<222> LOCATION: (14)..(14)
<223> OTHER INFORMATION: Xaa is Ile, or tBu-Gly
<220> FEATURE:
<221> NAME/KEY: MISC_FEATURE
<222> LOCATION: (14)..(15)
<223> OTHER INFORMATION: Peptide bond between position 14 and Gly15 may
      be replace with peptide bond isosteres
<220> FEATURE:
<221> NAME/KEY: MOD_RES
<222> LOCATION: (17)..(17)
<223> OTHER INFORMATION: Xaa is Met, Val, Asn, beta-Cl-Ala,
      2-aminobutyric acid (Abu) or 2-amino-isobutyric acid (Aib)
<220> FEATURE:
<221> NAME/KEY: MOD_RES
<222> LOCATION: (20)..(20)
<223> OTHER INFORMATION: Xaa is Leu, norleucine (Nle), homoleucine
      (Hleu), Val, tert-butyl-Ala (tBu-Ala), Ser, Thr, or Arg
<220> FEATURE:
<221> NAME/KEY: MISC_FEATURE
<222> LOCATION: (20)..(21)
<223> OTHER INFORMATION: Peptide bond between position 20 and Gly21 may
      be replace with peptide bond isosteres
<220> FEATURE:
<221> NAME/KEY: MISC_FEATURE
<222> LOCATION: (22)..(22)
<223> OTHER INFORMATION: C-terminus is optionally modified with a
      synthetic bone targeting compound, a bisphosphonate, polyAsp,
      polyGlu, osteopontin, osteocalcin or sialoprotein peptides, or
      charged PEG molecules

<400> SEQUENCE: 47

Gly Leu Ser Xaa Gly Xaa Xaa Xaa Xaa Xaa Leu Asp Arg Xaa Gly Ser
1               5                   10                  15
```

```
Xaa Ser Gly Xaa Gly Cys
            20
```

<210> SEQ ID NO 48
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminus modified with a synthetic or natural
      polymeric group or combination thereof
<220> FEATURE:
<221> NAME/KEY: MOD_RES
<222> LOCATION: (1)..(1)
<223> OTHER INFORMATION: Xaa is absent or may be one or more amino acids
      from Gly-Leu-Ser-Lys-Gly and/or substitutions at one or more of
      these positions
<220> FEATURE:
<221> NAME/KEY: MOD_RES
<222> LOCATION: (6)..(6)
<223> OTHER INFORMATION: Xaa is Lys, a conservative amino acid
      substitution, any natural or unnatural amino acid or any amino
      acid that does not have a reactive primary amine on a side chain
<220> FEATURE:
<221> NAME/KEY: MOD_RES
<222> LOCATION: (18)..(18)
<223> OTHER INFORMATION: C-terminus is optionally modified with a
      synthetic or natural polymeric group or a combination thereof

<400> SEQUENCE: 48

```
Xaa Cys Pro Gly Leu Xaa Leu Asp Arg Ile Gly Ser Met Ser Gly Leu
1               5                   10                  15

Gly Cys
```

<210> SEQ ID NO 49
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N-terminus may be modified with a peptide
      fragment or water soluble polymer or modification is absent
<220> FEATURE:
<221> NAME/KEY: MISC_FEATURE
<222> LOCATION: (1)..(1)
<223> OTHER INFORMATION: Peptide bond between Cys2 and position 3 may be
      replaced with peptide bond isosteres
<220> FEATURE:
<221> NAME/KEY: MOD_RES
<222> LOCATION: (2)..(2)
<223> OTHER INFORMATION: Xaa is L-Phe, D-Phe, 3-amino-2-phenylpropionic
      acid or N-alkylated derivatives of Phe
<220> FEATURE:
<221> NAME/KEY: MOD_RES
<222> LOCATION: (3)..(3)
<223> OTHER INFORMATION: Xaa is Gly, tert-butyl-Gly (tBu-Gly), Val, Ser,
      Thr or Asn
<220> FEATURE:
<221> NAME/KEY: MOD_RES
<222> LOCATION: (4)..(4)
<223> OTHER INFORMATION: Xaa is Leu, Ser, Thr or N-Me-Leu
<220> FEATURE:
<221> NAME/KEY: MOD_RES
<222> LOCATION: (5)..(5)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Ser or Glu
<220> FEATURE:
<221> NAME/KEY: MISC_FEATURE
<222> LOCATION: (6)..(6)

```
<223> OTHER INFORMATION: Leu7 and Asp8 peptide bond may be replaced with
      peptide bond isosteres
<220> FEATURE:
<221> NAME/KEY: MOD_RES
<222> LOCATION: (9)..(9)
<223> OTHER INFORMATION: Xaa is Ile, or tBu-Gly
<220> FEATURE:
<221> NAME/KEY: MISC_FEATURE
<222> LOCATION: (9)..(10)
<223> OTHER INFORMATION: Peptide bond between position 9 and Gly10 may
      be replaced with peptide bond isosteres
<220> FEATURE:
<221> NAME/KEY: MOD_RES
<222> LOCATION: (12)..(12)
<223> OTHER INFORMATION: Xaa is Met, Val, Asn, beta-Cl-Ala,
      2-aminobutyric acid (Abu) or 2-amino-isobutyric acid (Aib)
<220> FEATURE:
<221> NAME/KEY: MOD_RES
<222> LOCATION: (15)..(15)
<223> OTHER INFORMATION: Xaa is Leu, norleucine (Nle), homoleucine
      (Hleu), Val, tert-butyl-Ala (tBu-Ala), Ser, Thr, Arg
<220> FEATURE:
<221> NAME/KEY: MISC_FEATURE
<222> LOCATION: (15)..(16)
<223> OTHER INFORMATION: Peptide bond between position 15 and Gly16 may
      be replace with peptide bond isosteres
<220> FEATURE:
<221> NAME/KEY: MISC_FEATURE
<222> LOCATION: (17)..(17)
<223> OTHER INFORMATION: C-terminus is optionally modified with amino
      acid sequences useful in bone/cartilage targeting, polyAsp or
      polyGlu, osteopontin, osteocalcin, sialoprotein or sequences
      derived from NPPC or non-CNP polypeptides

<400> SEQUENCE: 49

Cys Xaa Xaa Xaa Xaa Leu Asp Arg Xaa Gly Ser Xaa Ser Gly Xaa Gly
1               5                   10                  15

Cys

<210> SEQ ID NO 50
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N-terminus is optionally modified with bone
      targeting compound, moieties to reduce renal clearance, charged
      PEG molecules or hydrophilic polymers
<220> FEATURE:
<221> NAME/KEY: MOD_RES
<222> LOCATION: (4)..(4)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Ser or Glu
<220> FEATURE:
<221> NAME/KEY: MISC_FEATURE
<222> LOCATION: (6)..(7)
<223> OTHER INFORMATION: Peptide bond between Cys6 and position 7 may be
      replaced with peptide bond isosteres
<220> FEATURE:
<221> NAME/KEY: MOD_RES
<222> LOCATION: (7)..(7)
<223> OTHER INFORMATION: Xaa is L-Phe, D-Phe, 3-amino-2-phenylpropionic
      acid or N-alkylated derivatives of Phe
<220> FEATURE:
<221> NAME/KEY: MOD_RES
<222> LOCATION: (8)..(8)
<223> OTHER INFORMATION: Xaa is Gly, tert-butyl-Gly, Thr, Ser, Val or
      Asn
<220> FEATURE:
<221> NAME/KEY: MOD_RES
<222> LOCATION: (9)..(9)
<223> OTHER INFORMATION: Xaa is Leu, Ser, or Thr
<220> FEATURE:
```

```
<221> NAME/KEY: MISC_FEATURE
<222> LOCATION: (9)..(10)
<223> OTHER INFORMATION: Peptide bond between positions 9 and 10 may be
      replaced with peptide bond isosteres
<220> FEATURE:
<221> NAME/KEY: MOD_RES
<222> LOCATION: (10)..(10)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Ser or Glu
<220> FEATURE:
<221> NAME/KEY: MOD_RES
<222> LOCATION: (11)..(11)
<223> OTHER INFORMATION: Xaa is Leu, or Asn
<220> FEATURE:
<221> NAME/KEY: MISC_FEATURE
<222> LOCATION: (11)..(12)
<223> OTHER INFORMATION: Peptide bond between position 11 and Asp12 may
      be replaced with peptide bond isosteres
<220> FEATURE:
<221> NAME/KEY: MOD_RES
<222> LOCATION: (14)..(14)
<223> OTHER INFORMATION: Xaa is Ile, tert-butyl-Gly (tBu-Gly), or Asn
<220> FEATURE:
<221> NAME/KEY: MISC_FEATURE
<222> LOCATION: (14)..(15)
<223> OTHER INFORMATION: Peptide bond between positions 14 and 15 may be
      replaced with peptide bond isosteres
<220> FEATURE:
<221> NAME/KEY: MOD_RES
<222> LOCATION: (15)..(15)
<223> OTHER INFORMATION: Xaa is Gly, Arg, Ser or Asn
<220> FEATURE:
<221> NAME/KEY: MOD_RES
<222> LOCATION: (17)..(17)
<223> OTHER INFORMATION: Xaa is Met, Val, Asn, beta-Cl-Ala,
      2-aminobutyric acid (Abu) or 2-amino-isobutyric acid (Aib)
<220> FEATURE:
<221> NAME/KEY: MOD_RES
<222> LOCATION: (20)..(20)
<223> OTHER INFORMATION: Xaa is Leu, norleucine (Nle), homoleucine
      (Hleu), Val, tert-butyl-Ala (tBu-Ala), Arg, Thr, or Ser
<220> FEATURE:
<221> NAME/KEY: MISC_FEATURE
<222> LOCATION: (20)..(21)
<223> OTHER INFORMATION: Peptide bond between position 20 and Gly21 may
      be replaced with peptide bond isosteres
<220> FEATURE:
<221> NAME/KEY: MOD_RES
<222> LOCATION: (22)..(22)
<223> OTHER INFORMATION: C-terminus is optionally modified with bone
      targeting compound, moieties to reduce renal clearance, charged
      PEG molecules or hydrophilic polymers

<400> SEQUENCE: 50

Gly Leu Ser Xaa Gly Cys Xaa Xaa Xaa Xaa Xaa Asp Arg Xaa Xaa Ser
1               5                   10                  15

Xaa Ser Gly Xaa Gly Cys
            20

<210> SEQ ID NO 51
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Xaa is Arg or Glu

<400> SEQUENCE: 51

Xaa Leu Ser Lys Gly Cys Phe Gly Leu Lys Leu Asp Arg Ile Gly Ser
1               5                   10                  15

Met Ser Gly Leu Gly Cys
```

<210> SEQ ID NO 52
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (5)..(5)
<223> OTHER INFORMATION: Xaa is Arg, Gln or Ser

<400> SEQUENCE: 52

Gly Leu Ser Lys Xaa Cys Phe Gly Leu Lys Leu Asp Arg Ile Gly Ser
1               5                   10                  15

Met Ser Gly Leu Gly Cys
            20

<210> SEQ ID NO 53
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (15)..(15)
<223> OTHER INFORMATION: Xaa is Ser, Asn, Arg, or Cit

<400> SEQUENCE: 53

Gly Leu Ser Lys Gly Cys Phe Gly Leu Lys Leu Asp Arg Ile Xaa Ser
1               5                   10                  15

Met Ser Gly Leu Gly Cys
            20

<210> SEQ ID NO 54
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (19)..(19)
<223> OTHER INFORMATION: Xaa is Ser, Arg, or Asn

<400> SEQUENCE: 54

Gly Leu Ser Lys Gly Cys Phe Gly Leu Lys Leu Asp Arg Ile Gly Ser
1               5                   10                  15

Met Ser Xaa Leu Gly Cys
            20

<210> SEQ ID NO 55
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (21)..(21)
<223> OTHER INFORMATION: Xaa is Ser, Thr, or Arg

<400> SEQUENCE: 55

Gly Leu Ser Lys Gly Cys Phe Gly Leu Lys Leu Asp Arg Ile Gly Ser
1               5                   10                  15

Met Ser Gly Leu Xaa Cys

<210> SEQ ID NO 56
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog A
<220> FEATURE:
<221> NAME/KEY: BINDING
<222> LOCATION: (6)..(6)
<223> OTHER INFORMATION: CH2NH

<400> SEQUENCE: 56

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 57
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analogs B
<220> FEATURE:
<221> NAME/KEY: BINDING
<222> LOCATION: (7)..(7)
<223> OTHER INFORMATION: Xaa replaced with N-Me-Phe

<400> SEQUENCE: 57

Gly Leu Ser Lys Gly Cys Xaa Gly Leu Lys Leu Asp Arg Ile Gly Ser
1               5                   10                  15

Met Ser Gly Leu Gly Cys
            20

<210> SEQ ID NO 58
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog F
<220> FEATURE:
<221> NAME/KEY: BINDING
<222> LOCATION: (8)..(8)
<223> OTHER INFORMATION: tBu

<400> SEQUENCE: 58

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 59
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE

```
<223> OTHER INFORMATION: Analog H
<220> FEATURE:
<221> NAME/KEY: BINDING
<222> LOCATION: (7)..(7)
<223> OTHER INFORMATION: Xaa is replaced with NHCH2-CH(Phe)CO

<400> SEQUENCE: 59

Gly Leu Ser Lys Gly Cys Xaa Gly Leu Lys Leu Asp Arg Ile Gly Ser
1               5                   10                  15

Met Ser Gly Leu Gly Cys
            20

<210> SEQ ID NO 60
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BL - CNP37

<400> SEQUENCE: 60

Gln Glu His Pro Asn Ala Arg Lys Tyr Lys Gly Ala Asn Lys Lys Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 61
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CA

<400> SEQUENCE: 61

Ala Ala Trp Ala Arg Leu Leu Gln Glu His Pro Asn Ala Gly Leu Ser
1               5                   10                  15

Lys Gly Cys Phe Gly Leu Lys Leu Asp Arg Ile Gly Ser Met Ser Gly
            20                  25                  30

Leu Gly Cys
        35

<210> SEQ ID NO 62
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CB

<400> SEQUENCE: 62

Ala Ala Trp Ala Arg Leu Leu Gln Glu His Pro Asn Ala Arg Gly Leu
1               5                   10                  15

Ser Lys Gly Cys Phe Gly Leu Lys Leu Asp Arg Ile Gly Ser Met Ser
            20                  25                  30

Gly Leu Gly Cys
        35
```

<210> SEQ ID NO 63
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CC

<400> SEQUENCE: 63

Asp Leu Arg Val Asp Thr Lys Ser Arg Ala Ala Trp Ala Arg Gly Leu
1               5                   10                  15

Ser Lys Gly Cys Phe Gly Leu Lys Leu Asp Arg Ile Gly Ser Met Ser
            20                  25                  30

Gly Leu Gly Cys
        35

<210> SEQ ID NO 64
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: GANQQ-CNP22

<400> SEQUENCE: 64

Gly Ala Asn Gln Gln Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 65
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: GANRR-CNP22

<400> SEQUENCE: 65

Gly Ala Asn Arg Arg Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 66
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: GANPR-CNP22

<400> SEQUENCE: 66

Gly Ala Asn Pro Arg Gly Leu Ser Lys Gly Cys Phe Gly Leu Lys Leu
1               5                   10                  15

Asp Arg Ile Gly Ser Met Ser Gly Leu Gly Cys
            20                  25

```
<210> SEQ ID NO 67
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: GANSS-CNP22

<400> SEQUENCE: 67

Gly Ala Asn Ser Ser Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 68
<211> LENGTH: 32
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CD
<220> FEATURE:
<221> NAME/KEY: MOD_RES
<222> LOCATION: (1)..(1)
<223> OTHER INFORMATION: N-terminus BNP tail
<220> FEATURE:
<221> NAME/KEY: MOD_RES
<222> LOCATION: (32)..(32)
<223> OTHER INFORMATION: N-terminus BNP tail

<400> SEQUENCE: 68

Ser Pro Lys Met Val Gln Gly Ser Gly Cys Phe Gly Leu Lys Leu Asp
1               5                   10                  15

Arg Ile Gly Ser Met Ser Gly Leu Gly Cys Lys Val Leu Arg Arg His
            20                  25                  30

<210> SEQ ID NO 69
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: GANQQ-CNP22(K4R) - Analog CH

<400> SEQUENCE: 69

Gly Ala Asn Gln Gln Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 70
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: GANSS-CNP22(K4R) - Analog CG

<400> SEQUENCE: 70

Gly Ala Asn Ser Ser Gly Leu Ser Arg Gly Cys Phe Gly Leu Lys Leu
1               5                   10                  15
```

Asp Arg Ile Gly Ser Met Ser Gly Leu Gly Cys
            20                  25

<210> SEQ ID NO 71
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CS

<400> SEQUENCE: 71

Gly Gln Glu His Pro Asn Ala Arg Lys Tyr Lys Gly Ala Asn Pro Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 72
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CT

<400> SEQUENCE: 72

Gly Gln Glu His Pro Asn Ala Arg Lys Tyr Lys Gly Ala Asn Gln Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 73
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CU

<400> SEQUENCE: 73

Gly Gln Glu His Pro Asn Ala Arg Lys Tyr Lys Gly Ala Asn Gln Gln
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 74
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CW

```
<400> SEQUENCE: 74

Gly Gln Glu His Pro Asn Ala Arg Lys Tyr Lys Gly Ala Asn Lys Pro
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 75
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 75

Gly Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 76
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CQ

<400> SEQUENCE: 76

Gly His His Ser His Glu Gln His Pro His Gly Ala Asn Gln Gln Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 77
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CR

<400> SEQUENCE: 77

Gly Ala His His Pro His Glu His Asp Thr His Gly Ala Asn Gln Gln
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 78
<211> LENGTH: 37
<212> TYPE: PRT
<213> ORGANISM: Artificial Sequence
<220> FEATURE:
```

<223> OTHER INFORMATION: Synthetic Polypeptide
<220> FEATURE:
<221> NAME/KEY: MISC_FEATURE
<223> OTHER INFORMATION: Analog CX

<400> SEQUENCE: 78

Gly His His Ser His Glu Gln His Pro His Gly Ala Asn Pro Arg Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 79
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CF

<400> SEQUENCE: 79

Gly Gln Pro Arg Glu Pro Gln Val Tyr Thr Leu Pro Pro Ser Gly Leu
1               5                   10                  15

Ser Lys Gly Cys Phe Gly Leu Lys Leu Asp Arg Ile Gly Ser Met Ser
            20                  25                  30

Gly Leu Gly Cys
        35

<210> SEQ ID NO 80
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CY

<400> SEQUENCE: 80

Gly Gln His Lys Asp Asp Asn Pro Asn Leu Pro Arg Gly Ala Asn Pro
1               5                   10                  15

Arg Gly Leu Ser Lys Gly Cys Phe Gly Leu Lys Leu Asp Arg Ile Gly
            20                  25                  30

Ser Met Ser Gly Leu Gly Cys
        35

<210> SEQ ID NO 81
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CE

<400> SEQUENCE: 81

Gly Glu Arg Ala Phe Lys Ala Trp Ala Val Ala Arg Leu Ser Gln Gly
1               5                   10                  15

Leu Ser Lys Gly Cys Phe Gly Leu Lys Leu Asp Arg Ile Gly Ser Met
            20                  25                  30

Ser Gly Leu Gly Cys

```
                35

<210> SEQ ID NO 82
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CZ

<400> SEQUENCE: 82

Phe Gly Ile Pro Met Asp Arg Ile Gly Arg Asn Pro Arg Gly Leu Ser
1               5                   10                  15

Lys Gly Cys Phe Gly Leu Lys Leu Asp Arg Ile Gly Ser Met Ser Gly
            20                  25                  30

Leu Gly Cys
        35

<210> SEQ ID NO 83
<211> LENGTH: 40
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog DA

<400> SEQUENCE: 83

Gly Lys Arg Thr Gly Gln Tyr Lys Leu Gly Ser Lys Thr Gly Pro Gly
1               5                   10                  15

Pro Lys Gly Leu Ser Lys Gly Cys Phe Gly Leu Lys Leu Asp Arg Ile
            20                  25                  30

Gly Ser Met Ser Gly Leu Gly Cys
        35                  40

<210> SEQ ID NO 84
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CK

<400> SEQUENCE: 84

Gly Gln Pro Arg Glu Pro Gln Val Tyr Thr Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 85
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CL

<400> SEQUENCE: 85
```

```
Gly Val Pro Gln Val Ser Thr Ser Thr Gly Ala Asn Gln Gln Gly Leu
1               5                   10                  15

Ser Arg Gly Cys Phe Gly Leu Lys Leu Asp Arg Ile Gly Ser Met Ser
                20                  25                  30

Gly Leu Gly Cys
            35

<210> SEQ ID NO 86
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CM

<400> SEQUENCE: 86

Gly Gln Pro Ser Ser Ser Gln Ser Thr Gly Ala Asn Gln Gln Gly
1               5                   10                  15

Leu Ser Arg Gly Cys Phe Gly Leu Lys Leu Asp Arg Ile Gly Ser Met
                20                  25                  30

Ser Gly Leu Gly Cys
            35

<210> SEQ ID NO 87
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CN

<400> SEQUENCE: 87

Gly Gln Thr His Ser Ser Gly Thr Gln Ser Gly Ala Asn Gln Gln Gly
1               5                   10                  15

Leu Ser Arg Gly Cys Phe Gly Leu Lys Leu Asp Arg Ile Gly Ser Met
                20                  25                  30

Ser Gly Leu Gly Cys
            35

<210> SEQ ID NO 88
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CO

<400> SEQUENCE: 88

Gly Ser Thr Gly Gln Trp His Ser Glu Ser Gly Ala Asn Gln Gln Gly
1               5                   10                  15

Leu Ser Arg Gly Cys Phe Gly Leu Lys Leu Asp Arg Ile Gly Ser Met
                20                  25                  30

Ser Gly Leu Gly Cys
            35

<210> SEQ ID NO 89
<211> LENGTH: 37
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CP

<400> SEQUENCE: 89

Gly Ser Ser Ser Ser Ser Ser Ser Ser Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 90
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N-terminus is optionally modified with bone
      targeting compound, a bisphosphonates, polyAsp, polyGlu,
      osteopontin, osteocalcin, or sialoprotein peptides, negatively
      charged PEG molecules or natural polymers
<220> FEATURE:
<221> NAME/KEY: MOD_RES
<222> LOCATION: (6)..(6)
<223> OTHER INFORMATION: Xaa is Cys or another natural or unnatural
      amino acid
<220> FEATURE:
<221> NAME/KEY: MOD_RES
<222> LOCATION: (7)..(7)
<223> OTHER INFORMATION: Xaa is Phe or another natural or unnatural
      amino acid
<220> FEATURE:
<221> NAME/KEY: MOD_RES
<222> LOCATION: (8)..(8)
<223> OTHER INFORMATION: Xaa is Gly, a larger natural or unnatural amino
      acid
<220> FEATURE:
<221> NAME/KEY: MISC_FEATURE
<222> LOCATION: (22)..(22)
<223> OTHER INFORMATION: C-terminus is optionally modified with bone
      targeting compound, a bisphosphonates, polyAsp, polyGlu,
      osteopontin, osteocalcin, or sialoprotein peptides, negatively
      charged PEG molecules or natural polymers

<400> SEQUENCE: 90

Gly Leu Ser Lys Gly Xaa Xaa Xaa Leu Lys Leu Asp Arg Ile Gly Ser
1               5                   10                  15

Met Ser Gly Leu Gly Cys
            20

<210> SEQ ID NO 91
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog J
<220> FEATURE:
<221> NAME/KEY: MOD_RES
<222> LOCATION: (6)..(6)
<223> OTHER INFORMATION: Xaa is CH2-NH
<220> FEATURE:
<221> NAME/KEY: BINDING
<222> LOCATION: (9)..(9)
```

```
<223> OTHER INFORMATION: N-Me
<220> FEATURE:
<221> NAME/KEY: BINDING
<222> LOCATION: (20)..(20)
<223> OTHER INFORMATION: N-Me

<400> SEQUENCE: 91

Gly Leu Ser Lys Gly Xaa Phe Gly Leu Lys Leu Asp Arg Ile Gly Ser
1               5                   10                  15

Met Ser Gly Leu Gly Cys
            20

<210> SEQ ID NO 92
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog K
<220> FEATURE:
<221> NAME/KEY: BINDING
<222> LOCATION: (9)..(9)
<223> OTHER INFORMATION: N-Me
<220> FEATURE:
<221> NAME/KEY: BINDING
<222> LOCATION: (20)..(20)
<223> OTHER INFORMATION: N-Me

<400> SEQUENCE: 92

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 93
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog L
<220> FEATURE:
<221> NAME/KEY: BINDING
<222> LOCATION: (9)..(9)
<223> OTHER INFORMATION: N-Me
<220> FEATURE:
<221> NAME/KEY: BINDING
<222> LOCATION: (11)..(11)
<223> OTHER INFORMATION: N-Me
<220> FEATURE:
<221> NAME/KEY: BINDING
<222> LOCATION: (20)..(20)
<223> OTHER INFORMATION: N-Me

<400> SEQUENCE: 93

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 94
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
```

```
<221> NAME/KEY: MISC_FEATURE
<223> OTHER INFORMATION: Analog M
<220> FEATURE:
<221> NAME/KEY: BINDING
<222> LOCATION: (9)..(9)
<223> OTHER INFORMATION: N-Me
<220> FEATURE:
<221> NAME/KEY: BINDING
<222> LOCATION: (11)..(11)
<223> OTHER INFORMATION: N-Me

<400> SEQUENCE: 94

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 95
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog Z

<400> SEQUENCE: 95

Gly Leu Ser Arg Gly Cys Tyr Gly Leu Lys Leu Asp Arg Ile Gly Ser
1               5                   10                  15

Met Ser Gly Leu Gly Cys
            20

<210> SEQ ID NO 96
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AA

<400> SEQUENCE: 96

Gly Leu Ser Arg Gly Cys Phe Val Leu Lys Leu Asp Arg Ile Gly Ser
1               5                   10                  15

Met Ser Gly Leu Gly Cys
            20

<210> SEQ ID NO 97
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AB

<400> SEQUENCE: 97

Gly Leu Ser Arg Gly Cys Phe Ser Leu Lys Leu Asp Arg Ile Gly Ser
1               5                   10                  15

Met Ser Gly Leu Gly Cys
            20

<210> SEQ ID NO 98
<211> LENGTH: 22
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AC

<400> SEQUENCE: 98

Gly Leu Ser Arg Gly Cys Phe Thr Leu Lys Leu Asp Arg Ile Gly Ser
1               5                   10                  15

Met Ser Gly Leu Gly Cys
            20

<210> SEQ ID NO 99
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AD

<400> SEQUENCE: 99

Gly Leu Ser Arg Gly Cys Phe Gly Thr Lys Leu Asp Arg Ile Gly Ser
1               5                   10                  15

Met Ser Gly Leu Gly Cys
            20

<210> SEQ ID NO 100
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AE

<400> SEQUENCE: 100

Gly Leu Ser Arg Gly Cys Phe Gly Leu Lys Leu Asp Arg Ile Arg Ser
1               5                   10                  15

Met Ser Gly Leu Gly Cys
            20

<210> SEQ ID NO 101
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AF
<220> FEATURE:
<221> NAME/KEY: MOD_RES
<222> LOCATION: (15)..(15)
<223> OTHER INFORMATION: Xaa is Cit

<400> SEQUENCE: 101

Gly Leu Ser Arg Gly Cys Phe Gly Leu Lys Leu Asp Arg Ile Xaa Ser
1               5                   10                  15

Met Ser Gly Leu Gly Cys
            20

<210> SEQ ID NO 102
<211> LENGTH: 22
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AG

<400> SEQUENCE: 102

Gly Leu Ser Arg Gly Cys Phe Gly Leu Lys Leu Asp Arg Ile Gly Ser
1               5                   10                  15

Val Ser Gly Leu Gly Cys
            20

<210> SEQ ID NO 103
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AJ

<400> SEQUENCE: 103

Gly Leu Ser Arg Gly Cys Phe Gly Leu Lys Leu Asp Arg Ile Gly Ser
1               5                   10                  15

Met Ser Gly Val Gly Cys
            20

<210> SEQ ID NO 104
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AK
<220> FEATURE:
<221> NAME/KEY: MOD_RES
<222> LOCATION: (20)..(20)
<223> OTHER INFORMATION: Xaa is tBu-Ala

<400> SEQUENCE: 104

Gly Leu Ser Arg Gly Cys Phe Gly Leu Lys Leu Asp Arg Ile Gly Ser
1               5                   10                  15

Met Ser Gly Xaa Gly Cys
            20

<210> SEQ ID NO 105
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AT

<400> SEQUENCE: 105

Glu Leu Ser Glu Gly Cys Phe Gly Leu Lys Leu Asp Arg Ile Gly Ser
1               5                   10                  15

Met Ser Gly Leu Gly Cys
            20

<210> SEQ ID NO 106
<211> LENGTH: 22
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AV
<220> FEATURE:
<221> NAME/KEY: MOD_RES
<222> LOCATION: (1)..(1)
<223> OTHER INFORMATION: N-terminus modified with pentanoic acid

<400> SEQUENCE: 106

Glu Leu Ser Glu Gly Cys Phe Gly Leu Lys Leu Asp Arg Ile Gly Ser
1               5                   10                  15

Met Ser Gly Leu Gly Cys
            20

<210> SEQ ID NO 107
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AW
<220> FEATURE:
<221> NAME/KEY: MOD_RES
<222> LOCATION: (1)..(1)
<223> OTHER INFORMATION: Heptanoic acid modifying N-terminus

<400> SEQUENCE: 107

Glu Leu Ser Glu Gly Cys Phe Gly Leu Lys Leu Asp Arg Ile Gly Ser
1               5                   10                  15

Met Ser Gly Leu Gly Cys
            20

<210> SEQ ID NO 108
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BB
<220> FEATURE:
<221> NAME/KEY: MOD_RES
<222> LOCATION: (1)..(1)
<223> OTHER INFORMATION: N-terminus modified with heptanoic acid

<400> SEQUENCE: 108

Glu Leu Ser Lys Gly Cys Phe Gly Leu Lys Leu Asp Arg Ile Gly Ser
1               5                   10                  15

Met Ser Gly Leu Gly Cys
            20

<210> SEQ ID NO 109
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BC
<220> FEATURE:
<221> NAME/KEY: MOD_RES
<222> LOCATION: (1)..(1)
<223> OTHER INFORMATION: N-terminus modified with pentanoic acid
```

```
<400> SEQUENCE: 109

Glu Leu Ser Lys Gly Cys Phe Gly Leu Lys Leu Asp Arg Ile Gly Ser
1               5                   10                  15

Met Ser Gly Leu Gly Cys
            20

<210> SEQ ID NO 110
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BF
<220> FEATURE:
<221> NAME/KEY: MOD_RES
<222> LOCATION: (10)..(10)
<223> OTHER INFORMATION: Xaa is Cit

<400> SEQUENCE: 110

Gly Leu Ser Arg Gly Cys Phe Gly Leu Xaa Leu Asp Arg Ile Gly Ser
1               5                   10                  15

Met Ser Gly Leu Gly Cys
            20

<210> SEQ ID NO 111
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BG

<400> SEQUENCE: 111

Gly Leu Ser Arg Gly Cys Phe Gly Leu Gln Leu Asp Arg Ile Gly Ser
1               5                   10                  15

Met Ser Gly Leu Gly Cys
            20

<210> SEQ ID NO 112
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BH

<400> SEQUENCE: 112

Gly Leu Ser Arg Gly Cys Phe Gly Leu Arg Leu Asp Arg Ile Gly Ser
1               5                   10                  15

Met Ser Gly Leu Gly Cys
            20

<210> SEQ ID NO 113
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BJ
```

```
<400> SEQUENCE: 113

Gly Leu Ser Arg Gly Cys Phe Gly Leu Lys Leu Asp Arg Ile Asn Ser
1               5                   10                  15

Met Ser Gly Leu Gly Cys
            20

<210> SEQ ID NO 114
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BK

<400> SEQUENCE: 114

Gly Leu Ser Arg Gly Cys Phe Gly Leu Lys Leu Asp Arg Ile Ser Ser
1               5                   10                  15

Met Ser Gly Leu Gly Cys
            20

<210> SEQ ID NO 115
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog N
<220> FEATURE:
<221> NAME/KEY: MISC_FEATURE
<222> LOCATION: (1)..(22)
<223> OTHER INFORMATION: All D-amino acids

<400> SEQUENCE: 115

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 116
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BD
<220> FEATURE:
<221> NAME/KEY: BINDING
<222> LOCATION: (9)..(9)
<223> OTHER INFORMATION: N-Me

<400> SEQUENCE: 116

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 117
<211> LENGTH: 22
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MISC_FEATURE
<223> OTHER INFORMATION: Analog BN
<220> FEATURE:
<221> NAME/KEY: BINDING
<222> LOCATION: (11)..(11)
<223> OTHER INFORMATION: N-Me

<400> SEQUENCE: 117

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 118
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BE
<220> FEATURE:
<221> NAME/KEY: BINDING
<222> LOCATION: (20)..(20)
<223> OTHER INFORMATION: N-Me

<400> SEQUENCE: 118

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 119
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog V
<220> FEATURE:
<221> NAME/KEY: BINDING
<222> LOCATION: (7)..(7)
<223> OTHER INFORMATION: 3,4-dichloro

<400> SEQUENCE: 119

Gly Leu Ser Gly Gly Cys Phe Gly Leu Lys Leu Asp Arg Ile Gly Ser
1               5                   10                  15

Met Ser Gly Leu Gly Cys
            20

<210> SEQ ID NO 120
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog X
<220> FEATURE:
<221> NAME/KEY: BINDING
<222> LOCATION: (7)..(7)
<223> OTHER INFORMATION: 3-methyl

<400> SEQUENCE: 120

Gly Leu Ser Gly Gly Cys Phe Gly Leu Lys Leu Asp Arg Ile Gly Ser
```

```
1               5                   10                  15
Met Ser Gly Leu Gly Cys
            20

<210> SEQ ID NO 121
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BP

<400> SEQUENCE: 121

Gly Leu Ser Arg Ser Cys Phe Gly Leu Lys Leu Asp Arg Ile Gly Ser
1               5                   10                  15

Met Ser Gly Leu Gly Cys
            20

<210> SEQ ID NO 122
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BO

<400> SEQUENCE: 122

Gly Leu Ser Arg Arg Cys Phe Gly Leu Lys Leu Asp Arg Ile Gly Ser
1               5                   10                  15

Met Ser Gly Leu Gly Cys
            20

<210> SEQ ID NO 123
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog P

<400> SEQUENCE: 123

Gly Leu Ser Gly Gly Cys Phe Gly Leu Arg Leu Asp Arg Ile Gly Ser
1               5                   10                  15

Met Ser Gly Leu Gly Cys
            20

<210> SEQ ID NO 124
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BY

<400> SEQUENCE: 124

Gly Leu Ser Arg Gly Cys Phe Gly Leu Ser Leu Asp Arg Ile Gly Ser
1               5                   10                  15

Met Ser Gly Leu Gly Cys
            20
```

<210> SEQ ID NO 125
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BZ

<400> SEQUENCE: 125

Gly Leu Ser Arg Gly Cys Phe Gly Leu Lys Leu Asp Arg Ile Gly Gln
1               5                   10                  15

Met Ser Gly Leu Gly Cys
            20

<210> SEQ ID NO 126
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BX

<400> SEQUENCE: 126

Gly Leu Ser Arg Gly Cys Phe Gly Leu Lys Leu Asp Arg Ile Gly Ser
1               5                   10                  15

Asn Ser Gly Leu Gly Cys
            20

<210> SEQ ID NO 127
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BQ

<400> SEQUENCE: 127

Gly Leu Ser Arg Gly Cys Phe Gly Leu Lys Leu Asp Arg Ile Gly Ser
1               5                   10                  15

Met Ser Ser Leu Gly Cys
            20

<210> SEQ ID NO 128
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BR

<400> SEQUENCE: 128

Gly Leu Ser Arg Gly Cys Phe Gly Leu Lys Leu Asp Arg Ile Gly Ser
1               5                   10                  15

Met Ser Arg Leu Gly Cys
            20

<210> SEQ ID NO 129
<211> LENGTH: 22

<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BS

<400> SEQUENCE: 129

Gly Leu Ser Arg Gly Cys Phe Gly Leu Lys Leu Asp Arg Ile Gly Ser
1               5                   10                  15

Met Ser Gly Arg Gly Cys
            20

<210> SEQ ID NO 130
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BT

<400> SEQUENCE: 130

Gly Leu Ser Arg Gly Cys Phe Gly Leu Lys Leu Asp Arg Ile Gly Ser
1               5                   10                  15

Met Ser Gly Leu Ser Cys
            20

<210> SEQ ID NO 131
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BU

<400> SEQUENCE: 131

Gly Leu Ser Arg Gly Cys Phe Gly Leu Lys Leu Asp Arg Ile Gly Ser
1               5                   10                  15

Met Ser Gly Leu Thr Cys
            20

<210> SEQ ID NO 132
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BW

<400> SEQUENCE: 132

Gly Leu Ser Arg Gly Cys Phe Gly Leu Lys Leu Asp Arg Ile Gly Ser
1               5                   10                  15

Met Ser Gly Leu Arg Cys
            20

<210> SEQ ID NO 133
<211> LENGTH: 15
<212> TYPE: PRT
<213> ORGANISM: Artificial Sequence
<220> FEATURE:
<223> OTHER INFORMATION: Synthetic Polypeptide

```
<220> FEATURE:
<221> NAME/KEY: MISC_FEATURE
<223> OTHER INFORMATION: Analog CJ

<400> SEQUENCE: 133

Arg Ser Ser Cys Phe Gly Gly Arg Ile Asp Arg Ile Gly Ala Cys
1               5                   10                  15

<210> SEQ ID NO 134
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: N-terminal linked to CNP22 by disuccinimidyl
      glutarate

<400> SEQUENCE: 134

Gly Leu Ser Arg Gly Cys Phe Gly Leu Arg Leu Asp Arg Ile Gly Ser
1               5                   10                  15

Met Ser Gly Leu Gly Cys
            20

<210> SEQ ID NO 135
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: N-terminal linked to CNP22 by Bis-PEO5

<400> SEQUENCE: 135

Gly Leu Ser Arg Gly Cys Phe Gly Leu Arg Leu Asp Arg Ile Gly Ser
1               5                   10                  15

Met Ser Gly Leu Gly Cys
            20

<210> SEQ ID NO 136
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog E
<220> FEATURE:
<221> NAME/KEY: MOD_RES
<222> LOCATION: (7)..(7)
<223> OTHER INFORMATION: Xaa is D-Phe

<400> SEQUENCE: 136

Gly Leu Ser Lys Gly Cys Xaa Gly Leu Lys Leu Asp Arg Ile Gly Ser
1               5                   10                  15

Met Ser Gly Leu Gly Cys
            20

<210> SEQ ID NO 137
<211> LENGTH: 22
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MISC_FEATURE
<223> OTHER INFORMATION: Analog G
<220> FEATURE:
<221> NAME/KEY: MOD_RES
<222> LOCATION: (7)..(7)
<223> OTHER INFORMATION: Xaa is 3-Cl-Phe

<400> SEQUENCE: 137

Gly Leu Ser Lys Gly Cys Xaa Gly Leu Lys Leu Asp Arg Ile Gly Ser
1               5                   10                  15

Met Ser Gly Leu Gly Cys
            20

<210> SEQ ID NO 138
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa comprises one or more amino acids selected
      from Gly-Leu-Ser-Lys-Gly or substitutions at one or more of these
      amino acids and further comprises a hydrophilic or water soluable
      polymer

<400> SEQUENCE: 138

Xaa Cys Phe Gly Leu Lys Leu Asp Arg Ile Gly Ser Met Ser Gly Leu
1               5                   10                  15

Gly Cys

<210> SEQ ID NO 139
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N-terminus is modified with a natural and/or
      synthetic polymer
<220> FEATURE:
<221> NAME/KEY: MISC_FEATURE
<222> LOCATION: (17)..(17)
<223> OTHER INFORMATION: C-terminus is modified with a natural and/or
      synthetic polymer

<400> SEQUENCE: 139

Cys Phe Gly Leu Lys Leu Asp Arg Ile Gly Ser Met Ser Gly Leu Gly
1               5                   10                  15

Cys

<210> SEQ ID NO 140
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N-terminus is modified with a natural and/or
      synthetic polymer
<220> FEATURE:
<221> NAME/KEY: MISC_FEATURE
<222> LOCATION: (22)..(22)
<223> OTHER INFORMATION: C-terminus is modified with a natural and/or
      synthetic polymer
```

```
<400> SEQUENCE: 140

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 141
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: C-terminus is modified with a natural and/or
      synthetic polymeric group or combination thereof
<220> FEATURE:
<221> NAME/KEY: MOD_RES
<222> LOCATION: (5)..(5)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Glu or Ser
<220> FEATURE:
<221> NAME/KEY: MISC_FEATURE
<222> LOCATION: (17)..(17)
<223> OTHER INFORMATION: C-terminus is optionally modified with a
      natural and/or synthetic polymeric group or combination thereof

<400> SEQUENCE: 141

Cys Phe Gly Leu Xaa Leu Asp Arg Ile Gly Ser Met Ser Gly Leu Gly
1               5                   10                  15

Cys

<210> SEQ ID NO 142
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N-terminus is optionally modified with bone- or
      cartilage-targeting moieties, moieties that reduce renal
      clearance, hydrophilic polymers, carbohydrates, hydrophobic acids
      and combinations thereof
<220> FEATURE:
<221> NAME/KEY: MOD_RES
<222> LOCATION: (1)..(1)
<223> OTHER INFORMATION: Xaa is absent or may comprise 1 to 5 amino
      acids from Gly-Leu-Ser-Lys-Gly, optionally substituted with a
      natural or unnatural amino acid
<220> FEATURE:
<221> NAME/KEY: MOD_RES
<222> LOCATION: (6)..(6)
<223> OTHER INFORMATION: Xaa is Lys, any natural or unnatural amino acid
      or any amino acid that does not have a reactive primary amine on a
      side chain
<220> FEATURE:
<221> NAME/KEY: MOD_RES
<222> LOCATION: (18)..(18)
<223> OTHER INFORMATION: C-terminus is optionally modified with bone- or
      cartilage-targeting moieties, moieties that reduce renal
      clearance, hydrophilic polymers, carbohydrates, hydrophobic acids
      and combinations thereof

<400> SEQUENCE: 142

Xaa Cys Phe Gly Leu Xaa Leu Asp Arg Ile Gly Ser Met Ser Gly Leu
1               5                   10                  15

Gly Cys
```

```
<210> SEQ ID NO 143
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N-terminus is optionally modified with
      cartilage or bone targeting compounds, a bisphosphonate, polyAsp,
      polyGlu, osteopontin peptides, osteocalcin peptides, sialoprotein
      peptides, charged PEG molecules or hydrophilic polymers
<220> FEATURE:
<221> NAME/KEY: MOD_RES
<222> LOCATION: (4)..(4)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Ser or Glu
<220> FEATURE:
<221> NAME/KEY: MISC_FEATURE
<222> LOCATION: (6)..(7)
<223> OTHER INFORMATION: Peptide bone between Cys6 and position 7 may be
      replaced with peptide bond isosteres
<220> FEATURE:
<221> NAME/KEY: MOD_RES
<222> LOCATION: (7)..(7)
<223> OTHER INFORMATION: Xaa is L-Phe, D-Phe, N-alkylated Phe, or Phe
      analog
<220> FEATURE:
<221> NAME/KEY: MOD_RES
<222> LOCATION: (8)..(8)
<223> OTHER INFORMATION: Xaa is Gly, tert-butyl-Gly, Thr, Ser, Val or
      Asn
<220> FEATURE:
<221> NAME/KEY: MOD_RES
<222> LOCATION: (9)..(9)
<223> OTHER INFORMATION: Xaa is Leu, Ser, Thr or peptide bond isosteres
      thereof
<220> FEATURE:
<221> NAME/KEY: MISC_FEATURE
<222> LOCATION: (9)..(10)
<223> OTHER INFORMATION: Peptide bond between positions 9 and 10 may be
      replaced with peptide bond isosteres
<220> FEATURE:
<221> NAME/KEY: MOD_RES
<222> LOCATION: (10)..(10)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Ser or Glu
<220> FEATURE:
<221> NAME/KEY: MOD_RES
<222> LOCATION: (11)..(11)
<223> OTHER INFORMATION: Xaa is Leu or Asn
<220> FEATURE:
<221> NAME/KEY: MISC_FEATURE
<222> LOCATION: (11)..(12)
<223> OTHER INFORMATION: Peptide bond between positions 11 and 12 may be
      replaced with peptide isosteres (e.g. N-Me-Leu)
<220> FEATURE:
<221> NAME/KEY: MOD_RES
<222> LOCATION: (14)..(14)
<223> OTHER INFORMATION: Xaa is Ile, tert-butyl-Gly (tBu-Gly), or Asn
<220> FEATURE:
<221> NAME/KEY: MISC_FEATURE
<222> LOCATION: (14)..(15)
<223> OTHER INFORMATION: Peptide bone between positions 14 and 15 may be
      replaced with peptide bone isosteres (e.g. N-Me-Ile)
<220> FEATURE:
<221> NAME/KEY: MOD_RES
<222> LOCATION: (15)..(15)
<223> OTHER INFORMATION: Xaa is Gly, Arg, Ser or Asn
<220> FEATURE:
<221> NAME/KEY: MOD_RES
<222> LOCATION: (17)..(17)
<223> OTHER INFORMATION: Xaa is Met, Val, Asn, beta-Cl-Ala,
      2-aminobutyric acid (Abu), or 2-amino-isobutyric acid (Aib)
```

```
<220> FEATURE:
<221> NAME/KEY: MOD_RES
<222> LOCATION: (20)..(20)
<223> OTHER INFORMATION: Xaa is Leu, norleucine (Nle), homoleucine
      (Hleu), Val, tert-butyl-Ala (tBu-Ala), Arg, Thr, or Ser
<220> FEATURE:
<221> NAME/KEY: MISC_FEATURE
<222> LOCATION: (20)..(21)
<223> OTHER INFORMATION: Peptide bone between position 20 and Gly21 may
      be replaced with peptide bond isosteres
<220> FEATURE:
<221> NAME/KEY: MISC_FEATURE
<222> LOCATION: (22)..(22)
<223> OTHER INFORMATION: C-terminus is optionally modified with
      cartilage or bone targeting compounds, a bisphosphonate, polyAsp,
      polyGlu, osteopontin peptides, osteocalcin peptides, sialoprotein
      peptides, charged PEG molecules or hydrophilic polymers

<400> SEQUENCE: 143

Gly Leu Ser Xaa Gly Cys Xaa Xaa Xaa Xaa Xaa Asp Arg Xaa Xaa Ser
1               5                   10                  15

Xaa Ser Gly Xaa Gly Cys
            20

<210> SEQ ID NO 144
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 144

Gly His Lys Ser Glu Val Ala His Arg Phe Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
            35
```

VARIANTS OF C-TYPE NATRIURETIC PEPTIDES

CROSS REFERENCE TO RELATED APPLICATIONS

The present application claims priority to U.S. provisional application No. 60/989,497, filed on Nov. 21, 2007, and U.S. provisional application No. 61/061,488, filed on Jun. 13, 2008. The disclosure of each prior application is incorporated by reference herein in its entirety.

FIELD OF THE INVENTION

The field of the invention relates, in general, to variants of C-type natriuretic peptide (CNP), compositions comprising CNP variants, and methods of using CNP variants to treat disorders responsive to CNP, including but not limited to bone-related disorders such as skeletal dysplasias (e.g., achondroplasia) and vascular smooth muscle disorders.

BACKGROUND OF THE INVENTION

The natriuretic peptide family consists of three structurally related peptides: atrial natriuretic peptide (ANP) (Genbank Accession No. NP_006163, for the ANP precursor protein, NPPA), brain natriuretic peptide (BNP) (GenBank Accession No. NP_002512, for the BNP precursor protein, NPPB), and C-type natriuretic peptide (CNP) (Biochem. Biophys. Res. Commun., 168: 863-870 (1990) (GenBank Accession No. NP_077720, for the CNP precursor protein, NPPC) (J. Hypertens., 10: 907-912 (1992)). These small, single chain peptides (ANP, BNP, CNP) have a 17-amino acid loop structure (Levin et al., N. Engl. J. Med., 339: 863-870 (1998)) and have important roles in multiple biological processes. ANP and BNP bind to and activate the natriuretic peptide receptor A (NPR-A), also termed guanalyl cyclase A (GC-A), resulting in higher intracellular cyclic guanosine monophosphate (cGMP) levels. Likewise, CNP interacts with NPR-B (GC-B) to stimulate the generation of cGMP (J. Hypertens., 10: 1111-1114 (1992)). A third type of receptor, NPR-C, binds each of the natriuretic peptides with high affinity and functions primarily to capture the peptides from the extracellular compartment and deposit the peptides into lysosomes, where they are degraded (Science, 238: 675-678 (1987)). ANP and BNP are produced primarily within the muscle cells of the heart, and are believed to have important roles in cardiovascular homeostasis (Science, 252: 120-123 (1991)). CNP is expressed more widely, including in the central nervous system, reproductive tract, bone and endothelium of blood vessels (Hypertension, 49: 419-426 (2007)).

In humans, CNP is initially produced from the natriuretic peptide precursor C (NPPC) gene as a single chain 126-amino acid pre-pro polypeptide (Biochem. Biophys. Res. Commun., 168: 863-870 (1990)). Removal of the signal peptide yields pro-CNP, and further cleavage by the endoprotease furin generates an active 53-amino acid peptide (CNP-53), which is secreted and cleaved again by an unknown enzyme to produce the mature 22-amino acid peptide (CNP-22) (Wu, J. Biol. Chem. 278: 25847-852 (2003)). CNP-53 and CNP-22 differ in their distribution, with CNP-53 predominating in tissues, while CNP-22 is mainly found in plasma and cerebrospinal fluid (J. Alfonzo, Recept. Signal. Transduct. Res., 26: 269-297 (2006)). The predominant CNP form in cartilage is unknown. Both CNP-53 and CNP-22 bind similarly to NPR-B. Furthermore, they both induce cGMP production in a dose-dependent and similar fashion (V T Yeung, Peptides, 17: 101-106 (1996)).

Natural CNP gene and polypeptide have been previously described. U.S. Pat. No. 5,352,770 discloses isolated and purified CNP-22 from porcine brain identical in sequence to human CNP and its use in treating cardiovascular indications. U.S. Pat. No. 6,034,231 discloses the human gene and polypeptide of proCNP (126 amino acids) and the human CNP-53 gene and polypeptide.

Clearance of CNP from the extracellular space occurs through the action of membrane-bound neutral endopeptidase (NEP), which rapidly degrades CNP (Biochem. J., 291 (Pt 1): 83-88 (1993)), and through NPR-C, which binds to and deposits CNP into lysosomes, where CNP is degraded. CNP has been shown to have an in vivo half-life of 2.6 min in the normal human (J. Clin. Endocrinol. Metab., 78: 1428-35 (1994)). The low plasma concentration of CNP (J. Bone Moner. Res., 19 (Suppl. 1)S20 (2004)) and its co-expression with NPR-B in a number of tissues suggests that CNP functions primarily through an autocrine/paracrine mechanism.

As stated above, CNP binds to and activates natriuretic peptide receptor B (NPR-B), also termed guanylyl cyclase B (GC-B), resulting in higher intracellular cyclic guanosine monophosphate (cGMP) levels. Downstream signaling mediated by cGMP generation influences a diverse array of biological processes that include endochondral ossification. Accordingly, elevated or depressed levels of any of the components in this pathway may lead to aberrant bone growth. For example, knockout of either CNP or NPR-B in mouse models results in animals having a dwarfed phenotype with shorter long bones and vertebrae. Mutations in human NPR-B that block proper CNP signaling have been identified and result in dwarfism (Olney, et al., J. Clin. Endocrinol. Metab. 91(4): 1229-1232 (2006); Bartels, et al., Am. J. Hum. Genet. 75: 27-34 (2004)). In contrast, mice engineered to produce elevated levels of CNP display elongated long bones and vertebrae.

Achondroplasia is a result of an autosomal dominant mutation in the gene for fibroblast growth factor receptor 3 (FGFR-3), which causes an abnormality of cartilage formation. FGFR-3 normally has a negative regulatory effect on chondrocyte growth, and hence bone growth. In achondroplasia, the mutated form of FGFR-3 is constitutively active, which leads to severely shortened bones. Both chondrocyte proliferation and differentiation appear to be disturbed, leading to remarkably short growth plate cartilage (P. Krejci et al., J. Cell Sci. 118: 5089-5100 (2005)). Endochondral ossification is the process that governs longitudinal long-bone growth. There are four zones of the growth plate—resting, proliferative, hypertrophic and zone of calcification. In the growth plate, NPR-B is expressed by proliferative cells while NPR-C is expressed by hypertrophic cells (Yamashite et al., J. Biochem. 127: 177-179 (2000)). In normal endochondral bone growth, chondrocytes organize in columns and proliferate in the proliferative zone of the growth plate. These columns are disorganized in achondroplasia patients. Additionally, the hypertrophic zone is where the cells become large and eventually apoptose (lyse), leading to osteocyte invasion and mineralization. The hypertrophic chondrocytes and the overall size of the zone are much smaller in achondroplasia patients than in normal patients. CNP is an agonist for NPR-B, a positive regulator of chondrocyte and bone growth. Downstream signaling of CNP/NPR-B inhibits the FGFR-3 pathway at the level of mitogen-activated protein kinase (MAP K). Inhibition at MAP K promotes proliferation and differentiation of the chondrocytes in the proliferative and hypertrophic zones of the growth plate, resulting in bone growth.

In humans activating mutations of FGFR-3 are the primary cause of genetic dwarfism. Mice having activated FGFR-3 serve as a model of achondroplasia, the most common form of the skeletal dysplasias, and overexpression of CNP rescues these animals from dwarfism. Accordingly, CNP and functional variants of CNP are potential therapeutics for treatment of the various skeletal dysplasias.

Therapeutic use of CNP is currently limited by its short plasma half-life, which has been shown to be 2.6 minutes in vivo in humans (J. Clin. Endocrinol. Metab., 78: 1428-35 (1994)). To increase CNP concentration above intrinsic levels (about 5 pM) typically found in human plasma, continuous infusion has been necessary in all human and animal studies using systemically administered CNP. A CNP variant having a longer in vivo serum half-life and exhibiting similar or improved activity to that of wild-type CNP is important for a sustainable therapeutic strategy. Two mechanisms by which the half-life of CNP is reduced in human plasma are degradation by neutral endopeptidase (NEP) and clearance by natriuretic peptide receptor C(NPR-C) (Growth Horm. & IGF Res., 16: S6-S14 (2006)). Modifications of peptides reportedly can improve resistance to endopeptidase and exopeptidase cleavage (Amino Acids, 30: 351-367 (2006); Curr. Opin. Biotech., 17: 638-642 (2006)).

The biological activities of various analogs and derivatives of CNP have been evaluated. By substituting S-methyl Cys in place of both $Cys_6$ and $Cys_{22}$, cyclization of the peptide via a Cys6-Cys22 disulfide linkage was reportedly shown to be important for the activity of CNP in stimulating cGMP formation (Biochem. Biophys. Res. Comm., 183: 964-969 (1992), also using alanine scanning to identify amino acids important for CNP functionality). A significant additional enhancement of activity reportedly results from the combined presence of the amino acids $Leu_9$, $Lys_{10}$, and $Leu_{11}$. U.S. Pat. No. 5,434,133 describes CNP analogs comprising CNP-22 with substitutions at amino acid position 6, 7, 9, 11, or 22, wherein the amino acid is selected from Cys or Pmp (pentacyclomercaptopropionic acid) at position 6, Phe, 4-chloro-Phe, 4-fluoro-Phe, 4-nitro-Phe, or Cha (3-cyclohexyl-Ala) at position 7, Gly, Val, Aib, or tLeu at position 9, Leu or Ile at position 11, and Cys or Pmp at position 22.

U.S. Patent Publication No. 2004/0138134 (now U.S. Pat. No. 7,276,481) describes CNP variants comprising amino acids $Cys_6$ to $Cys_{22}$ of CNP-22 ("CNP-17") which include at least one substitution for another natural amino acid at position 9, 10, 11, 16, 17, 19, or 20, CNP variants with insertions and deletions, such as addition of a His residue at the reported primary site of NEP cleavage, between $Cys_6$ and $Phe_7$, and methods of using such variants for increasing the size of a bone growth plate in abnormal bone and elongation of an abnormal bone. However, no significant gains in activity as measured by cGMP production were obtained for these variants, and activity was diminished for nearly all of the variants, as observed in an in vitro cell-based method (Example 6). Further no supportive data, such as for example in vitro stability or in vivo determination of improved pharmacokinetics (PK) were provided to substantiate the asserted NEP resistance and NPR-C resistance of the CNP analogs. U.S. Pat. No. 6,743,425 discloses substances for treating achondroplasia which activate NPR-B/GC-B and are peptides or low molecular weight compounds, including the C-type natriuretic peptides CNP-22 and CNP-53. PCT Publication No. WO 94/20534 discloses a chimera of CNP-22 and the 5-amino acid C-terminus of ANP designated as the vasonatrin peptide (VNP), a limited number of amino acid substitutions and cyclic chimeric peptides that result from formation of a disulfide or double bond.

Approaches for improving the half-life of other natriuretic peptide family members include decreasing the affinity of ANP for NPR-C (U.S. Pat. No. 5,846,932), utilizing pentapeptide antagonists of NPR-C (WO 00/61631), and co-administering NEP inhibitors such as thiorphan and candoxatril (Clin. Exp. Pharma. Physiol., 25: 986-991 (1997), Hyperten., 30: 184-190 (1997)). WO 2004/047871 describes conjugates of BNP and BNP variants to polyalkylene glycol moieties, sugar moieties, polysorbate moieties, polycationic moieties, and other hydrophilic polymer moieties that reportedly exhibit improved half-life in circulation and reportedly are useful for the treatment of acute congestive heart failure.

There have been no published reports, however, on a successful strategy for making CNP resistant to NEP while retaining its functionality.

SUMMARY OF THE INVENTION

The present invention relates to variants of C-type natriuretic peptide (CNP) which are useful in the treatment of bone-related disorders (e.g., achondroplasia) and vascular smooth muscle disorders. The invention encompasses CNP variants having increased serum half-life, e.g. as a result of reduced ability to bind to neutral endopeptidase (NEP), greater resistance to proteolysis by NEP and/or reduced affinity to the clearance natriuretic peptide receptor C(NPR-C), while retaining the functionality of CNP.

The wild-type sequence of CNP-22 (referred to herein as "wtCNP22" or "CNP22") is set forth below:

```
                                            (SEQ ID NO: 1)
(N-terminus) Gly₁-Leu₂-Ser₃-Lys₄-Gly₅-Cys₆-Phe₇-

Gly₈-Leu₉-Lys₁₀-Leu₁₁-Asp₁₂-Arg₁₃-Ile₁₄-

Gly₁₅-Ser₁₆-Met₁₇-Ser₁₈-Gly₁₉-Leu₂₀-Gly₂₁-

Cys₂₂.
```

Positions 6 to 22 of CNP22 form a cyclic domain by means of a disulfide bond between Cys6 and Cys22. The 17-amino acid cyclic structure has been shown to be important for binding of CNP to NPR-B (Schiller, Biochem. Biophys. Res. Commun., 138: 880-886 (1986)). The amino acid sequence of positions 6 to 22 of CNP22 is referred to herein as "CNP17" (SEQ ID NO: 2).

CNP is susceptible to NEP cleavage at a number of sites: Cys6-Phe7, Gly8-Leu9, Lys10-Leu11, Arg13-Ile14, Ser16-Met17 and Gly19-Leu20. In one embodiment, the invention encompasses a CNP variant that is (1) modified to increase its overall size or molecular weight, e.g., to a range from about 2.6 kDa or 2.8 kDa to about 4 kDa, 4.2 kDa, 4.4 kDa, 4.6 kDa, 4.8 kDa, 5 kDa, 5.2 kDa, 5.4 kDa, 5.6 kDa, 5.8 kDa, 6 kDa, 6.2 kDa, 6.4 kDa, or to about 7 kDa, 7.2 kDa or about 8.2 kDa, and/or (2) modified at certain amino acid positions to reduce its susceptibility to NEP cleavage at 1, 2, 3, 4, 5 or all 6 of the sites listed above. The size or molecular weight of the CNP variant can be increased by various means, e.g., by conjugating additional amino acids and/or other kinds of chemical (e.g., natural or synthetic polymeric) groups to the peptide sequence at, e.g., the N-terminus, the C-terminus and/or side chain(s), and/or by using natural amino acids, unnatural amino acids, and/or peptidomimetics with bulkier side chains. The CNP variant is optionally further conjugated to other functional or structural moieties. Optionally in combination with any of the embodiments described herein, mutation(s) (e.g., substitution(s), addition(s), and/or deletion(s)) may be introduced to certain position(s) of CNP22 to reduce the CNP variants' affinity to NPR-C. Further modifications may be made without affecting NEP resistance or CNP activity, e.g., conservative substitutions, or other modifications known in the art.

In one embodiment, the CNP variant is represented by the general formula: (x)-Gly$_1$-Leu$_2$-Ser$_3$-Lys$_4$-Gly$_5$-Cys$_6$-Phe$_7$-Gly$_8$-Leu$_9$-Lys$_{10}$-Leu$_{11}$-Asp$_{12}$-Arg$_{13}$-Ile$_{14}$-Gly$_{15}$-Ser$_{16}$-Met$_{17}$-Ser$_{18}$-Gly$_{19}$-Leu$_{20}$-Gly$_{21}$-Cys$_{22}$-(z) (SEQ ID NO: 5), wherein:

the CNP variant comprises one or more modified amino acids, which may result in modified peptide bonds (e.g., through use of peptide bond isosteres), at a position corresponding to one or more of the following CNP residues: Gly1, Lys4, Gly5, Cys6, Phe7, Gly8, Leu9, Lys10, Leu$_{11}$, Ile14, Gly15, Ser16, Met17, Gly19, Leu20 and Gly21; and (x) and (z) independently may be absent or may be an amino acid sequence derived from a natriuretic polypeptide (e.g., NPPC, ANP, BNP) or a non-natriuretic polypeptide (e.g., human serum albumin (HSA), IgG, etc.).

In an embodiment, the CNP variant includes: (1) a modification at an amino acid position corresponding to one of positions 6, 7 or 8 (Cys6, Phe7 or Gly8) of CNP22, (2) optionally deletion, addition and/or substitution of any or all of the amino acids at positions 1-5 (Gly1, Leu2, Ser3, Lys4, and Gly5) and (3) optionally up to 1, 2, 3, 4, 5, 6, 7, 8, 9 or 10 further modifications (deletions, additions and/or substitutions) at positions corresponding to positions 6-22, of which 1, 2, 3, 4, 5, 6, 7, 8, 9 or 10 may be conservative substitutions or other substitutions described herein or known in the art.

It is understood that a reference to a particular amino acid position by number (e.g. position 7 of CNP22) refers to the corresponding amino acid position in any CNP variant, even if the number of the position in that CNP variant has changed due to preceding insertions or deletions. For example, a reference to "position 7" or "Phe7" would mean the corresponding position 2 for a CNP variant in which the first five amino acids had been deleted. Similarly, a reference to "position 7" would mean the corresponding position 8 for a CNP variant in which one amino acid had been added to the N-terminus.

In any of the embodiments described herein, the CNP variant may be cyclized through a covalent bond between positions corresponding to 6 and 22 of CNP22. It is contemplated that the covalent bond is formed using any methods known in the art. In another embodiment, the CNP variant may be cyclized through a covalent bond formed between an amino acid at or toward the N-terminus and an amino acid at or toward the C-terminus (referred to as "terminal" amino acids for this purpose) of the peptide. In one embodiment, the covalent bond is formed between the side chains of the two terminal amino acids or the amino acids at positions corresponding to 6 and 22 of CNP22. In another embodiment, the covalent bond is formed between the side chain of one terminal amino acid and the terminal group of the other terminal amino acid, or between the terminal groups of each terminal amino acid. For example, head-to-tail, side chain-to-side chain, side chain-to-head, or side chain-to-tail bonds are possible for the covalent bond formed between the terminal amino acids or between the amino acids at positions corresponding to 6 and 22 of CNP22.

In one embodiment, the invention provides a CNP variant having reduced affinity to NEP, and/or greater resistance to cleavage by NEP and/or increased in vivo serum half-life, while retaining functionality of CNP (e.g., stimulation of cGMP production). NEP preferably recognizes substrates smaller than about 3 kDa, due to the limited size of its active site cavity (Oefner, J. Mol. Biol., 296: 341-349 (2000)). In an embodiment, the CNP variants are modified to increase their overall molecular weight to a range from about 2.6 or 2.8 kDa to about 4, 4.6, 5, 5.2, 5.8, 6, 6.4 or 7 kDa, e.g., by adding about 0.6 to about 5 kDa of amino acids, hydrophilic or water-soluble polymers, hydrophobic acids (including fatty acids), and/or carbohydrates. In specific exemplary embodiments, the CNP variants have a molecular weight between about 2.6 kDa and about 7 kDa, or between about 2.8 kDa and 6 kDa, or between about 2.8 kDa and about 5.8 kDa. In certain embodiments, at least about 0.6, 0.8, 1, 1.2, 1.4, 1.6 or 1.8 kDa, or up to 2, 2.2, 2.4, 2.6, 2.8, 3, 3.2, 3.4, 3.6, 3.8, 4, 4.2, 4.4, 4.6, 4.8 or 5 kDa are added, to increase the total molecular weight of the CNP variant, e.g., to a range from about 2.6 or 2.8 kDa up to about 4 kDa, 4.2 kDa, 4.4 kDa, 4.6 kDa, 4.8 kDa, 5 kDa, 5.2 kDa, 5.4 kDa, 5.6 kDa, 5.8 kDa, 6 kDa, 6.2 kDa, 7.2 kDa, 8.2 kDa or higher. In some embodiments, such CNP variants comprise an amino acid sequence at least about 70%, 75%. 80%, 85%, 90%, or 95% identical or homologous to amino acids 6-22 of CNP22. In other embodiments, such CNP variants comprise a substitution, insertion or deletion of 1, 2, 3, 4, 5, 6 or 7 amino acids with another natural or unnatural amino acid or peptidomimetic. While both conservative and non-conservative substitutions or insertions are envisioned at any position, introduction of modifications may commence, e.g., by conservative substitutions in regions that have been identified in the art as involved in CNP activity or NPR-B binding, while non-conservative substitutions may be made in those regions that have been previously shown to be tolerant of modification.

In another embodiment, the CNP variants comprise a CNP having an intact cyclized portion between Cys6 and Cys22, and N-terminal and/or C-terminal tails that contain about 1-40, 1-20, 5-40, 5-35, 10-35, 15-35, 5-31, 10-31, or 15-31 amino acids and are fragments derived from a CNP polypeptide and/or a non-CNP polypeptide. In an embodiment, such CNP variants have a molecular weight in a range from about 2.8 kDa to about 4, 4.6, 5, 5.2, 5.8, 6, 6.4 or 7 kDa. Non-limiting examples of such CNP variants include wild-type CNP22 or CNP22 with one or more amino acid substitutions (e.g., a K4R substitution), having an N-terminal and/or C-terminal extension derived from natriuretic peptide precursor sequences (e.g., ANP, BNP or CNP) from human or other species, a natriuretic peptide precursor C (NPPC) variant with amino acid substitutions, additions and/or deletions (e.g., the CNP variants may be truncations of CNP-53 which result in peptides with a molecular weight between about 2.8 kDa and 5.8 kDa), or other non-CNP polypeptides such as, e.g., serum albumin or IgG protein (e.g., the CNP variants may be CNP chimeras containing fragments of serum albumin or IgG from human or other species).

In one embodiment, CNP variants having a total mass characterized by the ranges described generally herein, e.g., from about 2.6 kDa or 2.8 kDa to about 6 or 7 kDa, designed for increased resistance to NEP degradation, are represented by the general formula:

(SEQ ID NO: 6)
(x)-Gly$_1$-Leu$_2$-Ser$_3$-(b)$_4$-Gly$_5$-Cys$_6$-Phe$_7$-Gly$_8$-Leu$_9$-

(h)$_{10}$-Leu$_{11}$-Asp$_{12}$-Arg$_{13}$-Ile$_{14}$-Gly$_{15}$-Ser$_{16}$-

Met$_{17}$-Ser$_{18}$-Gly$_{19}$-Leu$_{20}$-Gly$_{21}$-Cys$_{22}$-(z), wherein:

(x) is a synthetic or natural polymeric group, or a combination thereof, wherein a non-limiting example of a synthetic polymeric group is polyethylene glycol (PEG, also called polyethylene oxide (PEO)), and a non-limiting example of a natural polymeric group is an amino acid sequence containing from 1 to 35 amino acids and derived from NPPC or variants thereof with substitutions and/or deletions, ANP, BNP, or other non-CNP (poly)peptides such as, e.g., serum albumin, IgG, histine-rich glycoproteins, fibronectin, fibrinogen, zinc finger-containing polypeptides, osteocrin or fibroblast growth factor 2 (FGF2);

(z) may be absent or may be a synthetic or natural polymeric group, or a combination thereof, wherein a non-limiting example of a synthetic polymeric group is PEG, and a non-limiting example of a natural polymeric group is an amino acid sequence derived from a natriuretic polypeptide (e.g., NPPC, CNP, ANP or BNP) or non-natriuretic polypeptide (e.g., serum albumin or IgG); and (b) and (h) independently may each be the wild type Lys at that position or may be replaced with a conservative amino acid substitution or any natural or unnatural amino acid or peptidomimetic that does not have a reactive primary amine on a side chain, including but not limited to Arg, Gly, 6-hydroxy-norleucine, citrulline (Cit), Gln, Glu or Ser. In one embodiment, (b) is Arg. In another embodiment, for improved NEP resistance, (b) is not Gly. In yet another embodiment, (h) is not Arg.

Non-limiting examples of amino acid sequences derived from NPPC or variants thereof include:

Arg,

Glu-Arg,

Gly-Ala-Asn-Lys-Lys, (SEQ ID NO: 7)

Gly-Ala-Asn-Arg-Arg, (SEQ ID NO: 8)

Gly-Ala-Asn-Pro-Arg, (SEQ ID NO: 9)

Gly-Ala-Asn-Gln-Gln, (SEQ ID NO: 10)

Gly-Ala-Asn-Ser-Ser, (SEQ ID NO: 11)

Gly-Ala-Asn-Arg-Gln, (SEQ ID NO: 12)

Gly-Ala-Asn-Arg-Met, (SEQ ID NO: 13)

Gly-Ala-Asn-Arg-Thr, (SEQ ID NO: 14)

Gly-Ala-Asn-Arg-Ser, (SEQ ID NO: 15)

Ala-Ala-Trp-Ala-Arg-Leu-Leu-Gln-Glu-His-Pro-Asn-Ala, (SEQ ID NO: 16)

Ala-Ala-Trp-Ala-Arg-Leu-Leu-Gln-Glu-His-Pro-Asn-Ala-Arg, (SEQ ID NO: 17)

Asp-Leu-Arg-Val-Asp-Thr-Lys-Ser-Arg-Ala-Ala-Trp-Ala-Arg, (SEQ ID NO: 18)

Gln-Glu-His-Pro-Asn-Ala-Arg-Lys-Tyr-Lys-Gly-Ala-Asn-Lys-Lys, (SEQ ID NO: 19)

Gln-Glu-His-Pro-Asn-Ala-Arg-Lys-Tyr-Lys-Gly-Ala-Asn-Arg-Arg, (SEQ ID NO: 20)

Asp-Leu-Arg-Val-Asp-Thr-Lys-Ser-Arg-Ala-Ala-Trp-Ala-Arg-Leu-Leu-Gln-Glu-His-Pro-Asn-Ala-Arg-Lys-Tyr-Lys-Gly-Ala-Asn-Lys-Lys, (SEQ ID NO: 21)
and Asp-Leu-Arg-Val-Asp-Thr-Lys-Ser-Arg-Ala-Ala-Trp-Ala-Arg-Leu-Leu-Gln-Glu-His-Pro-Asn-Ala-Arg-Lys-Tyr-Lys-Gly-Ala-Asn-Arg-Arg. (SEQ ID NO: 22)

Non-limiting examples of amino acid sequences derived from non-CNP polypeptides such as, e.g., ANP, BNP, serum albumin and IgG include:

Ser-Leu-Arg-Arg-Ser-Ser; (SEQ ID NO: 23)

Asn-Ser-Phe-Arg-Tyr; (SEQ ID NO: 24)

Ser-Pro-Lys-Met-Val-Gln-Gly-Ser-Gly; (SEQ ID NO: 25)

Met-Val-Gln-Gly-Ser-Gly; (SEQ ID NO: 26)

Lys-Val-Leu-Arg-Arg-Tyr; (SEQ ID NO: 27)

Lys-Val-Leu-Arg-Arg-His; (SEQ ID NO: 28)

Gly-Gln-His-Lys-Asp-Asp-Asn-Pro-Asn-Leu-Pro-Arg; (SEQ ID NO: 29)

Gly-Val-Pro-Gln-Val-Ser-Thr-Ser-Thr; (SEQ ID NO: 30)

Gly-Glu-Arg-Ala-Phe-Lys-Ala-Trp-Ala-Val-Ala-Arg-Leu-Ser-Gln; (SEQ ID NO: 31)
and Gly-Gln-Pro-Arg-Glu-Pro-Gln-Val-Tyr-Thr-Leu-Pro-Pro-Ser. (SEQ ID NO: 32)

In an embodiment, the N-terminus and/or C-terminus of CNP22 or a variant thereof independently may be conjugated to an amino acid extension containing 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids. In one embodiment, the amino acid extension is derived from NPPC, CNP53, ANP or BNP. In a specific embodiment, the amino acid extension is Gln-Glu-His-Pro-Asn-Ala-Arg-Lys-Tyr-Lys-Gly-Ala-Asn-Lys-Lys (SEQ ID NO: 33). In a related embodiment, this 15-amino acid extension is added to the N-terminus to provide a CNP variant of the formula Gln-Glu-His-Pro-Asn-Ala-Arg-Lys-Tyr-Lys-Gly-Ala-Asn-Lys-Lys-Gly$_1$-Leu$_2$-Ser$_3$-(b)$_4$-Gly$_5$-Cys$_6$-Phe$_7$-Gly$_8$-Leu$_9$-(h)$_{10}$-Leu$_{11}$-Asp$_{12}$-Arg$_{13}$-Ile$_{14}$-Gly$_{15}$-Ser$_{16}$-Met$_{17}$-Ser$_{18}$-Gly$_{19}$-Leu$_{20}$-Gly$_{21}$-Cys$_{22}$-(z) (SEQ ID NO: 34).

In one embodiment, the CNP variants comprise wtCNP22 or a variant thereof (e.g., one having addition(s), deletion(s), and/or substitution(s) such as, e.g., a K4R substitution) (SEQ ID NO: 35) conjugated at the N-terminus and/or C-terminus to a hydrophilic polymer (e.g., PEG) to increase their overall molecular size to a range from about 2.6 kDa or 2.8 kDa to about 4, 5, 6 or 7 kDa. Such CNP variants are optionally further conjugated at the N-terminus and/or C-terminus to a polymeric group comprising, e.g., amino acids, carbohydrates, hydrophobic acids and/or phospholipids, a non-limiting example of which is an N-terminal amino acid extension containing 1 to 35, or 5 to 31, amino acids. In an embodiment, a hydrophilic polymeric (e.g., PEG) moiety of at least about 0.4, 0.6, 0.8, 1, 1.2, 1.4, 1.6 or 1.8 kDa, or up to 2, 2.2, 2.4, 2.6, 2.8, 3, 3.2, 3.4, 3.6, 3.8, 4, 4.2, 4.4, 4.6, 4.8 or 5 kDa, is added to the N-terminus and/or C-terminus of wtCNP22 or a variant thereof.

As shown herein, conjugation of a hydrophilic or water-soluble PEG (or PEO) polymer of about 0.6 kDa or more to CNP22 or variants thereof generally increases resistance to NEP cleavage markedly. However, addition of PEG, even as small as 0.6 kDa, to wtCNP22 may reduce CNP functionality (e.g., stimulation of cGMP signaling), and addition of greater than about 2 or 3 kDa of PEG to CNP22 or variants thereof may reduce CNP functional activity in a size-dependent manner. But CNP functionality (at least comparable to that of wtCNP22) is retained when a PEG (or PEO) polymer of about 0.6 kDa to about 1.2 kDa, or potentially to about 2 kDa, is conjugated to a CNP variant having an N-terminal amino acid extension in which at least one relatively large amino acid that may potentially be positively charged under physiological conditions (e.g., arginine) immediately precedes the position corresponding to Gly1 of CNP22, such as, e.g., GAN RR-CNP22(K4R) (CNP27(Arg4)) (SEQ ID NO: 36), GAN PR-CNP22(K4R) (CNP27(Pro4)) (SEQ ID NO: 37), ER-CNP22 (SEQ ID NO: 38), ER-CNP22(K4R) (SEQ ID NO: 39), R-CNP22 (SEQ ID NO: 40) and R-CNP22(K4R) (SEQ ID NO: 41).

Accordingly, in one embodiment, PEGylated CNP variants comprise at the N-terminus of CNP22 or a variant thereof (e.g., one having a K4R substitution) an amino acid extension containing at least 1, 2, 3, 4 or 5 amino acids, wherein the PEG polymer is conjugated to the N-terminus of the amino acid-extended CNP variant to result in a total mass characterized by the ranges described generally herein, e.g., from about 2.6 kDa or 2.8 kDa to about 6 or 7 kDa for increased resistance to NEP cleavage. In an embodiment, for enhanced CNP functionality, such pegylated, amino acid-extended CNP variants contain at least one relatively large natural or unnatural amino acid that may potentially be positively charged under physiological conditions, immediately preceding the position corresponding to Gly1 of CNP22. In a specific embodiment, the pegylated, amino acid-extended CNP variants contain at least one arginine residue immediately preceding the position corresponding to Gly1 of CNP22.

In addition to CNP variants conjugated at the N-terminus and/or C-terminus to a hydrophilic or water-soluble polymer such as, e.g., PEG (or PEO), the invention encompasses CNP variants conjugated to such a polymer at an internal site. For purposes of brevity here, PEG (or PEO) will be used as a representative example of a hydrophilic or water-soluble polymer. Various sites of PEGylation of a CNP variant are possible, including but not limited to: (1) PEGylation only at the N-terminus; (2) PEGylation only at the C-terminus; (3) PEGylation only at an internal site (e.g., Lys4); (4) PEGylation at both the N-terminus and the C-terminus; (5) PEGylation at the N-terminus and an internal site; and (6) PEGylation at the C-terminus and an internal site. For increased resistance to NEP degradation and retention of CNP functionality, in certain embodiments the total mass of PEGylated CNP variants is characterized by the ranges described generally herein, e.g., in the range from about 2.6 kDa or 2.8 kDa to about 4, 5, 6 or 7 kDa. In a particular embodiment, CNP17, CNP22, CNP37 (defined below) or variants thereof (including those having amino acid additions, substitutions and/or deletions) are PEGylated only at the N-terminus. In another embodiment, the CNP variants are PEGylated only at an internal site (e.g., Lys4). In yet another embodiment, the CNP variants are PEGylated at the N-terminus and an internal site (e.g., Lys4). In still another embodiment, for better functionality the CNP variants are not PEGylated at a site (e.g., Lys10) within the cyclic domain (corresponding to Cys6 to Cys22 of CNP22). To prevent PEGylation at an internal site, Lys4 and/or Lys10 can be substituted with a natural or unnatural amino acid or peptidomimetic that does not contain a reactive primary amino group on a side chain, such as, e.g., Gly, Ser, Arg, Asn, Gln, Asp, Glu or citrulline (Cit). In a particular embodiment, Lys4 and/or Lys10 are replaced with Arg. In another embodiment, Lys10 is not replaced with Arg.

The invention contemplates use of hydrophilic or water soluble polymers (e.g., PEG molecules) that may vary in type (e.g., homopolymer or copolymer; random, alternating or block copolymer; linear or branched; monodispersed or polydispersed), linkage (e.g., hydrolysable or stable linkage such as, e.g., amide, imine, aminal, alkylene, or ester bond), conjugation site (e.g., at the N-terminus and/or C-terminus, preferably not at any of the residues in the cyclized region of CNP (corresponding to residues 6-22 of CNP22)), and length (e.g., from about 0.2, 0.4 or 0.6 kDa to about 2, 3, 4 or 5 kDa). The hydrophilic or water-soluble polymer can be conjugated to the CNP peptide by means of N-hydroxy succinimide (NHS)- or aldehyde-based chemistry or other chemistry, as is known in the art. Such CNP variants can be generated using, e.g., wtCNP-22 (2.2 kDa), CNP-17 retaining only the cyclized region (residues 6-22) of wtCNP22, CNP variants having an amino acid extension at the N-terminus and/or C-terminus of CNP22, or variants with amino acid substitutions, additions and/or deletions, for example, CNP27(Arg4), CNP27(Pro4), R-CNP22, R-CNP22(K4R), ER-CNP22 and ER-CNP22 (K4R). In an embodiment, the PEG-CNP variants having a total mass characterized the ranges described generally herein, e.g., from about 2.6 kDa or 2.8 kDa to about 6 or 7 kDa, contain a monodispersed, linear PEG (or PEO) group conjugated at the N-terminus and/or C-terminus via NHS- or aldehyde-based chemistry, or a two-arm or three-arm branched PEG group conjugated at the N-terminus and/or C-terminus via NHS-based chemistry. The invention further contemplates negatively charged PEG-CNP variants designed for reduced renal clearance, including but not limited to carboxylated, sulfated and phosphorylated compounds.

In a related embodiment, the invention contemplates PEG-CNP conjugates comprising NHS- or aldehyde-based PEG of the formula $(CH_2CH_2O)_n$, wherein n is an integer from 12 to 50, and the PEG polymer is up to about 2.5 kDa in molecular weight. In a specific embodiment, n is 12 or 24. In an embodiment, the terminal hydroxyl group of the PEG polymer is capped with a non-reactive group. In a particular embodiment, the capping group is an alkyl group, e.g., a lower alkyl group such as methyl.

In an additional embodiment, the PEG polymers or derivatives thereof have a polymer number-average molecular weight in the range from about 0.4 kDa to about 2.5 kDa or from about 0.6 kDa to about 1.5 kDa.

In a further embodiment, the wtCNP or CNP variant peptide is conjugated to a moiety including, e.g., bisphosphonates, carbohydrates, hydrophobic acids (including fatty acids) or amino acid sequences. Such amino acid sequences include for example polyAsp or polyGlu useful in bone/cartilage targeting, or can be derived from bone proteins with elucidated bone-targeting domains or derivatives thereof, such as for example fusion proteins or peptide sequences of osteopontin, osteocalcin, sialoprotein, etc. In embodiments described herein where CNP22 or a variant thereof is attached to a bone- or cartilage-targeting moiety, such a moiety is designed to promote getting the modified CNP peptide to chondrocytes of bone growth plates, where the peptide can bind and activate NPR-B on the chondrocytes.

In another embodiment, the invention provides CNP variants with a peptide bond that is less susceptible to cleavage by peptidases including NEP. The invention encompasses a CNP variant comprising at least one modified residue at a site of endopeptidase cleavage. In one embodiment, the Cys6-Phe7 peptide bond (—C(=O)—NH—) at an NEP cleavage site in CNP can be replaced with anyone of the following peptide-bond isosteres:
 —CH$_2$—NH—,
 —C(=O)—N(R)—, where the amide group is alkylated with any of the following R groups: methyl, ethyl, n-propyl, isopropyl, cyclopropyl, n-butyl, isobutyl, sec-butyl or tert-butyl,
 —C(=O)—NH—CH$_2$—,
 —CH$_2$—S—,
 —CH$_2$—S(O)$_n$—, where n is 1 or 2,
 —CH$_2$—CH$_2$—,
 —CH=CH—,
 —C(=O)—CH$_2$—,
 —CH(CN)—NH—,
 —CH(OH)—CH$_2$—,
 —O—C(=O)—NH—, and
 —NHC(=O)NH—.

In another embodiment, Phe7 is substituted with its enantiomer D-Phe. In yet another embodiment, D-enantiomers are introduced to one or more, up to all 22, positions within wtCNP-22. In a further embodiment, a beta amino acid such as 3-amino-2-phenylpropionic acid is substituted for Phe7, which increases the length of the backbone while reducing the length of the side chain. In yet another embodiment, the invention contemplates Cys analogs at the Cys6 position including but not limited to homocysteine, penicillamine, 2-mercaptopropionic acid, and 3-mercaptopropionic acid.

Even in the presence of a NEP-resistant bond between Cys6 and Phe7, other peptide bonds can be hydrolyzed by NEP, including Gly8-Leu9, Lys10-Leu11, Arg13-Ile14, Ser16-Met17 and Gly19-Leu20. Accordingly, the invention encompasses CNP analogs containing peptide bond isosteres at multiple locations in the backbone of the CNP analogs. In one embodiment, CNP analogs or variants comprise modifications at more than one peptidase cleavage site. In a further embodiment, such variant comprises a CNP with substitutions at amino acid residues important in binding to the NEP active site, thereby increasing resistance to NEP degradation. One or more NEP-binding residues, including but not limited to Gly8, Gly15, Ser18, Gly19 and/or Gly21, are replaced with larger-size natural or unnatural amino acid residues to reduce affinity to the NEP active site. In yet another embodiment, one or more hydrophobic residues essential in NEP recognition, including but not limited to Phe7, Leu9, Leu11, Ile14, Met17 and Leu20, are substituted with natural or unnatural amino acids and/or peptidomimetics that decrease NEP binding. In yet another embodiment, one to five of the first five amino acids of CNP can be deleted or substituted with any other natural amino acids or unnatural amino acids or peptidomimetics, or one or more natural or unnatural amino acids or peptidomimetics can be added to any one or to all of the first five positions of CNP.

In a further embodiment, the CNP variants have a total mass characterized by the ranges described generally herein, e.g., from about 2.6 kDa or 2.8 kDa to about 6 or 7 kDa for increased resistance to NEP, and are represented by the formula:

(SEQ ID NO: 46)
(x)-Gly$_1$-Leu$_2$-Ser$_3$-(a)$_4$-Gly$_5$-(b)$_6$-(c)$_7$-(d)$_8$-(e)$_9$-

(f)$_{10}$-(g)$_{11}$-Asp$_{12}$-Arg$_{13}$-(h)$_{14}$-Gly$_{15}$-Ser$_{16}$-(i)$_{17}$-

Ser$_{18}$-Gly$_{19}$-(j)$_{20}$-Gly$_{21}$-Cys$_{22}$-(z), wherein:

(x) may be absent or may be selected from the group consisting of synthetic bone-targeting compounds such as, e.g., bisphosphonates; amino acid sequences useful in bone or cartilage targeting such as, e.g., polyAsp and polyGlu; amino acid sequences derived from bone proteins with elucidated bone-targeting domains, such as, e.g., fusion proteins or peptide sequences of osteopontin, osteocalcin, sialoprotein, etc.; polymeric or non-polymeric molecules that reduce renal clearance such as, e.g., charged PEG molecules; and extensions comprising, e.g., polymers (e.g., PEGs), carbohydrates, hydrophobic acids (including fatty acids), and/or amino acids, and wherein such amino acid extensions can contain, e.g., from 1 to 31, or 1 to 35, or 5 to 35, or 10 to 35, or 15 to 35 amino acid residues, and can be derived from NPPC, ANP, BNP, other non-CNP (poly)peptides such as, e.g., serum albumin or IgG, or variants of the aforementioned polypeptides having substitutions, additions and/or deletions, or combinations thereof;

(z) may be absent or may be selected from the group consisting of amino acid sequences useful in bone or cartilage targeting such as for example polyAsp and polyGlu, amino acid sequences from bone-targeting domains of bone proteins such as, e.g., osteopontin, osteocalcin and sialoprotein, and amino acid sequences derived from non-CNP (poly)peptides such as, e.g., ANP or BNP;

(a) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (a) is Arg;

(b) is selected from the group consisting of Cys and peptide-bond isosteres between Cys6 and Phe7 such as, e.g., Cys-CH$_2$—NH;

(c) is selected from the group consisting of L-Phe; D-Phe; 3-amino-2-phenylpropionic acid; N-alkylated derivatives of Phe, wherein the N-alkyl group is methyl, ethyl, n-propyl, isopropyl, cyclopropyl, n-butyl, isobutyl, sec-butyl or tert-butyl; and Phe analogs, wherein one or more ortho-, meta-, and/or para-positions of the benzene ring of the Phe analog are substituted with one or more substituents selected from the group consisting of halogen, hydroxyl, cyano, straight or branched C$_{1-6}$ alkyl, straight or branched C$_{1-6}$ alkoxy, straight or branched halo-$C_{1-6}$ alkyl, $C_{3-10}$ cycloalkyl, heterocyclyl, $C_{6-14}$ aryl and heteroaryl (examples include, but are not limited to, tyrosine, 3-chlorophenylalanine, 2,3-chloro-phenylalanine, 3-chloro-5-fluoro-phenylalanine, 2-chloro-6-fluoro-3-methyl-phenylalanine), or wherein the benzene ring of the Phe analog can be replaced with another aryl group (non-limiting examples include 1- and 2-naphthylalanine) or with a heteroaryl group (non-limiting examples include pyridylalanine, thienylalanine and furylalanine);

(d) is selected from the group consisting of Gly, tert-butyl-Gly (tBu-Gly), Thr, Ser, Val and Asn;

(e) is selected from the group consisting of Leu, Ser, Thr and peptide-bond isosteres such as, e.g., N-Me-Leu;

(f) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (f) is not Arg;

(g) is selected from the group consisting of Leu and peptide-bond isosteres such as, e.g., N-Me-Leu;

(h) is selected from the group consisting of Ile, tBu-Gly, and peptide-bond isosteres such as, e.g., N-Me-Ile;

(i) is selected from the group consisting of Met, Val, Asn, beta-Cl-Ala, 2-aminobutyric acid (Abu) and 2-amino-isobutyric acid (Aib); and (j) is selected from the group consisting of Leu, norleucine (Nle), homoleucine (Hleu), Val, tert-butyl-Ala (tBu-Ala), Ser, Thr, Arg, and peptide-bond isosteres such as, e.g., N-Me-Leu.

In one embodiment, the CNP variants comprise a modification at one or more of positions 6, 7, 8, 9, 10, 11, 13, 14, 16, 17, 19 and/or 20, and may optionally have modifications at any of the other positions disclosed herein.

In embodiments described herein where CNP22 or variants thereof can be attached to a hydrophobic acid, the CNP peptides can be attached to one or hydrophobic acids. Non-limiting examples of hydrophobic acids include straight-chain or branched, saturated or unsaturated $C_5$-$C_{12}$ carboxylic acids (e.g., pentanoic acid, heptanoic acid, etc.) and natural fatty acids. The hydrophobic acids can be attached to the N-terminus, the C-terminus, and/or the side chain of one or more amino acid residues. In one embodiment, the hydrophobic acids are conjugated to the N-terminus. In an embodiment, conjugation of CNP22 or a variant thereof to a hydrophobic acid is designed, inter alia, to promote non-specific interaction between the modified CNP peptide and serum albumin, thereby increasing the size of the CNP peptide and protecting it from cleavage by proteases such as, e.g., NEP. The interaction between the hydrophobic acid-conjugated CNP peptide and albumin is designed to be not too strong, so that the modified CNP peptide can diffuse through cartilage, get to chondrocytes of bone growth plates, and bind and activate NPR-B.

In a further embodiment, the invention provides CNP variants that in vitro stimulate the production of at least about 50% of the cGMP level produced under the same concentration of wtCNP22 (e.g., 1 uM), comprise at least one modified amino acid at position $(b)_6$, $(c)_7$ and/or $(d)_8$, and are represented by the general formula:

(SEQ ID NO: 47)
$(x)$-$Gly_1$-$Leu_2$-$Ser_3$-$(a)_4$-$Gly_5$-$(b)_6$-$(c)_7$-$(d)_8$-$(e)_9$-

$(f)_{10}$-$(g)_{11}$-$Asp_{12}$-$Arg_{13}$-$(h)_{14}$-$Gly_{15}$-$Ser_{16}$-$(i)_{17}$-

$Ser_{18}$-$Gly_{19}$-$(j)_{20}$-$Gly_{21}$-$Cys_{22}$-$(z)$, wherein:

(x) may be absent or may be a peptide sequence containing one to five amino acids which is derived from a natriuretic polypeptide (e.g. NPPC, CNP, ANP or BNP) or a non-natriuretic polypeptide as described herein (e.g., HSA, IgG, a bone-targeting protein, etc.);

(z) may be absent or may be selected from the group consisting of synthetic bone-targeting compounds such as, e.g., bisphosphonates; amino acid sequences useful in bone/cartilage targeting such as, e.g., polyAsp and polyGlu; bone proteins with bone-targeting domains and derivatives thereof, such as fusion proteins or peptides sequences of osteopontin, osteocalcin, and sialoprotein; molecules that reduce renal clearance, such as, e.g., charged PEGs; and molecules that increase resistance of CNP to NEP-mediated degradation, as described herein;

(a) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (a) is Arg;

(b) may be Cys or descarboxy cysteine, or the $(b)_6$-$(c)_7$ peptide bond (—C(=O)—NH—) may be replaced with any one of the following peptide bond isosteres:
—$CH_2$—NH—,
—C(=O)—N(R)—, where the amide group is alkylated with any of the following R groups: methyl, ethyl, n-propyl, isopropyl, cyclopropyl, n-butyl, isobutyl, sec-butyl or tert-butyl,
—C(=O)—NH—$CH_2$—,
—$CH_2$—S—,
—$CH_2$—S(O)$_n$—, where n is 1 or 2,
—$CH_2$—$CH_2$—,
—CH=CH—,
—C(=O)—$CH_2$—,
—CH(CN)—NH—,
—CH(OH)—$CH_2$—,
—O—C(=O)—NH—, or
—NHC(=O)NH—;

(c) is selected from the group consisting of L-Phe; D-Phe; 3-amino-2-phenylpropionic acid; peptide bond isosteres of Phe such as N-alkylated derivatives of Phe wherein the N-alkyl group is selected from the group consisting of methyl, ethyl, n-propyl, isopropyl, cyclopropyl, n-butyl, isobutyl, sec-butyl and tert-butyl; and Phe analogs, wherein one or more ortho-, meta-, and/or para-positions of the benzene ring of the Phe analog are substituted with one or more substituents selected from the group consisting of halogen, hydroxyl, cyano, straight or branched $C_{1-6}$ alkyl, straight or branched $C_{1-6}$ alkoxy, straight or branched halo-$C_{1-6}$ alkyl, $C_{3-10}$ cycloalkyl, $C_{6-14}$ aryl, heterocyclyl and heteroaryl (examples include, but are not limited to, tyrosine, 3-chlorophenylalanine, 2,3-chloro-phenylalanine, 3-chloro-5-fluoro-phenylalanine, 2-chloro-6-fluoro-3-methyl-phenylalanine), or wherein the benzene ring of the Phe analog can be replaced with another aryl group (non-limiting examples include 1- and 2-naphthylalanine) or with a heteroaryl group (non-limiting examples include pyridylalanine, thienylalanine and furylalanine);

(d) is selected from the group consisting of Gly, tert-butyl-Gly (tBu-Gly), Val, Ser, Thr and Asn;

(e) is selected from the group consisting of Leu, Ser, Thr and peptide-bond isosteres such as, e.g., N-Me-Leu;

(f) is any natural or unnatural amino acid or peptidomimetic that does not have a reactive primary amino group on a side chain, including but not limited to Arg, Gly, 6-hydroxy-norleucine, citrulline (Cit), Gln, Ser or Glu, wherein in one embodiment (f) is not Arg;

(g) is selected from the group consisting of Leu and peptide-bond isosteres such as, e.g., N-Me-Leu;

(h) is selected from the group consisting of Ile, tBu-Gly and peptide-bond isosteres such as, e.g., N-Me-Ile;

(i) is selected from the group consisting of Met, Val, Asn, beta-Cl-Ala, 2-aminobutyric acid (Abu) and 2-amino-isobutyric acid (Aib); and (j) is selected from the group consisting of Leu, norleucine (Nle), homoleucine (Hleu), Val, tert-butyl-Ala (tBu-Ala), Ser, Thr, Arg, and peptide-bond isosteres such as, e.g., N-Me-Leu.

In a further embodiment, the invention encompasses CNP variants that in vitro stimulate the production of at least about 50% of the cGMP level produced under the same concentration of wtCNP22 (e.g., 1 uM), have a total mass characterized by the ranges described generally herein, e.g., from about 2.6 kDa or 2.8 kDa to about 6 or 7 kDa for increased resistance to NEP degradation, and are represented by the general formula:

$$(x)-(y)-Cys_6-Phe_7-Gly_8-Leu_9-(h)_{10}-Leu_{11}-Asp_{12}-$$
$$Arg_{13}-Ile_{14}-Gly_{15}-Ser_{16}-Met_{17}-Ser_{18}-Gly_{19}-Leu_{20}-$$
$$Gly_{21}-Cys_{22}-(z),$$
(SEQ ID NO: 48)

wherein:

(x) is a synthetic or natural polymeric group, or a combination thereof, wherein a non-limiting example of a synthetic polymeric group is polyethylene glycol (PEG), and a non-limiting example of a natural polymeric group is an amino acid sequence containing from 1 to 35 amino acids and derived from NPPC or variants thereof with substitutions and/or deletions, ANP, BNP, or other non-CNP (poly)peptides such as, e.g., serum albumin, IgG, histine-rich glycoproteins, fibronectin, fibrinogen, zinc finger-containing polypeptides, osteocrin or FGF2;

(y) may be absent or may be one or more amino acids from $Gly_1-Leu_2-Ser_3-Lys_4-Gly_5$ (corresponding to positions 1 to 5 of CNP22) and/or substitutions at one or more of those positions using natural or unnatural amino acids (e.g., K4R substitution);

(h) may be the wild-type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (h) is not Arg; and (z) may be absent or may be a synthetic or natural polymeric group, or a combination thereof, wherein a non-limiting example of a synthetic polymeric group is PEG, and a non-limiting example of a natural polymeric group is an amino acid sequence derived from a natriuretic polypeptide (e.g., NPPC, CNP, ANP or BNP) or non-natriuretic polypeptide (e.g., serum albumin or IgG).

In an embodiment, (x), (y) and (z) together contain from about 10 to about 40, or from about 15 to about 35 amino acids. In another embodiment, (x) is an amino acid sequence comprising from 1 to 40 amino acids, or from 1 to 20 amino acids.

Further contemplated are CNP variants that in vitro stimulate the production of at least about 50% of the cGMP level produced under the same concentration of wtCNP22 (e.g., 1 uM), and comprise the sequence:

$$(y)-Cys_6-Phe_7-Gly_8-Leu_9-Lys_{10}-Leu_{11}-Asp_{12}-$$
$$Arg_{13}-Ile_{14}-Gly_{15}-Ser_{16}-Met_{17}-Ser_{18}-Gly_{19}-Leu_{20}-$$
$$Gly_{21}-Cys_{22},$$
(SEQ ID NO: 138)

wherein:

(y) comprises one or more amino acids selected from $Gly_1-Leu_2-Ser_3-Lys_4-Gly_5$ and/or substitutions at one or more of those positions using natural or unnatural amino acids (e.g., K4R substitution), and further comprises a hydrophilic or water soluble polymer of molecular weight from about 0.6 kDa to about 5 kDa. In an embodiment, the hydrophilic or water-soluble polymer is conjugated to the N-terminus of such amino acid-extended CNP variant. In a particular embodiment, the hydrophilic or water-soluble polymer is PEG (or PEO).

In yet another embodiment, the invention provides CNP variants that in vitro stimulate the production of at least about 50% of the cGMP level produced under produced under the same concentration of wtCNP22 (e.g. 1 uM), wherein the CNP variants comprise an N-terminal and/or C-terminal peptide extension containing from 1 to 15 amino acids, and are conjugated to a hydrophilic or water soluble polymer. In an embodiment, the peptide extension contains from 5 to 10 amino acids. In a specific embodiment, the peptide extension contains 5 amino acids. In another specific embodiment, the hydrophilic or water-soluble polymer is PEG (or PEO).

In a still further embodiment, the CNP variants of the invention in vitro stimulate the production of at least about 50% of the cGMP level produced under the same concentration of wtCNP22 (e.g. 1 uM), and comprise at least a 15 amino acid fragment derived from natriuretic peptide precursor C(NPPC), wherein the fragment is at least 70% homologous to a sequence from wild type NPPC containing the same number of amino acid residues.

In still another embodiment, the CNP variants have a total mass characterized by the ranges described generally herein, e.g., from about 2.6 kDa or 2.8 kDa to about 6 or 7 kDa for increased NEP resistance, and are represented by the formula:

$$(x)-(b)_6-(c)_7-(d)_8-(e)_9-(f)_{10}-(g)_{11}-Asp_{12}-Arg_{13}-$$
$$(h)_{14}-Gly_{15}-Ser_{16}-(i)_{17}-Ser_{18}-Gly_{19}-(j)_{20}-Gly_{21}-$$
$$Cys_{22}-(z),$$
(SEQ ID NO: 49)

wherein:

(x) may be absent (i.e., the N-terminus ends with an —NH$_2$ group) or may be selected from the group consisting of a sequence of 1, 2, 3, 4 or 5 amino acids from the peptide $Gly_1-Leu_2-Ser_3-Lys_4-Gly_5$; amino acid sequences useful in bone/cartilage targeting such as for example polyAsp or polyGlu; bone-targeting domains from bone proteins such as for example osteopontin, osteocalcin or sialoprotein; molecules that reduce renal clearance such as hydrophilic or water-soluble polymers, including but not limited to charged PEG molecules; and moieties comprising PEG, carbohydrates, hydrophobic acids, amino acids, or combinations thereof, wherein such moieties can be amino acid extensions including but not limited to amino acid sequences derived from NPPC or non-CNP (poly)peptides such as, e.g., BNP, ANP, serum albumin or IgG;

(z) may be absent or may be selected from the group consisting of amino acid sequences useful in bone/cartilage targeting such as for example polyAsp or polyGlu; amino acid sequences derived from bone-targeting proteins, such as for example osteopontin, osteocalcin or sialoprotein; and amino acid sequences derived from NPPC or non-CNP (poly) peptides, as described herein;

(b) is selected from the group consisting of Cys and peptide bond isosteres between Cys6 and Phe7 such as, e.g., Cys-CH$_2$—NH;

(c) is selected from the group consisting of L-Phe; D-Phe; 3-amino-2-phenylpropionic acid; N-alkylated derivatives of Phe, wherein the N-alkyl group is methyl, ethyl, n-propyl, isopropyl, cyclopropyl, n-butyl, isobutyl, sec-butyl or tert-butyl; and Phe analogs, wherein one or more ortho-, meta-, and/or para-positions of the benzene ring of the Phe analog are substituted with one or more substituents selected from the group consisting of halogen, hydroxyl, cyano, straight or branched $C_{1-6}$ alkyl, straight or branched $C_{1-6}$ alkoxy, straight or branched halo-$C_{1-6}$ alkyl, $C_{3-10}$ cycloalkyl, $C_{6-14}$ aryl, heterocyclyl and heteroaryl (examples include, but are not limited to, tyrosine, 3-chlorophenylalanine, 2,3-chloro-phenylalanine, 3-chloro-5-fluoro-phenylalanine, 2-chloro-6-fluoro-3-methyl-phenylalanine), or wherein the benzene ring of the Phe analog can be replaced with another aryl group (non-limiting examples include 1- and 2-naphthylalanine) or with a heteroaryl group (non-limiting examples include pyridylalanine, thienylalanine and furylalanine);

(d) is selected from the group consisting of Gly, tert-butyl-Gly (tBu-Gly), Val, Ser, Thr and Asn;

(e) is selected from the group consisting of Leu, Ser, Thr, and peptide-bond isosteres such as, e.g., N-Me-Leu;

(f) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (f) is not Arg;

(g) is selected from the group consisting of Leu and peptide-bond isosteres such as, e.g., N-Me-Leu;

(h) is selected from the group consisting of Ile, tBu-Gly and peptide-bond isosteres such as, e.g., N-Me-Ile;

(i) is selected from the group consisting of Met, Val, Asn, beta-Cl-Ala, 2-aminobutyric acid (Abu) and 2-amino-isobutyric acid (Aib); and (j) is selected from the group consisting of Leu, norleucine (Nle), homoleucine (Hleu), Val, tert-butyl-Ala (tBu-Ala), Ser, Thr, Arg, and peptide-bond isosteres such as, e.g., N-Me-Leu.

In a further embodiment, the CNP variants have a total mass characterized by the ranges described generally herein, e.g., from about 2.6 kDa or 2.8 kDa to about 6 or 7 kDa for increased NEP resistance, and are represented by the formula:

(SEQ ID NO: 50)
(x)-Gly$_1$-Leu$_2$-Ser$_3$-(a)$_4$-Gly$_5$-(b)$_6$-(c)$_7$-(d)$_8$-(e)$_9$-

(f)$_{10}$-(g)$_{11}$-Asp$_{12}$-Arg$_{13}$-(h)$_{14}$-(i)$_{15}$-Ser$_{16}$-(j)$_{17}$-

Ser$_{18}$-Gly$_{19}$-(k)$_{20}$-Gly$_{21}$-Cys$_{22}$-(z), wherein:

(x) and (z) independently may be absent or may be selected from the group consisting of synthetic bone-targeting compounds such as, e.g., bisphosphonates; amino acid sequences useful in bone/cartilage targeting such as for example polyAsp or polyGlu; amino acid sequences derived from bone-targeting domains of bone proteins and derivatives thereof, such as for example fusion proteins or peptide sequences of osteopontin, osteocalcin, sialoprotein, etc.; moieties that reduce renal clearance, including but not limited to hydrophilic or water-soluble polymers such as, e.g., charged PEG molecules; and moieties comprising, e.g., hydrophilic polymers (e.g., PEG), carbohydrates, hydrophobic acids, and/or amino acids;

(a) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (a) is Arg;

(b) is selected from the group consisting of Cys and peptide bond isosteres between Cys6 and Phe7 such as, e.g., Cys-CH$_2$—NH;

(c) is selected from the group consisting of L-Phe; D-Phe; 3-amino-2-phenylpropionic acid; N-alkylated derivatives of Phe, wherein the N-alkyl group is methyl, ethyl, n-propyl, isopropyl, cyclopropyl, n-butyl, isobutyl, sec-butyl or tert-butyl; and Phe analogs, wherein one or more ortho-, meta-, and/or para-positions of the benzene ring of the Phe analog are substituted with one or more substituents selected from the group consisting of halogen, hydroxyl, cyano, straight or branched $C_{1-6}$ alkyl, straight or branched $C_{1-6}$ alkoxy, straight or branched halo-$C_{1-6}$ alkyl, $C_{3-10}$ cycloalkyl, $C_{6-14}$ aryl, heterocyclyl and heteroaryl (examples include, but are not limited to, tyrosine, 3-chlorophenylalanine, 2,3-chloro-phenylalanine, 3-chloro-5-fluoro-phenylalanine, 2-chloro-6-fluoro-3-methyl-phenylalanine), or wherein the benzene ring of the Phe analog can be replaced with another aryl group (non-limiting examples include 1- and 2-naphthylalanine) or with a heteroaryl group (non-limiting examples include pyridylalanine, thienylalanine and furylalanine);

(d) is selected from the group consisting of Gly, tert-butyl-Gly, Thr, Ser, Val and Asn;

(e) is selected from the group consisting of Leu, Ser, Thr, and peptide bond isosteres such as, e.g., N-Me-Leu;

(f) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (f) is not Arg;

(g) is selected from the group consisting of Leu, Asn, and peptide bond isosteres such as, e.g., N-Me-Leu;

(h) is selected from the group consisting of Ile, tert-butyl-Gly (tBu-Gly), Asn, and peptide bond isosteres such as, e.g., N-Me-Ile;

(i) is selected from the group consisting of Gly, Arg, Ser and Asn;

(j) is selected from the group consisting of Met, Val, Asn, beta-Cl-Ala, 2-aminobutyric acid (Abu) and 2-amino-isobutyric acid (Aib); and (k) is selected from the group consisting of Leu, norleucine (Nle), homoleucine (Hleu), Val, tert-butyl-Ala (tBu-Ala), Arg, Thr, Ser, and peptide bond isosteres such as, e.g., N-Me-Leu.

In a further embodiment, the CNP variants can have amino acid substitution(s) at one or more of any of positions 1 to 22 of CNP22. In one embodiment, Gly1 is substituted with Arg or Glu. In another embodiment, Lys4 is replaced with Arg. In still another embodiment, Gly5 is substituted with Arg, Gln or Ser. In yet another embodiment, Gly15 is substituted with Ser, Asn, Arg or Cit. In a further embodiment, Gly19 is substituted with Ser, Arg or Asn. In yet another embodiment, Gly21 is substituted with Ser, Thr, or Arg.

In one embodiment, the CNP variant is selected from the group consisting of GLSKGC(CH₂NH)FGLKLDRIGSMS-GLGC (formed using descarboxy-Cys) (SEQ ID NO: 56), GLSKGC-(N-Me-Phe)-GLKLDRIGSMSGLGC (SEQ ID NO: 57), GLSKGC-(D-Phe)-GLKLDRIGSMSGLGC(SEQ ID NO:136), GLSKGCF-(tBuG)-LKLDRIGSMSGLGC (SEQ ID NO: 58), GLSKGC-(3-Cl-Phe)-GLKLDRIGSMS-GLGC (SEQ ID NO:137), and GLSKGC-[NHCH₂CH(Ph)CO]-GLKLDRIGSMSGLGC (formed using 3-amino-2-phenylpropionic acid) (SEQ ID NO: 59). In a further embodiment, a disulfide bond exists between Cys6, descarboxy-Cys or another sulfhydryl-containing cysteine analog at the Cys6 position, and Cys22 of any CNP variant described herein.

In another embodiment, the CNP variants contain an amino acid extension at the N-terminus and/or C-terminus of CNP22 or CNP17, including but not limited to:

```
                                          (SEQ ID NO: 4)
DLRVDTKSRAAWARLLQEHPNARKYKGANKKGLSKGCFGLKLDRIGSMSG
LGC (CNP-53);

(SEQ ID NO: 60)
QEHPNARKYKGANKKGLSKGCFGLKLDRIGSMSGLGC (CNP-37,
Analog BL);

(SEQ ID NO: 61)
AAWARLLQEHPNAGLSKGCFGLKLDRIGSMSGLGC (Analog CA);

(SEQ ID NO: 62)
AAWARLLQEHPNARGLSKGCFGLKLDRIGSMSGLGC (Analog CB);

(SEQ ID NO: 63)
DLRVDTKSRAAWARGLSKGCFGLKLDRIGSMSGLGC (Analog CC);

(SEQ ID NO: 40)
RGLSKGCFGLKLDRIGSMSGLGC;

(SEQ ID NO: 38)
ERGLSKGCFGLKLDRIGSMSGLGC;

(SEQ ID NO: 64)
GANQQGLSKGCFGLKLDRIGSMSGLGC;

(SEQ ID NO: 65)
GANRRGLSKGCFGLKLDRIGSMSGLGC;

(SEQ ID NO: 66)
GANPRGLSKGCFGLKLDRIGSMSGLGC;

(SEQ ID NO: 67)
GANSSGLSKGCFGLKLDRIGSMSGLGC;

(SEQ ID NO: 144)
GHKSEVAHRFKGANKKGLSKGCFGLKLDRIGSMSGLGC;
and (SEQ ID NO: 68)
SPKMVQGSG-CNP17-KVLRRH (Analog CD) (CNP17 having
N-terminal and C-terminal tails derived from BNP).
```

In a further embodiment, the CNP variants have a K4R substitution at position 4 of CNP22. Non-limiting examples of CNP(K4R) variants include:

```
                                        ((SEQ ID NO: 36)
GANRRGLSRGCFGLKLDRIGSMSGLGC (CNP27(Arg4)) (Analog
AY);

(SEQ ID NO: 37)
GANPRGLSRGCFGLKLDRIGSMSGLGC (CNP27(Pro4)) (Analog
CI);

(SEQ ID NO: 41)
RGLSRGCFGLKLDRIGSMSGLGC (Analog AZ);

(SEQ ID NO: 39)
ERGLSRGCFGLKLDRIGSMSGLGC (Analog BA);

(SEQ ID NO: 69)
GANQQGLSRGCFGLKLDRIGSMSGLGC (Analog CH);
and (SEQ ID NO: 70)
GANSSGLSRGCFGLKLDRIGSMSGLGC (Analog CG).
```

In one embodiment, CNP variants having a PEG (or PEO) moiety and an amino acid extension at the N-terminus contain arginine at the position immediately preceding the position corresponding to Gly1 of CNP22. Such PEGylated CNP variants are designed for increased resistance to NEP degradation, reduced binding to serum albumin, and enhanced CNP functional activity (e.g., activation of cGMP signaling). Non-limiting examples of such PEGylated CNP variants include PEO24-CNP27(Arg4), PEO12-CNP27(Arg4), PEO24-GANRR-CNP22, PEO12-GANRR-CNP22, PEO24-CNP27(Pro4), PEO12-CNP27(Pro4), PEO24-GANPR-CNP22, PEO12-GANPR-CNP22, PEO24-GANQQ-CNP22, PEO12-GANQQ-CNP22, PEO24-ER-CNP22(K4R), PEO12-ER-CNP22(K4R), PEO24-ER-CNP22, PEO12-ER-CNP22, PEO24-R-CNP22(K4R), PEO12-R-CNP22(K4R), PEO24-R-CNP22, and PEO12-R-CNP22, wherein PEO24 is a monodispersed 1.2 kDa PEG polymer and PEO12 is a monodispersed 0.6 kDa PEG polymer. In an embodiment, the PEG (or PEO) polymer is attached to the N-terminus of the CNP variants.

Additional CNP variants include, but are not limited to, derivatives of CNP37 having mutations at the furin cleavage site (underlined) to improve in vivo resistance to the furin protease and/or having glycine (underlined) preceding glutamine to prevent pyroglutamate formation, including but not limited to:

```
                                         (SEQ ID NO: 71)
GQEHPNARKYKGANPKGLSKGCFGLKLDRIGSMSGLGC (Analog
CS);

(SEQ ID NO: 72)
GQEHPNARKYKGANQKGLSKGCFGLKLDRIGSMSGLGC (Analog
CT);

(SEQ ID NO: 73)
GQEHPNARKYKGANQQGLSKGCFGLKLDRIGSMSGLGC (Analog
CU);

(SEQ ID NO: 74)
GQEHPNARKYKGANKPGLSKGCFGLKLDRIGSMSGLGC (Analog
CW);
and (SEQ ID NO: 75)
GQEHPNARKYKGANKKGLSKGCFGLKLDRIGSMSGLGC (Analog
DB).
```

In another embodiment, the CNP variants are chimera comprising CNP22 and an N-terminal peptide fragment, including but not limited to:

```
                                                         (SEQ ID NO: 76)
GHHSHEQHPHGANQQGLSKGCFGLKLDRIGSMSGLGC (Analog CQ) (histidine-rich
glycoprotein (HRGP) fragment-CNP22 chimera);

(SEQ ID NO: 77)
GAHHPHEHDTHGANQQGLSKGCFGLKLDRIGSMSGLGC (Analog CR) (HRGP
fragment-CNP22 chimera);

(SEQ ID NO: 78)
GHHSHEQHPHGANPRGLSKGCFGLKLDRIGSMSGLGC (Analog CX) (HRGP
fragment-CNP22 chimera);

(SEQ ID NO: 79)
GQPREPQVYTLPPSGLSKGCFGLKLDRIGSMSGLGC (Analog CF) (IgG1(Fc) fragment-
CNP22 chimera);

(SEQ ID NO: 80)
GQHKDDNPNLPRGANPRGLSKGCFGLKLDRIGSMSGLGC (Analog CY) (human serum
albumin (HSA) fragment-CNP22 chimera);

(SEQ ID NO: 81)
GERAFKAWAVARLSQGLSKGCFGLKLDRIGSMSGLGC (Analog CE) (HSA fragment-
CNP22 chimera);

(SEQ ID NO: 82)
FGIPMDRIGRNPRGLSKGCFGLKLDRIGSMSGLGC (Analog CZ) (osteocrin "NPR C
inhibitor" fragment-CNP22 chimera);
and
                                                         (SEQ ID NO: 83)
GKRTGQYKLGSKTGPGPKGLSKGCFGLKLDRIGSMSGLGC (Analog DA) (FGF2
"heparin-binding domain" fragment-CNP22 chimera).
```

In a further embodiment, the CNP variants are chimera comprising an N-terminal peptide fragment and CNP22 in which arginine is substituted for Lys4 of CNP22 ("CNP22 (K4R)"), including but not limited to:

```
                                                         (SEQ ID NO: 84)
GQPREPQVYTGANQQGLSRGCFGLKLDRIGSMSGLGC (Analog CK) (IgG1(Fc)
fragment-CNP22(K4R) chimera);

(SEQ ID NO: 85)
GVPQVSTSTGANQQGLSRGCFGLKLDRIGSMSGLGC (Analog CL) (HSA fragment-
CNP22(K4R) chimera)

(SEQ ID NO: 86)
GQPSSSSQSTGANQQGLSRGCFGLKLDRIGSMSGLGC (Analog CM) (fibronectin
fragment-CNP22(K4R) chimera);

(SEQ ID NO: 87)
GQTHSSGTQSGANQQGLSRGCFGLKLDRIGSMSGLGC (Analog CN) (fibrinogen
fragment-CNP22(K4R) chimera);

(SEQ ID NO: 88)
GSTGQWHSESGANQQGLSRGCFGLKLDRIGSMSGLGC (Analog CO) (fibrinogen
fragment-CNP22(K4R) chimera);
and
                                                         (SEQ ID NO: 89)
GSSSSSSSSSGANQQGLSRGCFGLKLDRIGSMSGLGC (Analog CP) (zinc finger
fragment-CNP22(K4R) chimera).
```

In yet another embodiment, the CNP variant may be a monomer or a dimer. In a related embodiment the monomers of dimeric CNP variants can be attached N-terminus to N-terminus via a linker or no linker, N-terminus to C-terminus via a linker or no linker, or C-terminus to C-terminus via a linker or no linker.

Chimera comprising IgG and CNP22 or a variant thereof are designed for, inter alia, increased resistance to NEP degradation and reduced binding to serum albumin. CNP chimera comprising a surface fragment of HSA are designed for, inter alia, reduced immunogenicity and reduced binding to serum albumin. HRGP-CNP22 and HRGP-CNP22(K4R) chimera containing a cationic, histidine-rich, non-lysine, non-arginine sequence at the N-terminus are designed for, inter alia, increased stability to proteases. Chimera containing an osteocrin fragment are designed to release, upon protease (e.g., furin) cleavage, the osteocrin fragment at bone growth plates, where the fragment would inhibit the clearance receptor NPR-C. With respect to chimera comprising an FGF2 heparin-binding fragment, heparin binding to the fragment is designed to protect the chimera from degradation, thereby providing a longer serum half-life. Chimera containing a fibronectin, fibrinogen, or zinc-finger fragment are designed for reduced binding to serum albumin, among other advantageous features.

Not intending to be bound by theory, a CNP variant of molecular weight from about 2.6 kDa or 2.8 kDa to about 6 or 7 kDa which has increased resistance to NEP degradation and has similar or improved functionality (e.g., binding to NPR-B and stimulation of cGMP signaling) as compared to wtCNP22, may be more effective if it does not bind tightly to plasma proteins such as serum albumin. A CNP variant that does not bind tightly to plasma proteins (e.g., serum albumin) may be more effective in diffusing through cartilage, getting to chondrocytes of bone growth plates, and binding to and activating NPR-B for cGMP signaling. In one embodiment, CNP variants designed for reduced binding to plasma proteins (e.g., serum albumin) are chimeras comprising CNP22 or a variant thereof and a peptide fragment from IgG. In another embodiment, CNP variants designed for reduced binding to plasma proteins are chimeras comprising CNP22 or CNP22(K4R) and a fragment from a polypeptide (e.g., IgG, HSA, fibronectin, fibrinogen, a zinc finger-containing polypeptide, etc.). In yet another embodiment, CNP variants designed for reduced binding to plasma proteins comprise CNP22 or a variant thereof conjugated to a hydrophilic or water-soluble polymer. In one embodiment, the hydrophilic or water-soluble polymer is PEG (or PEO). In another embodiment, the hydrophilic or water-soluble polymer (e.g., PEG) is functionalized with one or more functional groups that impart a negative charge to the polymer under physiological conditions, such as, e.g, carboxyl, sulfate or phosphate groups, or a combination thereof.

In any of the embodiments disclosed herein, the CNP variants may have substantially the same or better biological activity than wild-type CNP22. For example, the CNP variants may retain at least 50%, 60%, 70%, 80%, 90%, 95% or more of the activity of wild-type CNP22, or may have greater activity than CNP22, e.g., with respect to interaction with NPR-B (GC-B) to stimulate the generation of cGMP. Alternatively, or in addition, the CNP variants may retain at least 50%, 60%, 70%, 80%, 90%, 95% or more of the activity of wild-type CNP22, or may have greater activity than CNP22, with respect to regulating endochondral bone growth and chondrocyte activity, including but not limited to chondrocyte proliferation, chondrocyte differentiation, inhibition of the mitogen activated protein (MAP) kinase/MEK (Raf-1) kinase signaling pathway, and promoting endochondral ossification. In any of the embodiments described herein, the CNP variants may comprise an amino acid sequence that is at least 40%, 50%, 60%, 70%, 80%, 90%, 95% or more identical or homologous to amino acids 6-22 or 1-22 of wild-type CNP22.

In a further embodiment, the invention provides variants of CNP22 having less affinity to the NPR-C clearance receptor while retaining the ability to bind and activate NPR-B. The present invention encompasses variants that were, or can be, generated from a homology-based structural model of the NPR-B/CNP complex as described in the Detailed Description. In another embodiment, the CNP variants have substitution(s) at one or more Gly sites at positions 1, 5, 8, 15, 19 and 21, to reduce conformational flexibility, which may increase their specificity for binding to NPR-B over NPR-C. Variants of CNP having potentially reduced affinity to the NPR-C include but are not limited to those having one or more of the following substitutions: G1R, G1E, G5R, G5Q, G5S, F7Y, G8T, GBS, G8V, G8N, L9S, L9T, K10Cit, K10Q, K10S, I14N, G15R, G15S, G15N, G15Cit, S16Q, M17V, M17N, G19S, G19R, G19N, L20V, L20R, L20T, L20S, G21S, G21T and G21R.

In yet another embodiment, the CNP variants have a modification and/or substitution at one or more of positions 5, 7, 8, 9, 10, 14, 15, 16, 17, 19, 20 and 21, and may optionally have modifications and/or substitutions at any of the other positions disclosed herein. In a further embodiment, the CNP variants can optionally have conjugation(s) or extension(s), e.g., at the N- and/or C-terminus to facilitate bone/cartilage targeting, reduce renal clearance, and/or increase resistance to NEP degradation. Such conjugation(s) or extension(s) can comprise molecules or sequences formed or derived from, e.g., polyAsp, polyGlu, bone- or cartilage-targeting peptides, osteopontin, osteocalcin, sialoprotein, PEGs, carbohydrates, hydrophobic acids, NPPC or non-CNP (poly)peptides, or combinations thereof.

In still another embodiment, the CNP variants are prepared by standard solid-phase peptide synthesis methods with natural or unnatural amino acid(s) or peptidomimetic(s) being substituted and/or added where appropriate. In a further embodiment, PEGylation of the CNP variants occurs following, or part of, peptide synthesis with the conjugation reaction being performed by NHS- or aldehyde-based chemistry or other chemistry known in the art. In another embodiment, the CNP variants comprise a disulfide bond. In a related embodiment, the disulfide bond forms a cyclic peptide. In a particular embodiment, the disulfide bond is formed between cysteine residues at positions corresponding to positions 6 and 22 of CNP22.

It is further contemplated that the CNP variants can be conjugated to a hydrophobic polymeric or non-polymeric moiety, such as, e.g., heptanoic acid, pentanoic acid, or fatty acids. The hydrophobic moiety can be conjugated to the side chain of an amino acid residue, including but not limited to a lysine, a serine, a cysteine or a threonine, or can be attached to the N-terminus and/or C-terminus of the CNP variant.

In an embodiment, the CNP variants as described herein have a pI in the range from about 8 to about 10.5 or from about 8.5 to about 10.

In a further embodiment, the invention provides a pharmaceutical composition comprising a CNP variant, optionally another biologically active agent, and optionally a pharmaceutically acceptable excipient, carrier or diluent. In some embodiments, the compositions are sterile pharmaceutical compositions suitable for parenteral injection. In some embodiments, the compositions comprise substantially pure CNP variant, e.g. at least about 90% or 95% pure. In some embodiments, the compositions contain less than about 5%, 4%, 3%, 2%, 1% or 0.5% contaminants, such as other human proteins, porcine proteins, or CNP53 or fragments thereof (other than the desired CNP variant).

CNP variants of the invention advantageously retain CNP activity and exhibit increased serum half-life. Retention of CNP activity can be shown, for example, as retention of desired in vivo biological effect, or retention of at least about 50% of the cGMP stimulating activity of CNP22, under the same concentration (e.g., 1 uM of CNP peptide or greater than the ED80). In some embodiments, CNP variants exhibit at least about 1.5-fold, 2-fold, 3-fold, 4-fold, 5-fold, 10-fold, 15-fold, 20-fold, 25-fold, 30-fold, 35-fold or 40-fold increase in serum half-life compared to CNP22.

In yet another embodiment, the invention provides methods of treating conditions or disorders responsive to CNP, comprising administering a therapeutically effective amount of a CNP variant or a composition comprising the same to a subject in need thereof. In one embodiment, disorders responsive to CNP are disorders of bone growth, including but not limited to skeletal dysplasias and inherited skeletal malformations such as disorders associated with fibroblast growth factor receptor 3 (FGFR-3) mutations. In a specific embodiment, the disorder associated with FGFR-3 mutation(s) is achondroplasia. In another embodiment, the disorders responsive to CNP are disorders associated with vascular smooth muscle cells and tissues. In a further embodiment, the CNP variants are useful for increasing the size of the growth plate of a bone (e.g., a limb bone). In another embodiment, the CNP variants are useful for elongating a bone or increasing long bone growth. In still another embodiment, the CNP variants are useful for enhancing matrix production, proliferation and differentiation of chondrocytes.

DETAILED DESCRIPTION OF THE INVENTION

Figure 1:
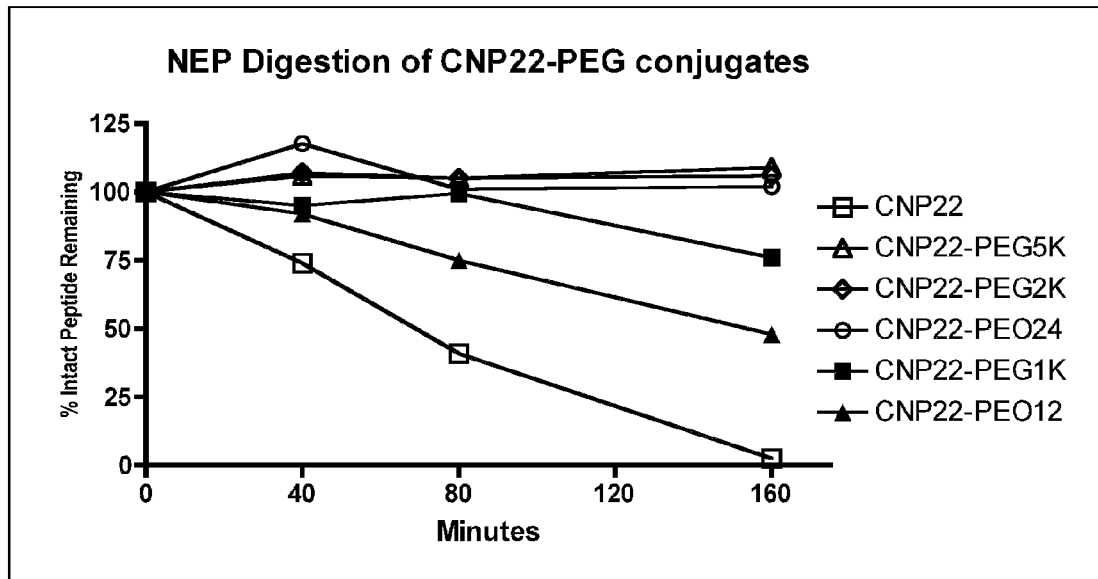
FIG. 1 shows the degree of resistance of N-terminal PEGylated CNP22 conjugates to neutral endopeptidase (NEP) in vitro.

The present invention relates to novel variants of CNP having reduced affinity to NEP and/or NPR-C, and reduced susceptibility to cleavage by NEP and/or clearance by NPR-C, pharmaceutical compositions comprising such CNP variants, and methods of using such CNP variants to treat disorders responsive to CNP, including but not limited to bone-related disorders such as achondroplasia and disorders associated with vascular smooth muscle cells and tissues.

A. Definitions

Unless otherwise stated, the following terms used in this application, including the specification and claims, have the definitions given below.

As used in the specification and the appended claims, the indefinite articles "a" and "an" and the definite article "the" include plural as well as singular referents unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, or 0.05% of a given value or range.

Definition of standard chemistry terms may be found in reference works, including Carey and Sundberg, Advanced Organic Chemistry, $3^{rd}$ Edition, Vols. A and B (Plenum Press, New York 1992). The practice of the present invention employs, unless otherwise indicated, conventional methods of synthetic organic chemistry, mass spectrometry, preparative and analytical chromatography, protein chemistry, biochemistry, recombinant DNA technology and pharmacology, within the skill of the art. See, e.g., T. E. Creighton, Proteins: Structures and Molecular Properties (W.H. Freeman and Company, 1993); A. L. Lehninger, Biochemistry (Worth Publishers, Inc., $4^{th}$ Edition, 2004); Sambrook, et al., Molecular Cloning: A Laboratory Manual ($2^{nd}$ Edition, 1989); Methods In Enzymology (S. Colowick and N. Kaplan eds., Academic Press, Inc.); Remington's Pharmaceutical Sciences, $18^{th}$ Edition (Easton, Pa.: Mack Publishing Company, 1990).

All publications, patents and patent applications cited herein, whether supra or infra, are hereby incorporated by reference in their entirety.

The following amino acid abbreviations are used throughout the text:

Alanine: Ala (A) Arginine: Arg (R)
Asparagine: Asn (N) Aspartic acid: Asp (D)
Cysteine: Cys (C) Glutamine: Gln (Q)
Glutamic acid: Glu (E) Glycine: Gly (G)
Histidine: His (H) Isoleucine: Ile (I)
Leucine: Leu (L) Lysine: Lys (K)
Methionine: Met (M) Phenylalanine: Phe (F)
Proline: Pro (P) Serine: Ser (S)
Threonine: Thr (T) Tryptophan: Trp (W)
Tyrosine: Tyr (Y) Valine: Val (V)

"Polypeptide" and "protein" refer to a polymer composed of amino acid residues, related naturally occurring structural variants, and synthetic non-naturally occurring analogs thereof, linked via peptide bonds or peptide bond isosteres. Synthetic polypeptides can be synthesized, for example, using an automated polypeptide synthesizer. The terms "polypeptide" and "protein" are not limited to a minimum length of the product. The term "protein" typically refers to large polypeptides. The term "peptide" typically refers to short polypeptides. Thus, peptides, oligopeptides, dimers, multimers, and the like, are included within the definition. Both full-length proteins and fragments thereof are encompassed by the definition. The terms "polypeptide" and "protein" also include postexpression modifications of the polypeptide or protein, for example, glycosylation, acetylation, phosphorylation and the like. Furthermore, for purposes of the present invention, a "polypeptide" can include "modifications," such as deletions, additions, substitutions (which may be conservative in nature or may include substitutions with any of the 20 amino acids that are commonly present in human proteins, or any other naturally or non-naturally-occurring or atypical amino acids), and chemical modifications (e.g., addition of or substitution with peptidomimetics), to the native sequence. These modifications may be deliberate, as through site-directed mutagenesis, or through chemical modification of amino acids to remove or attach chemical moieties, or may be accidental, such as through mutations arising with hosts that produce the proteins or through errors due to PCR amplification.

Conventional notation is used herein to portray polypeptide sequences: the left-hand end of a polypeptide sequence is the amino-terminus; the right-hand end of a polypeptide sequence is the carboxyl-terminus.

"Conservative substitution" refers to substitution of an amino acid in a polypeptide with a functionally, structurally or chemically similar natural or unnatural amino acid. In one embodiment, the following groups each contain natural amino acids that are conservative substitutions for one another:

(1), Alanine (A) Serine (S), Threonine (T);
(2) Aspartic acid (D), Glutamic acid (E);
(3) Asparagine (N), Glutamine (Q);
(4) Arginine (R), Lysine (K);
(5) Isoleucine (I), Leucine (L), Methionine (M), Valine (V); and
(6) Phenylalanine (F), Tyrosine (Y), Tryptophan (W).

In another embodiment, the following groups each contain natural amino acids that are conservative substitutions for one another:

(1) Glycine (G), Alanine (A);
(2) Aspartic acid (D), Glutamic acid (E);
(3) Asparagine (N), Glutamine (Q);
(4) Arginine (R), Lysine (K);
(5) Isoleucine (I), Leucine (L), Methionine (M), Valine (V), Alanine (A);
(6) Phenylalanine (F), Tyrosine (Y), Tryptophan (W); and
(7) Serine (S), Threonine (T), Cysteine (C).

In a further embodiment, amino acids may be grouped as set out below.

(1) hydrophobic: Met, Ala, Val, Leu, Ile, Phe, Trp;
(2) neutral hydrophilic: Cys, Ser, Thr, Asn, Gln;
(3) acidic: Asp, Glu;
(4) basic: H is, Lys, Arg;
(5) residues that influence backbone orientation: Gly, Pro; and
(6) aromatic: Trp, Tyr, Phe, His.

In one embodiment, the peptides or polypeptide described herein are generated via recombinant means, using a polynucleotide encoding a CNP variant. The invention thus encompasses polynucleotides encoding any of the CNP variants described herein, host cells or vectors comprising such polynucleotides, optionally linked to expression control sequences, and methods of using such polynucleotides, vectors or host cells to produce CNP variants of the invention. CNP variants expressed by such polynucleotides may be produced by methods including growing host cells in culture medium under conditions suitable for expression of the polynucleotide encoding a CNP variant, and isolating the expression product from the host cells or culture medium. Actual expression products may vary slightly from the encoded protein product depending on any post-translational processing.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), the nucleotide sequence also encompasses an RNA sequence (i.e., A, U, G, C) in which "U" replaces "T." "cDNA" refers to a DNA that is complementary or identical to an mRNA, in either single stranded or double stranded form.

"Expression control sequence" refers to a nucleotide sequence that regulates the expression of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well.

"Chimera" as used herein refers to a polynucleotide or polypeptide comprising at least two heterologous polynucleotide or polypeptide sequences (i.e. derived from different sources or not associated with each other as a naturally-occurring sequence) which are attached or linked together using techniques commonly known in the art, e.g., recombinant expression or chemical crosslinking.

The terms "identical" and percent "identity," in the context of two or more polynucleotide or polypeptide sequences, refer to two or more sequences or subsequences that are the same or have a specified percentage of nucleotides or amino acid residues that are the same, when compared and aligned for maximum correspondence, as measured using one of the following sequence comparison algorithms or by visual inspection.

The phrase "substantially homologous" or "substantially identical" in the context of two nucleic acids or polypeptides, generally refers to two or more sequences or subsequences that have at least 40%, 50%, 60%, 70%, 80%, 90%, 95%, or 98% nucleotide or amino acid residue identity, when compared and aligned for maximum correspondence, as measured using one of the following sequence comparison algorithms or by visual inspection. In certain embodiments, the substantial identity exists over regions of the sequences that are at least about 25, 50, 100 or 150 residues in length. In another embodiment, the sequences are substantially identical over the entire length of either or both comparison biopolymers.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math., 2: 482 (1981), by the homology alignment algorithm of Needleman & Wunsch, J. Mol. Biol., 48: 443 (1970), by the search for similarity method of Pearson & Lipman, Proc. Natl. Acad. Sci. USA, 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection. One example of a useful algorithm is PILEUP, which uses a simplification of the progressive alignment method of Feng & Doolittle, J. Mol. Evol., 35: 351-360 (1987) and is similar to the method described by Higgins & Sharp, CABIOS, 5: 151-153 (1989). Another algorithm useful for generating multiple alignments of sequences is Clustal W (Thompson et al., Nucleic Acids Research, 22: 4673-4680 (1994)). An example of algorithm that is suitable for determining percent sequence identity and sequence similarity is the BLAST algorithm (Altschul et al., J. Mol. Biol., 215: 403-410 (1990); Henikoff & Henikoff, Proc. Natl. Acad. Sci. USA, 89: 10915 (1989); Karlin & Altschul, Proc. Natl. Acad. Sci. USA, 90: 5873-5787 (1993)). Software for performing BLAST analyses is publicly available through the National Center for Biotechnology Information.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described herein.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. In one embodiment, a substantially pure composition means that the species of interest comprises at least about 70%, 75%, 80%, 85%, 90%, 95%, 98% or more of the macromolecular species present in the composition on a molar or weight basis. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition. In an embodiment, the compounds of the invention are substantially pure or isolated. In another embodiment, the compounds of the invention are substantially pure or isolated with respect to the macromolecular starting materials used in their synthesis. In yet another embodiment, the pharmaceutical compositions of the invention comprise a substantially pure or isolated CNP variant admixed with one or more pharmaceutically acceptable excipients, carriers or diluents, and optionally with another biologically active agent.

"Naturally occurring" as applied to an object refers to the fact that the object can be found in nature. For example, a polypeptide or polynucleotide sequence that is present in an organism (including viruses) and which has not been intentionally modified by man in the laboratory is naturally occurring. In one embodiment, a "naturally occurring" substance is of human origin.

"Wild-type" (wt) is a term referring to the natural form, including sequence, of a polynucleotide, polypeptide or protein in a species. A wild-type form is distinguished from a mutant form of a polynucleotide, polypeptide or protein arising from genetic mutation(s).

In one embodiment, a first polypeptide that is an "analog" or "variant" or "derivative" of a second polypeptide is a polypeptide having at least about 50%, 60% or 70% sequence homology, but less than 100% sequence homology, with the second polypeptide. Such analogs, variants or derivatives may be comprised of non-naturally occurring amino acid residues, including without limitation, homoarginine, ornithine, penicillamine, and norvaline, as well as naturally occurring amino acid residues. Such analogs, variants or derivatives may also be composed of one or a plurality of D-amino acid residues, and may also contain peptidomimetics or peptide bond isosteres such as non-peptide linkages between two or more amino acid or peptidomimetic residues. In another embodiment, a first polypeptide is an "analog", "variant" or "derivative" of a second polypeptide if the first polypeptide is not a known cleavage product of the second polypeptide or is not a known precursor of the second polypeptide, even if the first polypeptide has 100% sequence homology to the second polypeptide or has a wild-type sequence.

In an embodiment, the term "derived from" as used herein refers to a polypeptide or peptide sequence that is based on a wild type or naturally occurring polypeptide or peptide sequence and can have one or more deletions, additions, and/or substitutions with natural amino acids, unnatural amino acids or peptidomimetics. In one embodiment, the derivative sequence shares at least about 40%, 50%, 60% or 70%, but less than 100%, sequence similarity to the wild-type or naturally occurring sequence. In another embodiment, the derivative may be a fragment of a polypeptide, wherein the fragment is substantially homologous (e.g., at least about 70%, 75%, 80%, 85%, 90%, or 95% homologous) to the wild-type polypeptide over a length of at least about 5, 10, 15, 20, 25, 30, 35, 40, 45 or 50 amino acids. In still another embodiment, a polypeptide is "derived from" a wild-type polypeptide if it has a moiety (e.g., a polymer such as, e.g., PEG) attached to it which is not present on the wild-type polypeptide, even if both polypeptides share 100% homology in their amino acid sequence.

As used herein, an "NPPC-derived" polypeptide refers to a polypeptide derived from the natriuretic peptide precursor C(NPPC) polypeptide, which is a single chain 126-amino acid pre-pro polypeptide, and which upon cleavage ultimately results in wtCNP22. Removal of the signal peptide from NPPC yields pro-CNP, and further cleavage by the endoprotease furin generates an active 53-amino acid peptide (CNP-53), which is secreted and cleaved again by an unknown enzyme to produce the mature 22-amino acid peptide (CNP, or CNP-22). Therefore, CNP22 itself is an "NPPC-derived" polypeptide by virtue of being derived from NPPC. In one embodiment, an NPPC-derived polypeptide is at least about 40%, 50%, 60%, 70%, 75%, 80%, 85%, 90%, or 95% homologous to the wild type NPPC over the same number of amino acid residues. It is further contemplated that an NPPC-derived peptide may comprise from about 1 to about 53, or 1 to 37, or 1 to 35, or 1 to 31, or 1 to 27, or 1 to 22, or 10 to 35, or about 15 to about 37 residues of the NPPC polypeptide. In one embodiment, an NPPC-derived peptide may comprise a sequence of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 amino acids derived from the NPPC polypeptide.

The term "effective amount" means a dosage sufficient to produce a desired result on a health condition, pathology, or disease of a subject or for a diagnostic purpose. The desired result may comprise a subjective or objective improvement in the recipient of the dosage. "Therapeutically effective amount" refers to that amount of an agent effective to produce the intended beneficial effect on health. An appropriate "effective" amount in any individual case may be determined by one of ordinary skill in the art using routine experimentation. It will be understood that the specific dose level and frequency of dosage for any particular patient may be varied and will depend upon a variety of factors, including the activity of the specific compound employed; the bioavailability, metabolic stability, rate of excretion and length of action of that compound; the mode and time of administration of the compound; the age, body weight, general health, sex, and diet of the patient; and the severity of the particular condition.

"Treatment" refers to prophylactic treatment or therapeutic treatment or diagnostic treatment. In certain embodiments, "treatment" refers to administration of a compound or composition to a subject for therapeutic, prophylactic or diagnostic purposes.

A "prophylactic" treatment is a treatment administered to a subject who does not exhibit signs of a disease or exhibits only early signs of the disease, for the purpose of decreasing the risk of developing pathology. The compounds or compositions of the invention may be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective. The compounds of the invention may also be given as a therapeutic treatment or for diagnosis.

"Diagnostic" means identifying the presence, extent and/or nature of a pathologic condition. Diagnostic methods differ in their specificity and selectivity. While a particular diagnostic method may not provide a definitive diagnosis of a condition, it suffices if the method provides a positive indication that aids in diagnosis.

"Pharmaceutical composition" refers to a composition suitable for pharmaceutical use in subject animal, including humans and mammals. A pharmaceutical composition comprises a therapeutically effective amount of a CNP variant, optionally another biologically active agent, and optionally a pharmaceutically acceptable excipient, carrier or diluent. In an embodiment, a pharmaceutical composition encompasses a composition comprising the active ingredient(s), and the inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the invention and a pharmaceutically acceptable excipient, carrier or diluent.

"Pharmaceutically acceptable carrier" refers to any of the standard pharmaceutical carriers, buffers, and the like, such as a phosphate buffered saline solution, 5% aqueous solution of dextrose, and emulsions (e.g., an oil/water or water/oil emulsion). Non-limiting examples of excipients include adjuvants, binders, fillers, diluents, disintegrants, emulsifying agents, wetting agents, lubricants, glidants, sweetening agents, flavoring agents, and coloring agents. Suitable pharmaceutical carriers, excipients and diluents are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration).

A "pharmaceutically acceptable salt" is a salt that can be formulated into a compound for pharmaceutical use, including but not limited to metal salts (e.g., sodium, potassium, magnesium, calcium, etc.) and salts of ammonia or organic amines.

By "pharmaceutically acceptable" or "pharmacologically acceptable" is meant a material that is not biologically or otherwise undesirable, i.e., the material may be administered to an individual without causing any undesirable biological effects or without interacting in a deleterious manner with any of the components of the composition in which it is contained or with any components present on or in the body of the individual.

The term "unit dosage form" refers to physically discrete units suitable as unitary dosages for human and animal subjects, each unit containing a predetermined quantity of a compound of the invention calculated in an amount sufficient to produce the desired effect, optionally in association with a pharmaceutically acceptable excipient, diluent, carrier or vehicle. The specifications for the novel unit dosage forms of the present invention depend on the particular compound employed and the effect to be achieved, and the pharmacodynamics associated with each compound in the host.

"Physiological conditions" refer to conditions in the body of an animal (e.g., a human). Physiological conditions include, but are not limited to, body temperature and an aqueous environment of physiologic ionic strength, pH and enzymes. Physiological conditions also encompass conditions in the body of a particular subject which differ from the "normal" conditions present in the majority of subjects, e.g., which differ from the normal human body temperature of approximately 37° C. or differ from the normal human blood pH of approximately 7.4.

By "physiological pH" or a "pH in a physiological range" is meant a pH in the range of approximately 7.0 to 8.0 inclusive, more typically in the range of approximately 7.2 to 7.6 inclusive.

As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, and the like. The term does not denote a particular age or gender.

The terms "polyethylene glycol", "PEG", "polyethylene oxide" and "PEO" are used interchangeably herein unless indicated otherwise. A CNP peptide (CNP22 or a variant thereof) conjugated via an amino group to a "PEOn" polymer associated with the number n, in general has the formula: $CH_3—[—O—CH_2CH_2—]_n—C(=O)—NHR$, where n is the number of ethylene oxide units and R denotes the rest of the peptide. The "PEOn" polymer can optionally have an alkylene group, $(CH_2)_n$, where n is an integer from 1 to 5, between the carbonyl carbon and the repeating ethylene oxide units. Such a "PEOn" (e.g., PEO12 or PEO24) polymer is monodispersed, i.e., is a single discrete polymer of a particular molecular weight. Similarly, a CNP peptide conjugated via an amino group to a "PEGnK" polymer associated with the number nK, in general has the formula: $CH_3—[—O—CH_2CH_2—]_p—C(=O)—NHR$, where p is an integer greater than 1. The "PEGnK" polymer also can optionally have an alkylene group, $(CH_2)_n$, where n is an integer from 1 to 5, between the carbonyl carbon and the repeating ethylene oxide units. However, such a "PEGnK" (e.g., PEG1K, PEG2K, PEG5K or PEG20K) polymer is polydispersed, i.e., contains a mixture of polymers having a distribution of molecular weights, where the number nK denotes the polymer number-average molecular weight ($M_n$) in kilo Daltons. For example, "PEG2K" conjugated to a CNP peptide denotes a polydispersed PEG polymer having a polymer number-average molecular weight of around 2 kDa.

When a range of the mass of a polymer (e.g., PEG) is given (e.g., in units of kDa), the range refers to a range of polymer number-average molecular weights, not to a range of molecular weights of multiple polymers in a polydispersed mixture, unless expressly indicated otherwise.

The term "halogen", "halide" or "halo" refers to fluorine, chlorine, bromine, and/or iodine.

The term "alkyl" refers to a linear or branched saturated monovalent hydrocarbon radical, wherein the alkyl may optionally be substituted with one or more substituents Q as described herein. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or a branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, including n-propyl and isopropyl), butyl (including all isomeric forms, including n-butyl, isobutyl, sec-butyl and tert-butyl), pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkoxy" refers to an —O-alkyl group. In certain embodiments, an alkoxy group may optionally be substituted with one or more substituents Q as described herein.

The term "haloalkyl" refers to an alkyl group that is substituted with one or more halide atoms. In certain embodiments, a haloalkyl group is substituted with one, two, three, four, five or six halide atoms. In certain embodiments, a haloalkyl group may optionally be substituted with one or more additional substituents Q as described herein.

The term "cycloalkyl" refers to a cyclic saturated bridged and/or non-bridged monovalent hydrocarbon radical, which may be optionally substituted with one or more substituents Q as described herein. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl.

The term "heterocyclyl" or "heterocyclic" refers to a monocyclic non-aromatic ring system or a multicyclic ring system that contains at least one non-aromatic ring, wherein one or more of the non-aromatic ring atoms are heteroatoms independently selected from O, S, or N, and the remaining non-aromatic ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of heterocyclic groups include, but are not limited to, acridinyl, azepinyl, benzimidazolyl, benzindolyl, benzoisoxazolyl, benzisoxazinyl, benzodioxanyl, benzodioxolyl, benzofuranonyl, benzofuranyl, benzonaphthofuranyl, benzopyranonyl, benzopyranyl, benzotetrahydrofuranyl, benzotetrahydrothienyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, chromanyl, chromonyl, cinnolinyl, coumarinyl, decahydroisoquinolinyl, dibenzofuranyl, dihydrobenzisothiazinyl, dihydrobenzisoxazinyl, dihydrofuryl, dihydropyranyl, dioxolanyl, dihydropyrazinyl, dihydropyridinyl, dihydropyrazolyl, dihydropyrimidinyl, dihydropyrrolyl, dioxolanyl, 1,4-dithianyl, furanonyl, furanyl, imidazolidinyl, imidazolinyl, imidazolyl, imidazopyridinyl, imidazothiazolyl, indazolyl, indolinyl, indolizinyl, indolyl, isobenzotetrahydrofuranyl, isobenzotetrahydrothienyl, isobenzothienyl, isochromanyl, isocoumarinyl, isoindolinyl, isoindolyl, isoquinolinyl, isothiazolidinyl, isothiazolyl, isoxazolidinyl, isoxazolyl, morpholinyl, naphthyridinyl, octahydroindolyl, octahydroisoindolyl, oxadiazolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, piperazinyl, piperidinyl, 4-piperidonyl, pteridinyl, purinyl, pyrazinyl, pyrazolidinyl, pyrazolyl, pyridazinyl, pyridinyl, pyridopyridinyl, pyrimidinyl, pyrrolidinyl, pyrrolinyl, pyrrolyl, quinazolinyl, quinolinyl, quinoxalinyl, quinuclidinyl, tetrahydrofuryl, tetrahydrofuranyl, tetrahydroisoquinolinyl, tetrahydropyranyl, tetrahydrothienyl, tetrazolyl, thiadiazolopyrimidinyl, thiadiazolyl, thiamorpholinyl, thiazolidinyl, thiazolyl, thienyl, triazinyl, triazolyl, and 1,3,5-trithianyl. In certain embodiments, a heterocyclic group may optionally be substituted with one or more substituents Q as described herein.

The term "aryl" refers to a monocyclic aromatic group or a multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where at least one of the rings is aromatic and the others may be saturated, partially unsaturated, or aromatic, for example, dihydronaphthyl, indenyl, indanyl, and tetrahydronaphthyl (tetralinyl). In certain embodiments, an aryl group may optionally be substituted with one or more substituents Q as described herein.

The term "heteroaryl" refers to a monocyclic aromatic group or a multicyclic aromatic group that contain at least one aromatic ring, wherein at least one aromatic ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. The heteroaryl may be attached to the main structure at any heteroatom or carbon atom which results in the creation of a stable compound. In certain embodiments, the heteroaryl has from 5 to 20, from 5 to 15, or from 5 to 10 ring atoms. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to, indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to, carbazolyl, benzindolyl, phenanthrollinyl, acridinyl, phenanthridinyl, and xanthenyl. In certain embodiments, a heteroaryl group may optionally be substituted with one or more substituents Q as described herein.

The term "optionally substituted" is intended to mean that a group, including alkyl, alkoxy, haloalkyl, cycloalkyl, heterocyclyl, aryl and heteroaryl, may be substituted with one or more substituents Q (in one embodiment, one, two, three or four substituents Q), where each Q is independently selected from the group consisting of cyano, halo, oxo, nitro, $C_{1-6}$ alkyl, $C_{1-6}$ alkoxy, halo-$C_{1-6}$ alkyl, $C_{3-7}$ cycloalkyl, heterocyclyl, $C_{6-14}$ aryl, heteroaryl, —C(O)$R^e$, —C(O)O$R^e$, —C(O)N$R^f R^g$, —C(N$R^e$)N$R^f R^g$, —O$R^e$, —OC(O)$R^e$, —OC(O)O$R^e$, —OC(O)N$R^f R^g$, —OC(=N$R^e$)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^f$, —N$R^e$C(O)O$R^f$, —N$R^e$C(O)N$R^f R^g$, —N$R^e$C(=NRh)N$R^f R^g$, —N$R^e$S(O)$R^f$, —N$R^e$S(O)$_2 R^f$, —N$R^e$S(O)N$R^f R^g$, —N$R^e$S(O)$_2$N$R^f R^g$, —S$R^e$, —S(O)$R^e$, —S(O)$_2 R^e$, and —S(O)$_2$N$R^f R^g$, wherein each $R^e$, $R^f$, $R^g$, and $R^h$ is independently hydrogen, $C_{1-6}$ alkyl, $C_{3-7}$ cycloalkyl, heterocyclyl, $C_{6-14}$ aryl, or heteroaryl; or $R^f$ and $R^g$, together with the N atom to which they are attached, form heterocyclyl.

B. CNP Variants

The use of CNP22 as a therapeutic is limited by its short half-life in plasma (J. Clin. Endocrinol. Metab., 78: 1428-35 (1994)). In human plasma, the concentration of CNP22 typically is less than five picomolar. CNP22 is degraded and cleared from circulation by NEP and NPR-C in humans (Growth Hormone & IGF Res., 16: S6-S14). In all human and animal studies using systemically administered CNP22, continuous infusion has been used to increase the CNP22 concentration in the subjects. A CNP peptide having a longer half-life and at least a similar level of functionality would be beneficial to a CNP-based therapeutic strategy.

The present invention provides CNP variants which have reduced affinity to NEP and/or NPR-C, and reduced susceptibility to cleavage by NEP and/or clearance by NPR-C, but which have substantially the same or better functionality than wild-type CNP22.

Natural substrates of NEP are small and natriuretic peptides (about 2.2 to about 3.2 kDa) are the largest of the natural substrates. According to X-ray crystallographic analyses, the NEP active-site is buried deep inside a central cavity, effectively restricting the size of substrate molecules to no more than about 3 kDa (Oefner et al., J. Mol. Biol., 296: 341-349 (2000)). Based on NPR-B signaling studies, variants of CNP-22, such as CNP-17 (retaining only the cyclic domain, Cys6-Cys22, of CNP22) and CNP-53 (CNP-22 with a 31-amino acid extension at the N-terminus), can still bind and activate NPR-B similarly to the 2.2 kDa wtCNP-22. Accordingly, the invention encompasses CNP variants conjugated to a natural (e.g., peptide) and/or synthetic (e.g., PEG) polymer at the N-terminus and/or C-terminus of CNP22 or variants thereof, which exhibit increased NEP resistance but retain the ability to bind and activate the NPR-B signaling receptor.

In one embodiment, the invention encompasses CNP variants represented by the general formula:

(SEQ ID NO: 139)
(x)-Cys$_6$-Phe$_7$-Gly$_8$-Leu$_9$-Lys$_{10}$-Leu$_{11}$-Asp$_{12}$-Arg$_{13}$-

Ile$_{14}$-Gly$_{15}$-Ser$_{16}$-Met$_{17}$-Ser$_{18}$-Gly$_{19}$-Leu$_{20}$-Gly$_{21}$-

Cys$_{22}$-(z),
or (SEQ ID NO: 140)
(x)-Gly$_1$-Leu$_2$-Ser$_3$-Lys$_4$-Gly$_5$-Cys$_6$-Phe$_7$-Gly$_8$-

Leu$_9$-Lys$_{10}$-Leu$_{11}$-Asp$_{12}$-Arg$_{13}$-Ile$_{14}$-Gly$_{15}$-Ser$_{16}$-

Met$_{17}$-Ser$_{18}$-Gly$_{19}$-Leu$_{20}$-Gly$_{21}$-Cys$_{22}$-(z), wherein:

(x) and (z) each independently are a natural polymer (e.g., a peptide sequence containing at least one amino acid) and/or a synthetic polymer (e.g., PEG) as described herein, such that the total mass of the CNP variant is characterized by the ranges described generally herein, e.g., in the range from about 2.6 kDa or 2.8 kDa to about 6 or 7 kDa. In one embodiment, the residues from Cys6 to Cys22 form a cyclic portion. In an embodiment, (x) and/or (z) comprise an amino acid extension derived from NPPC or a non-CNP polypeptide (e.g., ANP, BNP, IgG, etc.), wherein the extension contains 1 to 40, 1 to 35, 1 to 31, 5 to 35, 5 to 31 or 5 to 15 amino acids. In another embodiment, the CNP variants comprise one or more modifications and/or substitutions with another natural amino acid, an unnatural amino acid, a peptidomimetic and/or a peptide bond isostere at one or more of the following positions of CNP22: Gly1, Lys4, Gly5, Cys6, Phe7, Gly8, Leu9, Lys10, Leu11, Ile14, Gly15, Ser16, Met17, Gly19, Leu20 and Gly21.

In another embodiment, CNP variants having a total mass characterized by the ranges described generally herein, e.g., from about 2.6 kDa or 2.8 kDa to about 6 or 7 kDa, designed for increased resistance to NEP degradation, are represented by the general formula:

(SEQ ID NO: 141)
(x)-Cys$_6$-Phe$_7$-Gly$_8$-Leu$_9$-(h)$_{10}$-Leu$_{11}$-Asp$_{12}$-Arg$_{13}$-

Ile$_{14}$-Gly$_{15}$-Ser$_{16}$-Met$_{17}$-Ser$_{18}$-Gly$_{19}$-Leu$_{20}$-Gly$_{21}$-

Cys$_{22}$-(z),
or (SEQ ID NO: 6)
(x)-Gly$_1$-Leu$_2$-Ser$_3$-(b)$_4$-Gly$_5$-Cys$_6$-Phe$_7$-Gly$_8$-Leu$_9$-

(h)$_{10}$-Leu$_{11}$-Asp$_{12}$-Arg$_{13}$-Ile$_{14}$-Gly$_{15}$-Ser$_{16}$-Met$_{17}$-

Ser$_{18}$-Gly$_{19}$-Leu$_{20}$-Gly$_{21}$-Cys$_{22}$-(z), wherein:

(x) is a synthetic or natural polymeric group, or a combination thereof, wherein a non-limiting example of a synthetic polymeric group is PEG (or PEO), and a non-limiting example of a natural polymeric group is an amino acid sequence containing from 1 to 35 amino acids and derived from NPPC or variants thereof with substitutions and/or deletions, ANP, BNP, or other non-CNP (poly)peptides such as, e.g., serum albumin, IgG, histine-rich glycoproteins, fibronectin, fibrinogen, zinc finger-containing polypeptides, osteocrin or fibroblast growth factor 2 (FGF2);

(z) may be absent or may be a synthetic or natural polymeric group, or a combination thereof, wherein a non-limiting example of a synthetic polymeric group is PEG, and a non-limiting example of a natural polymeric group is an amino acid sequence derived from a natriuretic polypeptide (e.g., NPPC, CNP, ANP or BNP) or non-natriuretic polypeptide (e.g., serum albumin or IgG); and (b) and (h) independently may be the wild type Lys at that position or may be replaced with a conservative amino acid substitution or any natural or unnatural amino acid or peptidomimetic that does not have a reactive primary amine on a side chain, including but not limited to Arg, Gly, 6-hydroxynorleucine, citrulline (Cit), Gln, Glu or Ser. In one embodiment, (b) is Arg. In another embodiment, for improved NEP resistance, (b) is not Gly. In yet another embodiment, (h) is not Arg.

Non-limiting examples of amino acid sequences derived from NPPC or variants thereof include:

Arg,

Glu-Arg,

Gly-Ala-Asn-Lys-Lys, (SEQ ID NO: 7)

Gly-Ala-Asn-Arg-Arg, (SEQ ID NO: 8)

Gly-Ala-Asn-Pro-Arg, (SEQ ID NO: 9)

Gly-Ala-Asn-Gln-Gln, (SEQ ID NO: 10)

Gly-Ala-Asn-Ser-Ser, (SEQ ID NO: 11)

Gly-Ala-Asn-Arg-Gln, (SEQ ID NO: 12)

Gly-Ala-Asn-Arg-Met, (SEQ ID NO: 13)

Gly-Ala-Asn-Arg-Thr, (SEQ ID NO: 14)

Gly-Ala-Asn-Arg-Ser, (SEQ ID NO: 15)

Ala-Ala-Trp-Ala-Arg-Leu-Leu-Gln-Glu-His-Pro-Asn-Ala, (SEQ ID NO: 16)

Ala-Ala-Trp-Ala-Arg-Leu-Leu-Gln-Glu-His-Pro-Asn-Ala-Arg, (SEQ ID NO: 17)

Asp-Leu-Arg-Val-Asp-Thr-Lys-Ser-Arg-Ala-Ala-Trp-Ala-Arg, (SEQ ID NO: 18)

Gln-Glu-His-Pro-Asn-Ala-Arg-Lys-Tyr-Lys-Gly-Ala-Asn-Lys-Lys, (SEQ ID NO: 19)

Gln-Glu-His-Pro-Asn-Ala-Arg-Lys-Tyr-Lys-Gly-Ala-Asn-Arg-Arg, (SEQ ID NO: 20)

Asp-Leu-Arg-Val-Asp-Thr-Lys-Ser-Arg-Ala-Ala-Trp-Ala-Arg-Leu-Leu-Gln-Glu-His-Pro-Asn-Ala-Arg-Lys-Tyr-Lys-Gly-Ala-Asn-Lys-Lys, (SEQ ID NO: 21)
and Asp-Leu-Arg-Val-Asp-Thr-Lys-Ser-Arg-Ala-Ala-Trp-Ala-Arg-Leu-Leu-Gln-Glu-His-Pro-Asn-Ala-Arg-Lys-Tyr-Lys-Gly-Ala-Asn-Arg-Arg. (SEQ ID NO: 22)

Non-limiting examples of amino acid sequences derived from non-CNP polypeptides such as, e.g., ANP, BNP, serum albumin and IgG include:

Ser-Leu-Arg-Arg-Ser-Ser; (SEQ ID NO: 23)

Asn-Ser-Phe-Arg-Tyr; (SEQ ID NO: 24)

Ser-Pro-Lys-Met-Val-Gln-Gly-Ser-Gly; (SEQ ID NO: 25)

Met-Val-Gln-Gly-Ser-Gly; (SEQ ID NO: 26)

Lys-Val-Leu-Arg-Arg-Tyr; (SEQ ID NO: 27)

Lys-Val-Leu-Arg-Arg-His; (SEQ ID NO: 28)

Gly-Gln-His-Lys-Asp-Asp-Asn-Pro-Asn-Leu-Pro-Arg; (SEQ ID NO: 29)

Gly-Val-Pro-Gln-Val-Ser-Thr-Ser-Thr; (SEQ ID NO: 30)

Gly-Glu-Arg-Ala-Phe-Lys-Ala-Trp-Ala-Val-Ala-Arg-Leu-Ser-Gln; (SEQ ID NO: 31)
and Gly-Gln-Pro-Arg-Glu-Pro-Gln-Val-Tyr-Thr-Leu-Pro-Pro-Ser. (SEQ ID NO: 32)

In an embodiment, the N-terminal (x) group and/or the C-terminal (z) group of any of the CNP variants having an (x) and/or (z) group, as described herein, independently comprise an amino acid sequence that contains a small number of, if any, acidic natural or unnatural amino acids (e.g., Asp or Glu). In another embodiment, (x) and/or (z) are enriched in basic natural or unnatural amino acids (e.g., Lys, Arg or His) to maintain an alkaline pI similar to the pI of CNP22 (pI 8.9). In one embodiment, the pI of the CNP variants is in the range from about 8 to about 10.5, designed so that the CNP variants can diffuse more readily through the extracellular matrix surrounding chondrocytes of bone growth plates. In narrower embodiments, the pI of the CNP variants is from about 8.5 to about 10.5, or from about 8.5 to about 10, or from about 9 to about 10.

In yet another embodiment, (x) and/or (z) are enriched in polar natural or unnatural amino acids, designed for increased aqueous solubility. In still another embodiment, (x) and/or (z) contain a small number of, if any, hydrophobic natural or unnatural amino acids (e.g., Ala, Val, Leu, Ile or Met).

In a further embodiment, the N-terminus of the CNP variants terminates in at least one glycine residue, designed for increased serum half-life. In a related embodiment, to prevent pyroglutamate formation, the N-terminus of CNP variants terminates in a glycine residue if it would otherwise terminate in glutamine. In one embodiment, the (x) group contains an amino acid extension whose N-terminus terminates in at least one glycine residue. In another embodiment, (x) and/or (z) do not contain two adjacent basic natural or unnatural amino acids (e.g., Lys-Lys or Arg-Arg), designed to reduce susceptibility to cleavage by the protease furin. In an embodiment, (x) does not contain two adjacent basic amino acids immediately preceding the position corresponding to Gly1 of CNP22.

In still another embodiment, the (x) group and/or the (z) group of the CNP variants comprise an amino acid sequence derived from NPPC (e.g., derived from CNP53). In an embodiment, (x) comprises an amino acid sequence derived from the N-terminal tail of ANP or BNP. In another embodiment, (z) comprises an amino acid sequence derived from the C-terminal tail of ANP or BNP. In a further embodiment, (x) and/or (z) comprise an amino acid sequence derived from a non-natriuretic polypeptide such as, e.g., IgG, human serum albumin (HSA), histidine-rich glycoproteins, fibronectin, fibrinogen, zinc finger-containing polypeptides, FGF-2, and bone-targeting proteins (e.g., osteocrin, osteopontin, osteocalcin, and sialoprotein).

In any embodiment described herein in which CNP22 or a variant thereof can have an N-terminal (x) group and/or a C-terminal (z) group, (x) and/or (z) independently can contain an amino acid sequence derived from the functional domain of a bone morphogenetic protein (BMP). An N-terminal and/or C-terminal amino acid extension derived from the functional domain of a BMP can increase the NEP resistance, and hence the serum half-life of the CNP variant, by increasing the total mass of the CNP variant to characterized by the ranges described generally herein, e.g., a range from about 2.6 kDa or 2.8 kDa to about 6 or 7 kDa. In addition, since certain BMPs are growth factors and cytokines that induce the formation of bone and cartilage, a fragment derived from the functional domain of a BMP can promote chondrocyte, cartilage or bone growth by a mechanism distinct from activation of the guanylyl cyclase function of NPR-B by the cyclic domain of CNP22 or a variant thereof. Non-limiting examples of BMPs that promote bone formation and development, cartilage formation and development, and/or osteoblast differentiation include BMP1, BMP2, BMP3, BMP5, BMP7 and BMP8a. In an embodiment, the N-terminus and/or C-terminus of CNP22 or a variant thereof independently are conjugated to an amino acid sequence derived from the last 140 amino acids in the C-terminal portion of BMP1, BMP2, BMP3, BMP5, BMP7 or BMP8a.

In one embodiment, the CNP variants contain an amino acid extension at the N-terminus and/or C-terminus of CNP22 or CNP17, including but not limited to:

```
                                              (SEQ ID NO: 4)
DLRVDTKSRAAWARLLQEHPNARKYKGANKKGLSKGCFGL

KLDRIGSMSGLGC (CNP-53);

(SEQ ID NO: 60);
QEHPNARKYKGANKKGLSKGCFGLKLDRIGSMSGLGC (CNP-37,

Analog BL);

(SEQ ID NO: 61)
AAWARLLQEHPNAGLSKGCFGLKLDRIGSMSGLGC (Analog CA);

(SEQ ID NO: 62)
AAWARLLQEHPNARGLSKGCFGLKLDRIGSMSGLGC (Analog CB);

(SEQ ID NO: 63)
DLRVDTKSRAAWARGLSKGCFGLKLDRIGSMSGLGC (Analog CC);

(SEQ ID NO: 40)
RGLSKGCFGLKLDRIGSMSGLGC;

(SEQ ID NO: 38)
ERGLSKGCFGLKLDRIGSMSGLGC;

(SEQ ID NO: 64)
GANQQGLSKGCFGLKLDRIGSMSGLGC;

(SEQ ID NO: 65)
GANRRGLSKGCFGLKLDRIGSMSGLGC;

(SEQ ID NO: 66)
GANPRGLSKGCFGLKLDRIGSMSGLGC;

(SEQ ID NO: 67)
GANSSGLSKGCFGLKLDRIGSMSGLGC;

(SEQ ID NO: 144)
GHKSEVAHRFKGANKKGLSKGCFGLKLDRIGSMSGLGC;

and (SEQ ID NO: 68)
SPKMVQGSG-CNP17-KVLRRH (Analog CD) (CNP17 having

N-terminal and C-terminal tails derived from BNP).
```

In another embodiment, the CNP variants have a K4R substitution at position 4 of CNP22. Non-limiting examples of CNP(K4R) variants include:

```
                                              (SEQ ID NO: 36)
    GANRRGLSRGCFGLKLDRIGSMSGLGC (CNP27(Arg4))

(Analog AY);

(SEQ ID NO: 37)
    GANPRGLSRGCFGLKLDRIGSMSGLGC (CNP27(Pro4))

(Analog CI);

(SEQ ID NO: 41)
    RGLSRGCFGLKLDRIGSMSGLGC (Analog AZ);

(SEQ ID NO: 39)
    ERGLSRGCFGLKLDRIGSMSGLGC (Analog BA);

(SEQ ID NO: 69)
    GANQQGLSRGCFGLKLDRIGSMSGLGC (Analog CH);

and (SEQ ID NO: 70)
    GANSSGLSRGCFGLKLDRIGSMSGLGC (Analog CG).
```

In another embodiment, the CNP variants are chimera comprising CNP22 and an N-terminal peptide fragment, including but not limited to:

GHHSHEQHPHGANQQGLSKGCFGLKLDRIGSMSGLGC (Analog CQ) (histidine-rich glycoprotein (HRGP) fragment-CNP22 chimera); (SEQ ID NO: 76)

GAHHPHEHDTHGANQQGLSKGCFGLKLDRIGSMSGLGC (Analog CR) (HRGP fragment-CNP22 chimera); (SEQ ID NO: 77)

GHHSHEQHPHGANPRGLSKGCFGLKLDRIGSMSGLGC (Analog CX) (HRGP fragment-CNP22 chimera); (SEQ ID NO: 78)

GQPREPQVYTLPPSGLSKGCFGLKLDRIGSMSGLGC (Analog CF) (IgG$_1$(F$_c$) fragment-CNP22 chimera); (SEQ ID NO: 79)

GQHKDDNPNLPRGANPRGLSKGCFGLKLDRIGSMSGLGC (Analog CY) (human serum albumin (HSA) fragment-CNP22 chimera); (SEQ ID NO: 80)

GERAFKAWAVARLSQGLSKGCFGLKLDRIGSMSGLGC (Analog CE) (HSA fragment-CNP22 chimera); (SEQ ID NO: 81)

FGIPMDRIGRNPRGLSKGCFGLKLDRIGSMSGLGC (Analog CZ) (osteocrin "NPR C inhibitor" fragment-CNP22 chimera); and (SEQ ID NO: 82)

GKRTGQYKLGSKTGPGPKGLSKGCFGLKLDRIGSMSGLGC (Analog DA) (FGF2 "heparin-binding domain" fragment-CNP22 chimera). (SEQ ID NO: 83)

In yet another embodiment, the CNP variants are chimera comprising an N-terminal peptide fragment and CNP22 in which arginine is substituted for Lys4 of CNP22 ("CNP22 (K4R)"), including but not limited to:

GQPREPQVYTGANQQGLSRGCFGLKLDRIGSMSGLGC (Analog CK) (IgG$_1$(F$_c$) fragment-CNP22(K4R) chimera); (SEQ ID NO: 84)

GVPQVSTSTGANQQGLSRGCFGLKLDRIGSMSGLGC (Analog CL) (HSA fragment-CNP22(K4R) chimera); (SEQ ID NO: 85)

GQPSSSSQSTGANQQGLSRGCFGLKLDRIGSMSGLGC (Analog CM) (fibronectin fragment-CNP22(K4R) chimera); (SEQ ID NO: 86)

GQTHSSGTQSGANQQGLSRGCFGLKLDRIGSMSGLGC (Analog CN) (fibrinogen fragment-CNP22(K4R) chimera); (SEQ ID NO: 87)

GSTGQWHSESGANQQGLSRGCFGLKLDRIGSMSGLGC (Analog CO) (fibrinogen fragment-CNP22(K4R) chimera); and (SEQ ID NO: 88)

GSSSSSSSSSGANQQGLSRGCFGLKLDRIGSMSGLGC (Analog CP) (zinc finger fragment-CNP22(K4R) chimera). (SEQ ID NO: 89)

Chimera comprising IgG and CNP22 or a variant thereof are designed for, inter alia, increased resistance to NEP degradation and reduced binding to serum albumin. CNP chimera comprising a surface fragment of HSA are designed for, inter alia, reduced immunogenicity and reduced binding to serum albumin. HRGP-CNP22 and HRGP-CNP22(K4R) chimera containing a cationic, histidine-rich, non-lysine, non-arginine sequence at the N-terminus are designed for, inter alia, increased stability to proteases. Chimera containing an osteocrin fragment are designed to release, upon protease (e.g., furin) cleavage, the osteocrin fragment at bone growth plates, where the fragment would inhibit the clearance receptor NPR-C. With respect to chimera comprising an FGF2 heparin-binding fragment, heparin binding to the fragment is designed to protect the chimera from degradation, thereby providing a longer serum half-life. Chimera containing a fibronectin, fibrinogen, or zinc-finger fragment are designed for reduced binding to serum albumin, among other features.

Not intending to be bound by theory, a CNP variant of molecular weight from about 2.6 or 2.8 kDa to about 6 or 7 kDa which has increased resistance to NEP degradation and has similar or improved functionality (e.g., binding to NPR-B and stimulation of cGMP signaling) as compared to wtCNP22, may be more effective if it does not bind tightly to plasma proteins such as serum albumin. A CNP variant that does not bind tightly to plasma proteins (e.g., serum albumin) may be more effective in diffusing through cartilage, getting to chondrocytes of bone growth plates, and binding to and activating NPR-B for cGMP signaling. In one embodiment, CNP variants designed for reduced binding to plasma proteins (e.g., serum albumin) are chimeras comprising CNP22 or a variant thereof and a peptide fragment from IgG. In another embodiment, CNP variants designed for reduced binding to plasma proteins are chimeras comprising CNP22 or CNP22(K4R) and a fragment from a polypeptide (e.g., IgG, HSA, fibronectin, fibrinogen, a zinc finger-containing polypeptide, etc.). In yet another embodiment, CNP variants designed for reduced binding to plasma proteins comprise CNP22 or a variant thereof conjugated to a hydrophilic or water-soluble polymer. In one embodiment, the hydrophilic or water-soluble polymer is PEG (or PEO). In another embodiment, the hydrophilic or water-soluble polymer (e.g., PEG) is functionalized with one or more functional groups that impart a negative charge to the polymer under physiological conditions, such as, e.g, carboxyl, sulfate or phosphate groups, or a combination thereof.

In a further embodiment, the CNP variants are derivatives of CNP37, which is QEHPNARKYKGANKK-CNP22 (SEQ ID NO: 60). The CNP37 variants can contain amino acid addition(s), deletion(s), and/or substitution(s) with natural or unnatural amino acid(s) or peptidomimetic(s) (e.g., peptide bond isostere(s)) at any one or more of the 37 positions of CNP37. Non-limiting examples of substitutions that can be made in CNP37, based on the numbering of CNP22, include K4R, G5S, G5R, G8S, K10R, G15S, S16Q, M17N, G19R, and combinations thereof. In an embodiment, the CNP37 derivatives contain a substitution of Met17 to a natural (e.g., asparagine) or unnatural amino acid or peptidomimetic, designed in part to avoid oxidation of the sulfur atom of methionine. In another embodiment, the CNP37 variants contain substitution(s) of Lys8, Lys10, Lys14 and/or Lys15 (based on numbering from the N-terminus of CNP37) to non-basic natural or unnatural amino acid(s) or peptiomimetic(s), designed in part to reduce albumin binding.

In addition or alternatively to amino acid addition(s), deletion(s) and/or substitution(s), the CNP37 derivatives can be conjugated at the N-terminus, C-terminus, and/or an internal site to any of the moieties described herein, including but not limited to bone- or cartilage-targeting moieties (e.g., bone-targeting peptide domains), moieties that reduce renal clearance (e.g., negatively charged PEG moieties), hydrophilic polymers (e.g., PEG), amino acid sequences comprising one or more amino acids (e.g., osteocrin "NPR-C inhibitor" fragment), carbohydrates (e.g., carbohydrates recognized by receptors on the surface of cells at bone growth plates), hydrophobic acids (e.g., $C_5$-$C_{12}$ carboxylic acids and natural fatty acids), and combinations thereof.

In one embodiment, the CNP variants are modified CNP37 peptides having mutation(s)/substitution(s) at the furin cleavage site (underlined) to improve in vivo resistance to the furin protease, and/or containing glycine (underlined) at the N-terminus to improve plasma stability and prevent pyroglutamate formation. Such CNP37 variants include but are not limited to:

(SEQ ID NO: 71)
<u>G</u>QEHPNARKYKGAN<u>PK</u>GLSKGCFGLKLDRIGSMSGLGC (Analog CS);

(SEQ ID NO: 72)
<u>G</u>QEHPNARKYKGAN<u>QK</u>GLSKGCFGLKLDRIGSMSGLGC (Analog CT);

(SEQ ID NO: 73)
<u>G</u>QEHPNARKYKGAN<u>QQ</u>GLSKGCFGLKLDRIGSMSGLGC (Analog CU);

(SEQ ID NO: 74)
<u>G</u>QEHPNARKYKGAN<u>KP</u>GLSKGCFGLKLDRIGSMSGLGC (Analog CW);

and (SEQ ID NO: 75)
<u>G</u>QEHPNARKYKGAN<u>KK</u>GLSKGCFGLKLDRIGSMSGLGC (Analog DB).

In another embodiment, the CNP variants comprise CNP22 or variants thereof conjugated at the N-terminus and/or C-terminus to moiet(ies) that facilitate translocation of the variants across a cell membrane or cell barrier. In one embodiment, the CNP variants are conjugated at the N-terminus and/or C-terminus to peptide sequence(s) that facilitate transport of the variants across a cell membrane or cell barrier, including via active peptide transporters.

In a further embodiment, the N-terminus and/or C-terminus of CNP22 or a variant thereof are conjugated to chemical moieties such as, e.g., natural and/or synthetic polymers, to increase the total mass of the modified CNP peptide to characterized by the ranges described generally herein, e.g., a range from about 2.6 or 2.8 kDa to about 6 or 7 kDa. In one embodiment, the chemical moieties are biocompatible hydrophilic or water-soluble natural (e.g., peptides, carbohydrates) or synthetic (e.g., PEG (or PEO)) polymers.

In a particular embodiment, the N-terminus and/or C-terminus of CNP22 or a variant thereof are conjugated to PEG (or PEO) polymers to result in a total mass characterized by the ranges described generally herein, e.g., from about 2.6 or 2.8 kDa to about 6 or 7 kDa. Pegylation of CNP22 or a variant thereof is designed, inter alia, to reduce immunogenicity and improve half-life by reducing renal clearance and increasing protease resistance. A PEG moiety can be attached to the N- and/or C-terminus of CNP22 or any variant described herein, including but not limited to CNP-17 (the Cys6-Cys22 cyclized portion of CNP22), CNP37, and variants of CNP17, CNP22 or CNP37 having N- and/or C-terminal amino acid extension(s), amino acid substitution(s) and/or amino acid deletion(s). In an embodiment, the Lys4 and/or Lys10 residues of CNP17, CNP22 or CNP37, or variants thereof, are substituted with a natural or unnatural amino acid (e.g., Arg, Gly, Ser, Gln, Glu or Cit) or peptidomimetic that does not contain a reactive primary amine on a side chain, to preclude any potential PEGylation of these lysine residues. In one embodiment, the Lys4 and/or Lys10 residues of the CNP peptides are substituted with Arg. In another embodiment, the Lys10 residue is not substituted with Arg.

In a further embodiment, CNP variants (including CNP22 and variants thereof) having a PEG (or PEO) moiety and an amino acid extension at the N-terminus contain arginine at the position immediately preceding the position corresponding to Gly1 of CNP22. Such PEGylated CNP variants are designed for increased resistance to NEP degradation, reduced binding to serum albumin, and enhanced CNP functional activity (e.g., activation of cGMP signaling). Non-limiting examples of such PEGylated CNP variants include PEO24-CNP27(Arg4), PEO12-CNP27(Arg4), PEO24-GANRR-CNP22, PEO12-GANRR-CNP22, PEO24-CNP27(Pro4), PEO12-CNP27(Pro4), PEO24-GANPR-CNP22, PEO12-GANPR-CNP22, PEO24-GANQQ-CNP22, PEO12-GANQQ-CNP22, PEO24-ER-CNP22(K4R), PEO12-ER-CNP22(K4R), PEO24-ER-CNP22, PEO12-ER-CNP22, PEO24-R-CNP22(K4R), PEO12-R-CNP22(K4R), PEO24-R-CNP22, and PEO12-R-CNP22, wherein PEO24 is a monodispersed 1.2 kDa PEG polymer and PEO12 is a monodispersed 0.6 kDa PEG polymer. In one embodiment, the PEG (or PEO) polymer is conjugated to the N-terminus of the CNP variants.

The invention contemplates use of hydrophilic or water soluble polymers (e.g., PEG) that can vary in type (e.g., homopolymer or copolymer; random, alternating or block copolymer; linear or branched; monodispersed or polydispersed), linkage (e.g., hydrolysable or stable linkage such as, e.g., amide, imine, aminal, alkylene, or ester bond), conjugation site (e.g., at the N-terminus and/or C-terminus, preferably not at any of the residues in the cyclized region of CNP (corresponding to residues 6-22 of CNP22)), and length (e.g., from about 0.2, 0.4 or 0.6 kDa to about 2, 3, 4 or 5 kDa). The hydrophilic or water-soluble polymer can be conjugated to the CNP peptide by means of N-hydroxy succinimide (NHS)- or aldehyde-based chemistry or other chemistry, as is known in the art. Such CNP variants can be generated using, e.g., wtCNP22 (2.2 kDa), CNP17 retaining only the cyclized region (residues 6-22) of wtCNP22, CNP variants having an amino acid extension at the N-terminus and/or C-terminus of CNP22 or CNP17, or variants having amino acid substitutions, additions and/or deletions such as, e.g., CNP27(Arg4), CNP27(Pro4), R-CNP22, R-CNP22(K4R), ER-CNP22 and ER-CNP22(K4R). In an embodiment, the PEG-CNP variants having a total mass characterized by the ranges described generally herein, e.g., from about 2.6 or 2.8 kDa to about 6 or 7 kDa, contain a monodispersed, linear PEG (or PEO) moiety conjugated at the N-terminus and/or C-terminus via NHS- or aldehyde-based chemistry, or a two-arm or three-arm branched PEG moiety conjugated at the N-terminus and/or C-terminus via NHS-based chemistry. The invention also encompasses negatively charged PEG-CNP variants designed for reduced renal clearance, including but not limited to carboxylated, sulfated and phosphorylated compounds (Caliceti, Adv. Drug Deliv. Rev., 55: 1261-77 (2003); Perlman, J. Clin. Endo. Metab., 88: 3227-35 (2003); Pitkin, Antimicrob. Ag. Chemo., 29: 440-444 (1986); Vehaskari, Kidney Int'l, 22: 127-135 (1982)). In one embodiment, the PEG (or PEO) moiety contains carboxyl group(s), sulfate group(s), and/or phosphate group(s).

In an embodiment, the invention encompasses CNP22 or variants thereof conjugated via NHS- or aldehyde-based chemistry to PEG (or PEO) of the formula $(CH_2CH_2O)_n$, wherein n is an integer from about 6 to about 100, and the PEG polymer is from about 0.3 kDa to about 5 kDa. In another embodiment, n is an integer from about 12 to about 50, and the PEG polymer is from about 0.6 kDa to about 2.5 kDa. In yet another embodiment, n is an integer from about 12 to about 24, and the PEG polymer is from about 0.6 kDa to about 1.2 kDa. In still another embodiment, the terminal hydroxyl group of the PEG polymer is capped with a non-reactive group. In a particular embodiment, the end-capping group is an alkyl group, e.g., a lower alkyl group such as methyl.

In a further embodiment, the invention provides CNP variants having one or more peptide bonds or peptide bond isosteres that have reduced susceptibility to cleavage by peptidases including neutral endopeptidase (NEP). NEP is a membrane-bound zinc-dependent endopeptidase that cleaves a substrate peptide bond at the amino end of large hydrophobic residues. Thus, modification of a peptide bond at a cleavage site for NEP to an unnatural peptide or non-peptide bond may preclude or decrease the efficiency of NEP cleavage.

For ANP and CNP, NEP cleavage is reported to occur first at the Cys6-Phe7 bond within the cyclized region, then elsewhere throughout the remainder of the structures. For BNP, cleavage is reported to occur first at the peptide N-terminus, then within the cyclic structure. Although the primary NEP cleavage site on CNP is reported to be the Cys6-Phe7 bond, when wtCNP22 was exposed to NEP digestion for 2.5 minutes in vitro, all possible sites were unexpectedly hydrolyzed, with the Cys6-Phe7 and Gly8-Leu9 peptide bonds being slightly most labile, as described in Example 2.

Substrate specificity of NEP is primarily determined by two substrate-binding subsites, S1' and S2' (Oefner et al., J. Mol. Biol. 296:341-349 (2000)). The S1' site accepts a large hydrophobic P1' residue of which the N-terminal peptide bond is subjected to hydrolysis (e.g., Phe, Leu, Ile and Met). The S2' site generally prefers a smaller residue, termed P2' (e.g., Gly or Ser). In the case of CNP, Phe7 is reported to be the preferred P1' residue for the NEP S1' site, while Gly8 is the preferred P2' residue for the S2' site. Because these two subsites can together accommodate only a certain total side chain size, any increase in the total size of the P1'-P2' residues of CNP can potentially disrupt NEP binding. For example, addition of a chloride atom at the 3-position of the P1' Phe7 aromatic ring (i.e., 3-Cl-Phe7) can potentially modify (e.g., destabilize) interactions between CNP and the NEP cleavage sites, for example at the S1' subsite. Addition of a tertiary butyl group to the smaller P2' residue Gly8 (i.e., tBu-Gly8) can potentially disrupt the interaction between CNP and the S2' subsite.

Accordingly, in one embodiment, CNP variants of the invention include CNP having an increase in the size of the P1'-P2' residues, such as Phe7-Gly8, to interfere with substrate recognition at the active site, thereby reducing susceptibility to NEP cleavage. Natural amino acids, unnatural amino acids and/or peptidomimetic moieties are substituted for one or more large P1' hydrophobic residues, including but not limited to Phe7, Leu9, Leu11, Ile14, Met17 and Leu20, and/or for one or more smaller P2' residues, including but not limited to Cys6, Gly8, Gly15, Ser16 and Gly19.

The invention encompasses CNP variants comprising at least one modified amino acid and/or at least one modified peptide bond, at least one residue involved in substrate recognition and/or cleavage by NEP, wherein the modified amino acids and modified peptide bonds can be natural amino acids, unnatural amino acids, peptidomimetics and/or peptide bond isosteres. In one embodiment, the NEP cleavage site on CNP between Cys6 and Phe7 is modified. In a related embodiment, the peptide bond (—C(=O)—NH—) between Cys6 and Phe7 is replaced with one of the following peptide bond isosteres:

—$CH_2$—NH—, —C(=O)—N(R)—, where the amide group is alkylated with any of the following R groups: methyl, ethyl, n-propyl, isopropyl, cyclopropyl, n-butyl, isobutyl, sec-butyl or tert-butyl,
—C(=O)—NH—$CH_2$—,
—$CH_2$—S—,
—$CH_2$—S(O)$_n$—, where n is 1 or 2,
—$CH_2$—$CH_2$—,
—CH=CH—,
—C(=O)—$CH_2$—,
—CH(CN)—NH—,
—CH(OH)—$CH_2$—,
—O—C(=O)—NH—, or
—NHC(=O)NH—.

In another embodiment, the CNP variants are represented by the formula:

(SEQ ID NO: 90)
(x)-Gly$_1$-Leu$_2$-Ser$_3$-Lys$_4$-Gly$_5$-(b)$_6$-(c)$_7$-(d)$_8$-Leu$_9$-

Lys$_{10}$-Leu$_{11}$-Asp$_{12}$-Arg$_{13}$-Ile$_{14}$-Gly$_{15}$-Ser$_{16}$-Met$_{17}$-

Ser$_{18}$-Gly$_{19}$-Leu$_{20}$-Gly$_{21}$-Cys$_{22}$-(z), wherein:
(x) and (z) independently may be absent or may be selected from the group consisting of synthetic bone-targeting compounds such as, e.g., bisphosphonates; amino acid sequences useful in bone or cartilage targeting such as, e.g., polyAsp and polyGlu; amino acid sequences derived from bone-targeting domains of bone proteins such as, e.g., osteopontin, osteocalcin, and sialoprotein (Wang et al., Adv. Drug Delivery Rev., 57: 1049-76 (2005)); polymeric and non-polymeric molecules that reduce renal clearance such as, e.g., negatively charged PEGs; and natural polymers (e.g., those containing amino acids, fatty acids and/or carbohydrates) and synthetic polymers (e.g., PEGs) that increase resistance of the CNP variant to NEP degradation by increasing the total mass of the CNP variant to the ranges described generally herein, e.g., from about 2.6 or 2.8 kDa to about 6 or 7 kDa;

(b) and (c) may be the wild-type Cys6 and Phe7, another natural amino acid or an unnatural amino acid, or may contain a peptide bond isostere as described herein to increase resistance to NEP cleavage; and (d) may be the wild-type Gly8, or may be a larger natural or unnatural (e.g., t-Bu-Gly) amino acid or peptidomimetic to reduce binding to NEP.

In one embodiment, such CNP variants contain at least one modified amino acid at (b), (c) and/or (d).

Other peptide bonds within CNP may be cleaved even if CNP22 or a variant thereof has an NEP-resistant peptide bond or peptide bond isostere at Cys6-Phe7, including the Gly8-Leu9, Lys10-Leu11, Arg13-Ile14, Ser16-Met17, and Gly19-Leu20 bonds. Therefore, the invention encompasses CNP variants having peptide bond isostere(s) at one or more other NEP cleavages sites in addition to the Cys6-Phe7 bond, wherein the peptide bond isosteres include those described herein.

In another embodiment, the invention encompasses CNP variants having a cysteine analog at Cys6 and/or Cys22, including but not limited to homocysteine, penicillamine, 2-mercaptopropionic acid, and 3-mercaptopropionic acid. In an embodiment, such CNP variants have a cyclic domain formed by a disulfide bond between the wild-type Cys6 or analog and Cys22 or analog.

In yet another embodiment, one or more residues of CNP22 or a variant thereof, up to all the residues, are substituted with a D-amino acid. Substitution of an L-amino acid with a D-amino acid essentially moves the side chain about 120 degrees from its original position, thereby potentially disrupting the binding of the CNP peptide to NEP. In a specific embodiment, L-Phe at Phe7 is substituted with its D-enantiomer, D-Phe.

In still another embodiment, a beta amino acid such as, e.g., 3-amino-2-phenylpropionic acid (or 2-phenyl-beta-alanine), replaces the wild-type alpha-amino acid Phe7. Use of a beta-amino acid effectively increases the peptide backbone length by one methylene unit. Protease resistance can result from the change in substrate conformation or the increased distance between amino acid side chains.

Non-limiting examples of variants of CNP22 having an unnatural alpha-amino acid, a beta-amino acid or a peptide bond isostere include:

(SEQ ID NO: 56)
GLSKGC(CH$_2$NH)FGLKLDRIGSMSGLGC (Analog A), (SEQ ID NO: 57)
GLSKGC-(N-Me-Phe)-GLKLDRIGSMSGLGC (Analog B), (SEQ ID NO: 136)
GLSKGC-(D-Phe)-GLKLDRIGSMSGLGC (Analog E), (SEQ ID NO: 58)
GLSKGCF-(tBu-Gly)-LKLDRIGSMSGLGC (Analog F), (SEQ ID NO: 137)
GLSKGC-(3-Cl-Phe)-GLKLDRIGSMSGLGC (Analog G), and (SEQ ID NO: 59)
GLSKGC-[NHCH$_2$CH(Ph)CO]-GLKLDRIGSMSGLGC (Analog H, formed using 3-amino-2-phenylpropionic acid).

In a further embodiment, the CNP variants have a total mass characterized by the ranges described generally herein, e.g., from about 2.6 or 2.8 kDa to about 6 or 7 kDa, designed for increased resistance to NEP degradation, and are represented by the formula:

(SEQ ID NO: 46)
(x)-Gly$_1$-Leu$_2$-Ser$_3$-(a)$_4$-Gly$_5$-(b)$_6$-(c)$_7$-(d)$_8$-(e)$_9$-

(f)$_{10}$-(g)$_{11}$-Asp$_{12}$-Arg$_{13}$-(h)$_{14}$-Gly$_{15}$-Ser$_{16}$-(i)$_{17}$-

Ser$_{18}$-Gly$_{19}$-(j)$_{20}$-Gly$_{21}$-Cys$_{22}$-(z), wherein:

(x) and (z) independently may be absent or may be selected from the group consisting of synthetic bone-targeting compounds such as, e.g., bisphosphonates; amino acid sequences useful in bone or cartilage targeting such as, e.g., polyAsp and polyGlu; amino acid sequences derived from bone-targeting domains of bone proteins such as, e.g., osteopontin, osteocalcin, and sialoprotein; polymeric and non-polymeric moieties that reduce renal clearance such as, e.g., negatively charged PEGs; polymers containing, e.g., amino acids, hydrophobic acids, and/or carbohydrates; and synthetic hydrophilic polymers such as, e.g., PEGs;

(a) may be the wild-type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (a) is Arg;

(b) is selected from the group consisting of Cys and peptide-bond isosteres between Cys6 and Phe7 such as, e.g., Cys-CH$_2$—NH;

(c) is selected from the group consisting of L-Phe; D-Phe; 3-amino-2-phenylpropionic acid; N-alkylated derivatives of Phe, wherein the N-alkyl group is methyl, ethyl, n-propyl, isopropyl, cyclopropyl, n-butyl, isobutyl, sec-butyl or tert-butyl; and Phe analogs, wherein one or more ortho-, meta-, and/or para-positions of the benzene ring of the Phe analog are substituted with one or more substituents selected from the group consisting of halogen, hydroxyl, cyano, straight or branched C$_{1-6}$ alkyl, straight or branched C$_{1-6}$ alkoxy, straight or branched halo-C$_{1-6}$ alkyl, C$_{3-10}$ cycloalkyl, heterocyclyl, C$_{6-14}$ aryl and heteroaryl (examples include, but are not limited to, tyrosine, 3-chlorophenylalanine, 2,3-chloro-phenylalanine, 3-chloro-5-fluoro-phenylalanine, 2-chloro-6-fluoro-3-methyl-phenylalanine), or wherein the benzene ring of the Phe analog can be replaced with another aryl group (non-limiting examples include 1- and 2-naphthylalanine) or with a heteroaryl group (non-limiting examples include pyridylalanine, thienylalanine and furylalanine);

(d) is selected from the group consisting of Gly, tert-butyl-Gly (tBu-Gly), Thr, Ser, Val and Asn;

(e) is selected from the group consisting of Leu, Ser, Thr and peptide-bond isosteres such as, e.g., N-Me-Leu;

(f) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (f) is not Arg;

(g) is selected from the group consisting of Leu and peptide-bond isosteres such as, e.g., N-Me-Leu;

(h) is selected from the group consisting of Ile, tBu-Gly, and peptide-bond isosteres such as, e.g., N-Me-Ile;

(i) is selected from the group consisting of Met, Val, Asn, beta-Cl-Ala, 2-aminobutyric acid (Abu) and 2-amino-isobutyric acid (Aib); and (j) is selected from the group consisting of Leu, norleucine (Nle), homoleucine (Hleu), Val, tert-butyl-Ala (tBu-Ala), Ser, Thr, Arg, and peptide-bond isosteres such as, e.g., N-Me-Leu.

In another embodiment, the CNP variants have a total mass characterized by the ranges described generally herein, e.g., from about 2.6 or 2.8 kDa to about 6 or 7 kDa, designed for increased resistance to NEP cleavage, and are represented by the formula:

(SEQ ID NO: 143)
(x)-Gly$_1$-Leu$_2$-Ser$_3$-(a)$_4$-Gly$_5$-(b)$_6$-(c)$_7$-(d)$_8$-(e)$_9$-

(f)$_{10}$-(g)$_{11}$-Asp$_{12}$-Arg$_{13}$-(h)$_{14}$-(i)$_{15}$-Ser$_{16}$-(j)$_{17}$-

Ser$_{18}$-Gly$_{19}$-(k)$_{20}$-Gly$_{21}$-Cys$_{22}$-(z), wherein:

(x) and (z) independently may be absent or may be selected from the group consisting of synthetic bone-targeting compounds such as, e.g., bisphosphonates; amino acid sequences useful in bone or cartilage targeting such as, e.g., polyAsp and polyGlu; amino acid sequences derived from bone-targeting domains of bone proteins and derivatives thereof, such as, e.g., fusion proteins or peptide sequences of osteopontin, osteocalcin, sialoprotein, etc.; moieties that reduce renal clearance, including but not limited to hydrophilic or water-soluble polymers such as, e.g., charged PEG molecules; and moieties comprising, e.g., PEGs, amino acids, carbohydrates, and/or hydrophobic acids;

(a) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (a) is Arg;

(b) is selected from the group consisting of Cys and peptide bond isosteres between Cys6 and Phe7 such as, e.g., Cys-CH$_2$—NH;

(c) is selected from the group consisting of L-Phe; D-Phe; 3-amino-2-phenylpropionic acid; N-alkylated derivatives of Phe, wherein the N-alkyl group is methyl, ethyl, n-propyl, isopropyl, cyclopropyl, n-butyl, isobutyl, sec-butyl or tert-butyl; and Phe analogs, wherein one or more ortho-, meta-, and/or para-positions of the benzene ring of the Phe analog are substituted with one or more substituents selected from the group consisting of halogen, hydroxyl, cyano, straight or branched $C_{1-6}$ alkyl, straight or branched $C_{1-6}$ alkoxy, straight or branched halo-$C_{1-6}$ alkyl, $C_{3-10}$ cycloalkyl, $C_{6-14}$ aryl, heterocyclyl and heteroaryl (examples include, but are not limited to, tyrosine, 3-chlorophenylalanine, 2,3-chloro-phenylalanine, 3-chloro-5-fluoro-phenylalanine, 2-chloro-6-fluoro-3-methyl-phenylalanine), or wherein the benzene ring of the Phe analog can be replaced with another aryl group (non-limiting examples include 1- and 2-naphthylalanine) or with a heteroaryl group (non-limiting examples include pyridylalanine, thienylalanine and furylalanine);

(d) is selected from the group consisting of Gly, tert-butyl-Gly, Thr, Ser, Val and Asn;

(e) is selected from the group consisting of Leu, Ser, Thr, and peptide bond isosteres such as, e.g., N-Me-Leu;

(f) is selected from the group consisting of Lys, Arg, Gly, 6-hydroxy-norleucine, citrulline (Cit), Gln and Ser;

(g) is selected from the group consisting of Leu, Asn, and peptide bond isosteres such as, e.g., N-Me-Leu;

(h) is selected from the group consisting of Ile, tert-butyl-Gly (tBu-Gly), Asn, and peptide bond isosteres such as, e.g., N-Me-Ile;

(i) is selected from the group consisting of Gly, Arg, Ser and Asn;

(j) is selected from the group consisting of Met, Val, Asn, beta-Cl-Ala, 2-aminobutyric acid (Abu) and 2-amino-isobutyric acid (Aib); and (k) is selected from the group consisting of Leu, norleucine (Nle), homoleucine (Hleu), Val, tert-butyl-Ala (tBu-Ala), Arg, Thr, Ser, and peptide bond isosteres such as, e.g., N-Me-Leu.

To improve the delivery of the CNP variants to the target sites of bone-related disorders (e.g., skeletal dysplasias), the CNP variants can be attached (e.g., at the N-terminus and/or C-terminus) to bone- or cartilage-targeting moieties. Non-limiting examples of bone- or cartilage-targeting moieties include bisphosphonates; hydroxyapatite; glucosamine; collagen (e.g., collagen type X); polyAsp; polyGlu; and amino acid sequences derived from bone-targeting domains of bone proteins such as, e.g., osteocrin, osteopontin, osteocalcin, and sialoprotein.

In addition to being less susceptible to NEP cleavage, the CNP variants potentially have reduced affinity to the NPR-C clearance receptor, while retaining CNP functionality. Besides NEP-mediated degradation, the half-life of CNP22 is influenced by the clearance receptor, NPR-C, which shares 58% sequence homology with the extracellular peptide-binding domain of NPR-B. CNP22 binds tightly to not only NPR-B (7-30 pM affinity), but also NPR-C (11-140 pM) (Bennett, B. D. et al., J. Biol. Chem., 266: 23060-67 (1991); Koller K. J. & Goeddel, D. V., Circulation, 86: 1081-88 (1992); Suga, S. et al., Endocrinology, 130: 229-39 (1992)). Even though the NPR-B crystal structure has yet to be reported, sequence homology as well as similarities between the NPR-C and NPR-A crystal structures (He, X.-L. et al., Science, 293(5535): 1657-62 (2001); Ogawa, H. et al., J. Biol. Chem., 279(27): 28625-31 (2004); He, X.-L., J. Mol. Biol., 361(4): 698-714 (2006)) suggest that NPR-B likely assumes a similar overall structural fold.

Therefore, an NPR-B homology model was built based on structure-based sequence alignment and crystallographic structures of the following related systems: CNP bound to NPR-C, ANP bound to NPR-A, and ANP bound to NPR-C (He, X.-L. et al., Science, 293(5535): 1657-62 (2001); Ogawa, H. et al., J. Biol. Chem., 279(27): 28625-31 (2004); He, X.-L., J. Mol. Biol., 361(4): 698-714 (2006)). Based on observations that the receptor appears to determine the bound peptide conformation, and that NPR-B most closely resembles NPR-A with respect to primary structure and functional properties, the NPR-B/CNP homology model was built with the NPR-A/ANP crystal structure as a model. Published signaling data of CNP variants (U.S. Pat. No. 5,434,133 and US Patent Application Publication No. 2004/0138134 A1), and of functional ANP variants that no longer bind to NPR-C (Cunningham, EMBO 13(11) 2508-15, 1994) were used to refine and interpret the NPR-B/CNP model.

The present invention encompasses CNP variants designed for improved NPR-B selectivity based on a homology-based structural model of the NPR-B/CNP complex. Combining the experimental and computational structure data of natriuretic peptides bound to the various receptors with the published functional data, CNP variants were generated that continue to bind to NPR-B, but can potentially have reduced affinity to the NPR-C clearance receptor. For example, NPR-C has a unique insertion in a loop structure in the peptide-binding site, placing its loop residues closer to such peptide residues as CNP Gly8 (or ANP Gly9), compared to respective loop residues in NPR-A and NPR-B. Earlier studies indicated that the G9T mutation in ANP contributes to reduce affinity to NPR-C, thereby improving NPR-A selectivity (Cunningham, EMBO J., 13(11): 2508-15 (1994)). Accordingly, CNP variants were generated to replace the corresponding Gly8 residue with a larger residue (Ser, Val, Thr or Asn) to disrupt the CNP binding to NPR-C without affecting its binding to NPR-B. Further, one or more mutations were introduced at the C-terminal end of CNP, encompassing Gly15 to Gly21, which is predicted to interact with receptor-specific residues, based on the detailed structural analyses of the receptor/peptide complexes. For example, a G19R mutation in CNP22 does not result in a significant loss of NPR-B signaling activity. This mutation, however, cannot be modeled into the available crystal structure of NPR-C/CNP without altering the conformations of neighboring residues. These observations suggest that the G19R mutation may selectively disrupt the binding of CNP to a particular receptor, such as NPR-C.

In an embodiment, the CNP variants have substitution(s) at one or more Gly sites at positions 1, 5, 8, 15, 19 and 21, to reduce conformational flexibility and thereby increase receptor specificity. Comparative analyses of crystal structures of ANP bound to NPR-C and NPR-A (Ogawa, H. et al., J. Biol. Chem., 279: 28625-31 (2004); He, X.-L., J. Mol. Biol., 361: 698-714 (2006)) indicate that the conformational flexibility of ANP may play an important role in determining the receptor selectivity.

In one embodiment, functional CNP variants with potentially reduced affinity to NPR-C have one or more of the following amino acid substitutions: G1R, G1E, G5R, G5Q, G5S, F7Y, G8T, G8S, G8V, G8N, L9S, L9T, K10Cit, K10Q, K10S, I14N, G15R, G15S, G15N, G15Cit, S16Q, M17V, M17N, G19S, G19R, G19N, L20V, L20R, L20T, L20S, G21S, G21T and G21R. In an embodiment, the CNP variants have multipoint substitutions at positions 1, 5, 7, 8, 9, 10, 14, 15, 16, 17, 19, 20 and/or 21, and may optionally have modifications at any of the other positions in the peptide sequence of the variant.

In a further embodiment, the CNP variants described herein may be conjugated to moieties, up to a total mass characterized by the ranges described generally herein, e.g., from about 2.6 or 2.8 kDa to about 6 or 7 kDa, at the N-terminus, the C-terminus and/or an internal site, to facilitate bone/cartilage targeting, reduce NPR-C and renal clearance, increase resistance to NEP degradation, and/or improve CNP functionality. In one embodiment, the CNP variants are not conjugated to a polymeric moiety at a site within the cyclic region (corresponding to Cys6 to Cys22 of CNP22). Non-limiting examples of polymeric or non-polymeric moieties that can be conjugated to the CNP variants include synthetic bone-targeting compounds such as, e.g., bisphosphonates; bone/cartilage targeting peptide sequences such as, e.g., polyAsp and polyGlu; peptide sequences derived from bone-targeting domains of bone proteins such as, e.g., osteopontin, osteocalcin and sialoprotein; peptide sequences derived from the functional domains of bone morphogenic proteins such as, e.g., BMP2, BMP3, BMP5, BMP7 and BMP8a; peptide sequences derived from polypeptides of natriuretic origin such as, e.g., NPPC, ANP and BNP; other natural polymeric or non-polymeric moieties such as, e.g., carbohydrates, fatty acids and phospholipids; biocompatible synthetic hydrophilic polymers such as, e.g., PEG (or PEO); hydrophobic polymeric or non-polymeric moieties such as, e.g., heptanoic acid and pentanoic acid; and combinations thereof.

The CNP variants described herein can have substantially similar or better functional activity than CNP22, e.g, with respect to stimulation of cGMP production and signaling. In one embodiment, the CNP variants in vitro stimulate the production of at least about 50% of the cGMP level produced under the same concentration of wtCNP22 (e.g., 1 uM). In certain embodiments, the variants retain at least about 50%, 60%, 70%, 80%, 90%, 95% or 100% of the cGMP-stimulation activity of wild-type CNP22. In another embodiment, the CNP variants have improved cGMP-stimulation activity compared to CNP22.

Optionally excluded from the present invention are any of the natriuretic (e.g., CNP) peptides, fragments and variants specifically disclosed, and any of the natriuretic (e.g., CNP) peptides, fragments and variants actually produced, in any of the prior publications referenced herein, including but not limited to, U.S. Pat. Nos. 5,434,133, 6,034,231, 6,020,168, 6,743,425, 7,276,481, WO 94/20534, WO 02/047871, WO 2005/098490, WO 2004/047871, EP 0497368, EP 0466174, and Furuya et al., Biochem. Biophys. Res. Comm. 183: 964-969 (1992)). All such documents are incorporated by reference herein in their entirety.

In one embodiment, the present invention optionally excludes wild-type CNP53, wild-type CNP22, wild-type CNP17, wild-type BNP, and wild-type ANP. In another embodiment, the invention optionally excludes fragments of NPPC or CNP53 which are produced by proteolytic cleavage in vivo. In yet another embodiment, optionally excluded from the invention are the following truncated fragments of wild-type CNP53: CNP50, CNP46, CNP44, CNP39, CNP29 and CNP27.

In an embodiment, the present invention optionally excludes the peptides of SEQ ID NOs 1-4 and 6-71 as specifically disclosed in U.S. Pat. No. 7,276,481. In another embodiment, the invention optionally excludes peptides of SEQ ID NO 5, disclosed generically in U.S. Pat. No. 7,276,481, wherein such peptides are variants of CNP17 having at least one natural amino acid substitution at Leu9, Lys10, Leu11, Ser16, Met17, Gly19, and/or Leu20. In still another embodiment, optionally excluded are CNP17 variants in which CNP17 or variants thereof contain N-Me-Phe7, or N-Me-Phe7 and N-Me-Leu11. In a further embodiment, the invention optionally excludes CNP17 variants of SEQ ID NO 5, as disclosed in U.S. Pat. No. 7,276,481, which are fused or conjugated to growth hormone (GH), insulin-like growth factor 1 (IGF-1), or thyroid hormone (TH). In yet another embodiment, optionally excluded are CNP22 variants in which CNP22 is fused to GH, IGF-1 or TH, or attached to GH, IGF-1 or TH via a linker (e.g., a peptide linker). In still another embodiment, optionally excluded are CNP17 variants in which CNP17 or variants thereof are conjugated to biotin or fluorescein at the N-terminus or the C-terminus.

In a further embodiment, the present invention optionally excludes the peptides of Compound Nos. 1-27, and SEQ ID NOs 1-17, 22-24, 30, 31 and 40-42 as specifically disclosed in U.S. Pat. No. 5,434,133. In another embodiment, the invention optionally excludes peptides of SEQ ID NOs 18-21 and 25-29, disclosed generically in U.S. Pat. No. 5,434,133. In still another embodiment, the invention optionally excludes the peptides of SEQ ID NOs 1-4 and 9 as specifically disclosed in WO 94/20534.

In some embodiments, however, the invention still encompasses methods of use of the natriuretic (e.g., CNP) peptides, fragments and variants optionally excluded herein, as well as pharmaceutical compositions (including sterile pharmaceutical compositions) comprising such natriuretic (e.g., CNP) peptides, fragments and variants.

C. Synthesis and Purification of CNP Variants

In one embodiment, the CNP variants can be produced via recombinant expression using techniques commonly known in the art. See, e.g., Sambrook, Fritsch & Maniatis, Molecular Cloning: A Laboratory Manual, Second Edition. Cold Spring Harbor Laboratory Press (Cold Spring Harbor, N.Y. (1989)); DNA Cloning: A Practical Approach, Volumes I and II, D. N. Glover, Ed. (1985); and Current Protocols in Molecular Biology, John Wiley & Sons, Inc. (1994).

Recombinant CNP variant polynucleotides and polypeptides are expressed in an expression vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, including without limitation cosmids, plasmids (e.g., naked or contained in liposomes) and viruses that incorporate the recombinant polynucleotide. The expression vector is inserted into an appropriate host cell for expression of the polynucleotide and polypeptide via transformation or transfection using techniques known in the art. See, e.g., Sambrook, Fritsch & Maniatis, Molecular Cloning: A Laboratory Manual, Second Edition. Cold Spring Harbor, N.Y.: Cold Spring Harbor Laboratory Press, 1989.

Host cells used to produce CNP variants as described herein can be bacterial, yeast, insect, non-mammalian vertebrate, or mammalian cells. The mammalian cells include, but are not limited to, hamster, monkey, chimpanzee, dog, cat, bovine, porcine, mouse, rat, rabbit, sheep and human cells. The host cells can be immortalized cells (a cell line) or non-immortalized (primary or secondary) cells and can be any of a wide variety of cell types, such as, but not limited to, fibroblasts, keratinocytes, epithelial cells (e.g., mammary epithelial cells, intestinal epithelial cells), ovary cells (e.g., Chinese hamster ovary or CHO cells), endothelial cells, glial cells, neural cells, formed elements of the blood (e.g., lymphocytes, bone marrow cells), chondrocytes and other bone-derived cells, and precursors of these somatic cell types. Host cells containing the CNP variant DNA or RNA are cultured under conditions appropriate for growth of the cells, expression of the DNA or RNA and identification/selection of cells expressing the CNP variant.

In another embodiment, CNP variants are synthesized and purified according to the methods of Atherton and Sheppard, *Solid Phase Peptide Synthesis: a Practical Approach*, IRL Press (Oxford, England (1989)).

Peptides can be synthesized based on, e.g., the following peptide sequence of CNP: $G^1LS(K$ or $R)GC^6F^7G^8L(K$ or $R$ or $Nle$ or $6$-$OH$-$Nle)LDRIGSMSGLGC^{22}$.

Exemplary CNP variants include but are not limited to:

Analog A (GLSKGC(CH2NH)FGLKLDRIGSMSGLGC) (SEQ ID NO: 56) was made by converting the backbone "—C=O" group of $C^6$ to a "—CH$_2$" group;

Analog B (GLSKGC(N-Me-Phe)GLKLDRIGSMSGLGC) (SEQ ID NO: 57) was made by converting the backbone "—NH" group of $F^7$ to an "—N—CH$_3$" group;

Analog E (GLSKGC(D-Phe)GLKLDRIGSMSGLGC) (SEQ ID NO:136) was made using D-Phe at $F^7$;

Analog F (GLSKGCF(tBu-Gly)LKLDRIGSMSGLGC) (SEQ ID NO: 58) was made using a tertiary-butyl-Gly at $G^8$;

Analog G (GLSKGC(3-Cl-Phe)GLKLDRIGSMSGLGC) (SEQ ID NO:137) was made by adding a chloride atom to a meta position of the phenyl ring of $F^7$ (similar variants can be generated by making ortho, meta and/or para substitutions of the phenyl ring of Phe7 with Cl, F, Br, OH and/or CH$_3$); and Analog H (GLSKGC[NHCH$_2$CH(Ph)CO]GLKLD-RIGSMSGLGC) (SEQ ID NO: 59) was made using (±)-3-(amino)-2-phenylpropionic acid at $F^7$.

Examples of CNP variants having, e.g., amino acid extensions, substitutions with natural or unnatural amino acids or peptide bond isosteres, and/or conjugations to polymers or hydrophobic moieties, include without limitation:

```
Analog J   C6-CH2-NH, N-Me-L9, N-Me-L20           (SEQ ID NO: 91)

Analog K   N-Me-L9, N-Me-L20                      (SEQ ID NO: 92)

Analog L   N-Me-L9, N-Me-L11, N-Me-L20            (SEQ ID NO: 93)

Analog M   N-Me-L9, N-Me-L11                      (SEQ ID NO: 94)

Analog Z   K4R, F7Y                               (SEQ ID NO: 95)

Analog AA  K4R, G8V                               (SEQ ID NO: 96)

Analog AB  K4R, G8S                               (SEQ ID NO: 97)

Analog AC  K4R, G8T                               (SEQ ID NO: 98)

Analog AD  K4R, L9T                               (SEQ ID NO: 99)

Analog AE  K4R, G15R                              (SEQ ID NO: 100)

Analog AF  K4R, G15Cit                            (SEQ ID NO: 101)

Analog AG  K4R, M17V                              (SEQ ID NO: 102)

Analog AH  K4R                                    (SEQ ID NO: 35)
```

-continued

| | | |
|---|---|---|
| Analog AJ | K4R, L20V | (SEQ ID NO: 103) |
| Analog AK | K4R, L20t-Bu-Ala | (SEQ ID NO: 104) |
| Analog AT | G1E, K4E | (SEQ ID NO: 105) |
| Analog AV | G1E, K4E - pentanoic acid (attached at the N-terminus) | (SEQ ID NO: 106) |
| Analog AW | G1E, K4E - heptanoic acid (attached at the N-terminus) | (SEQ ID NO: 107) |
| Analog AX | CNP17 (delta N-term) | (SEQ ID NO: 2) |
| Analog AY | GANRR-CNP22(K4R) (CNP27(Arg4)) | (SEQ ID NO: 36) |
| Analog AZ | R-CNP22(K4R) | (SEQ ID NO: 41) |
| Analog BB | G1E - heptanoic acid (attached at the N-terminus) | (SEQ ID NO: 108) |
| Analog BC | G1E - pentanoic acid (attached at the N-terminus) | (SEQ ID NO: 109) |
| Analog BF | K4R, K10Cit | (SEQ ID NO: 110) |
| Analog BG | K4R, K10Q | (SEQ ID NO: 111) |
| Analog BH | K4R, K10R | (SEQ ID NO: 112) |
| Analog BJ | K4R, G15N | (SEQ ID NO: 113) |
| Analog BK | K4R, G15S | (SEQ ID NO: 114) |
| Analog BL | CNP-37<br>CNP-53 | (SEQ ID NO: 60) |
| Analog CA | AAWARLLQEHPNA-CNP22 | (SEQ ID NO: 61) |
| Analog CB | AAWARLLQEHPNAR-CNP22 | (SEQ ID NO: 62) |
| Analog CC | DLRVDTKSRAAWAR-CNP22 | (SEQ ID NO: 63) |
| Analog CD | SPKMVQGSG-CNP17-KVLRRH (N- and C-terminal BNP tails) | (SEQ ID NO: 68) |
| Analog CE | GERAFKAWAVARLSQ-CNP22 (HSA-CNP22) | (SEQ ID NO: 81) |
| Analog CF | GQPREPQVYTLPPS-CNP22<br>PEG(24K)-CNP22<br>PEG(20K)-CNP22<br>PEG(5K)-CNP22<br>PEG(2K)-CNP22<br>PEG(2K)-CNP17<br>PEG(1K)-CNP27(Arg4)<br>PEG(1K)-CNP22<br>PEO4-(PEO12)3(branched)-CNP22<br>PEO12-CNP22<br>PEO12-CNP27(Arg4)<br>PEO24-CNP27(Arg4);<br>and | (SEQ ID NO: 79) |

SEQ ID NOs: 1 to 6 and 34 to 144, and variants thereof that comprise up to 1, 2, 3, 4, or 5 further modifications.

In one embodiment, the CNP variants are cyclized via formation of a disulfide bond between $Cys^6$ and $Cys^{22}$. $Cys^6$ can be a cysteine analog such as, e.g., homocysteine or penicillamine. In a further embodiment, the CNP variants can be cyclized by a covalent bond formed head-to-tail, side chain-to-side chain, side chain-to-head, or side chain-to-tail. In an embodiment, the covalent bond is formed between an amino acid at or toward the N-terminus and an amino acid at or toward the C-terminus of the peptide (referred to as "terminal" amino acids in this context). In another embodiment, the covalent bond is formed between the side chains of the two terminal amino acids. In yet another embodiment, the covalent bond is formed between the side chain of one terminal amino acid and the terminal group of the other terminal amino acid, or between the terminal groups of the two terminal amino acids.

Head-to-tail cyclization of the terminal amine to the terminal carboxyl group can be carried out using a number of methods, e.g., using p-nitrophenyl ester, 2,4,5-trichlorophenyl ester, pentafluorophenyl ester, the azide method, the mixed anhydride method, HATU, a carbodiimide (e.g., DIC, EDC or DCC) with a catalyst such as HOBt, HONSu or HoAt, or on-resin cyclization.

In addition, the cyclic structure can be formed via a bridging group involving the side chains of amino acid residues of the CNP variant and/or the terminal amino acid residues. A bridging group is a chemical moiety that allows cyclization of two portions of the peptide. Non-limiting examples of bridging groups include amides, thioethers, thioesters, disulfides, ureas, carbamates, sulfonamides, and the like. A variety of methods are known in the art for incorporation of units having such bridging groups. For example, a lactam bridge (i.e., a cyclic amide) can be formed between the N-terminal amino group or an amino group on a side chain and the C-terminal carboxylic acid or a carboxyl group on a side chain, e.g., the side chain of lysine or ornithine and the side chain of glutamic acid or aspartic acid. A thioester can be formed between the C-terminal carboxyl group or a carboxyl group on a side chain and the thiol group on the side chain of cysteine or a cysteine analog.

Alternatively, a cross link can be formed by incorporating a lanthionine (thio-dialanine) residue to link alanine residues that are covalently bonded together by a thioether bond. In another method, a cross-linking agent, such as a dicarboxylic acid (e.g., suberic acid (octanedioic acid)), can link the functional groups of amino acid side chains, such as free amino, hydroxyl, and thiol groups.

Enzyme-catalyzed cyclization can also be used. For example, it has been reported that the thioesterase domain of tyrocidine synthetase can be used to cyclize a thioester precursor, a subtilisin mutant can be utilized to cyclize peptide glycolate phenylalanylamide esters, and the antibody ligase 16G3 can be employed to cyclize a p-nitrophenylester. For a review of peptide cyclization, see Davies, J. Peptide Sci., 9: 471-501 (2003), incorporated herein by reference in its entirety.

In certain embodiments, the final cyclized product has a purity of at least about 70%, 75%, 80%, 85%, 90%, 95%, 96%, 97%, 98%, or at least about 99%.

D. Chemically Modified CNP Variants

Chemical modification of CNP22 or variants thereof can potentially impart advantageous properties to the modified CNP peptides, such as increased stability and half-life and reduced immunogenicity (for a general discussion of chemical modification of therapeutic proteins, see Pharmazie, 57(1): 5-29 (2002)). For example, attaching natural or synthetic, polymeric or non-polymeric moieties (e.g., PEG) to CNP peptides, to increase the total mass of the CNP peptides to the ranges described generally herein, e.g., a range from about 2.6 or 2.8 kDa to about 6 or 7 kDa, can reduce the susceptibility of the modified peptides to in vivo cleavage by exopeptidases and/or endopeptidases (e.g., NEP). In addition to PEGylation, glycosylation and other chemical derivatization procedures, e.g., modification by phosphorylation, amidation, carboxylation, acetylation, methylation, and creation of acid-addition salts, amides, esters and N-acyl derivatives, may also mask potentially immunogenic regions and/or proteolytically sensitive regions (Science, 303: 480-482 (2004)).

Examples of chemical modifications include, without limitation, the polymer addition method of Bednarsaki and the cross-linking method of Altus Corporation for improving stability and protease resistance and reducing immunogenicity. Bednarsaki showed that polymer addition can improve protein temperature stability (J. Am. Chem. Soc., 114(1): 378-380 (1992)), and Altus Corporation found that glutaraldehyde cross-linking can improve enzyme stability.

Chemical modification of polypeptides can be performed in a non-specific fashion (leading to mixtures of derivatized species) or in a site-specific fashion (e.g., based on wild-type macromolecule reactivity-directed derivatization and/or site-selective modification using a combination of site-directed mutagenesis and chemical modification) or, alternatively, using expressed protein ligation methods (Curr. Opin. Biotechnol., 13(4): 297-303 (2002)).

Pegylated CNP Variants

In one embodiment, for increased stability (e.g., resistance to NEP degradation), CNP22 or variants thereof (including those having amino acid additions, substitutions and/or deletions) are conjugated to hydrophilic, natural or synthetic polymers, to increase the total mass of the modified CNP peptides to a range from about 2.6 kDa or 2.8 kDa to about 4, 5, 6, 7 or higher kDa. In certain embodiments, the added hydrophilic polymers have a total mass of about 0.6, 0.8, 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8, or about 5 kDa.

In an embodiment, the hydrophilic polymers are water-soluble so that the CNP peptides conjugated thereto do not precipitate out in an aqueous (e.g., physiological) environment. Further, the hydrophilic polymers are biocompatible, i.e., do not cause injury, toxicity or an immunological reaction in vivo.

The hydrophilic polymers can be branched or unbranched. In one embodiment, the hydrophilic polymers are not branched.

Various sites of conjugation of CNP22 or variants thereof to a hydrophilic polymer are possible, including but not limited to: (1) only at the N-terminus; (2) only at the C-terminus; (3) only at an internal site (e.g., Lys4); (4) at both the N-terminus and the C-terminus; (5) at the N-terminus and an internal site; and (6) at the C-terminus and an internal site. In one embodiment, CNP22 or variants thereof are conjugated to a hydrophilic polymer only at the N-terminus. In another embodiment, conjugation is only at an internal site (e.g., Lys4). In yet another embodiment, conjugation is at the N-terminus and an internal site (e.g., Lys4). In still another embodiment, for better functionality the CNP peptides are not conjugated to a hydrophilic polymer at a site (e.g., Lys10) within the cyclic domain (corresponding to Cys6 to Cys22 of CNP22). If conjugation to a hydrophilic polymer is based on bond formation with a reactive primary amino group on the CNP peptide, conjugation at an internal site (e.g., Lys4 and/or Lys10) can be prevented by substitution of Lys4 and/or Lys10 with a natural or unnatural amino acid or peptidomimetic that does not contain a reactive primary amino group on a side chain, such as, e.g., Gly, Ser, Arg, Asn, Gln, Asp, Glu or citrulline (Cit). In a particular embodiment, Lys4 and/or Lys10 are replaced with Arg. In another embodiment, Lys10 is not replaced with Arg.

Non-limiting examples of hydrophilic polymers include polymers formed from carboxylic acid-bearing monomers (e.g., methacrylic acid (MA) and acrylic acid (AA)), polyvinyl alcohols, polymers formed from hydroxyl-bearing monomers (e.g., hydroxyethyl methacrylate (HEMA), hydroxypropyl methacrylate (HPMA), hydroxypropyl methacrylamide, and 3-trimethylsilylpropyl methacrylate (TMSPMA)), polyalkylene oxides, polyoxyethylated polyols (e.g., glycerol), poly(ethylene glycol) (PEG), poly(propylene glycol), mono-$C_1$-$C_{10}$ alkoxy-PEGs (e.g., monomethoxy-PEG), tresyl monomethoxy-PEG, aryloxy-PEGs, PEG acrylate (PEGA), PEG methacrylate, PEG propionaldehyde, bis-succinimidyl carbonate PEG, copolymers of 2-methacryloyloxyethyl-phosphorylcholine (MPC) and N-vinyl pyrrolidone (VP), hydroxy functional poly(N-vinyl pyrrolidone) (PVP), SIS-PEG (SIS is polystyrene-polyisobutylene-polystyrene block copolymer), polystyrene-PEG, polyisobutylene-PEG, PCL-PEG (PCL is polycaprolactone), PLA-PEG (PLA is polylactic acid), PMMA-PEG (PMMA is poly(methyl methacrylate)), PDMS-PEG (PDMS is polydimethyloxanone), PVDF-PEG (PVDF is polyvinylidene fluoride), PLURONIC™ surfactants (polypropylene oxide-co-polyethylene glycol), poly(tetramethylene glycol), poly (L-lysine-g-ethylene glycol) (PLL-g-PEG), poly(L-lysine-g-hyaluronic acid) (PLL-g-HA), poly(L-lysine-g-phosphoryl choline) (PLL-g-PC), poly(L-lysine-g-vinyl pyrrolidone) (PLL-g-PVP), poly(ethylimine-g-ethylene glycol) (PEI-g-PEG), poly(ethylimine-g-hyaluronic acid) (PEI-g-HA), poly (ethylimine-g-phosphoryl choline) (PEI-g-PC), poly(ethylimine-g-vinyl pyrrolidone) (PEI-g-PVP), PLL-co-HA, PLL-co-PC, PLL-co-PVP, PEI-co-PEG, PEI-co-HA, PEI-co- PC, PEI-co-PVP, cellulose and derivatives thereof (e.g., hydroxyethyl cellulose), dextran, dextrins, hyaluronic acid and derivatives thereof (e.g., sodium hyaluronate), elastin, chitosan, acrylic sulfate, acrylic sulfonate, acrylic sulfamate, methacrylic sulfate, methacrylic sulfonate, methacrylic sulfamate, polymers and copolymers thereof, and polymers and copolymers of combinations thereof.

In a particular embodiment, the hydrophilic polymer is poly(ethylene glycol) (PEG), also called poly(ethylene oxide) (PEO). As used herein, the term "PEG" or "PEO" encompasses all the forms of PEG, branched and unbranched, which can be used to derivatize polypeptides, including without limitation mono-($C_1$-$C_{10}$) alkoxy-PEGs and aryloxy-PEGs.

In one embodiment, the PEG-CNP conjugates comprise a PEG (or PEO) polymer of the formula $(CH_2CH_2O)_n$, wherein n is an integer from about 6 to about 100, and the PEG polymer is from about 0.3 kDa to about 5 kDa. In another embodiment, n is an integer from about 12 to about 50, and the PEG polymer is from about 0.6 kDa to about 2.5 kDa. In yet another embodiment, n is from about 12 to about 24, and the PEG polymer is from about 0.6 kDa to about 1.2 kDa. In a further embodiment, the terminal hydroxyl group of the PEG polymer is capped with a non-reactive group. In a particular embodiment, the end-capping group is an alkyl group, e.g., a lower alkyl group such as methyl, so that the PEG polymer terminates in an alkoxy group. In an embodiment, the PEG polymer is not branched. In another embodiment, CNP22 or variants thereof are conjugated to a PEG polymer only at the N-terminus.

PEGs and PEOs potentially include molecules with a distribution of molecular weights, i.e., they are potentially polydispersed, depending on the manner in which they are prepared. The size/mass distribution of a polymeric preparation can be characterized statistically by its weight average molecular weight ($M_w$) and its number average molecular weight ($M_n$), the ratio of which is called the polydispersity index ($M_w/M_n$). $M_w$ and $M_n$ can be measured by mass spectroscopy. PEG-CNP variants conjugated to a PEG moiety larger than 1.5 kDa may exhibit a range of molecular weights due to the polydispersed nature of the parent PEG molecule. For example, in the case of mPEG2K (Sunbright ME-020HS, NOF Co.), the molecular masses of the PEG molecules are distributed over a range from about 1.5 kDa to about 3 kDa, with a polydispersity index of 1.036. By contrast, the PEGs conjugated to CNP22 or variants thereof using MS $(PEG)_n$ reagents (n=4, 8, 12 or 24, denoted as, e.g., "PEO12" or "PEO24") from Pierce Biotechnology (Rockford, Ill.) are monodispersed, having discrete chain length and defined molecular weight.

Methods for generating polypeptides comprising a PEG moiety are known in the art (see, e.g., U.S. Pat. No. 5,824,784). Methods for preparing PEGylated CNP peptides generally comprise the steps of (a) reacting CNP22 or a variant thereof with a PEGylation reagent under conditions suitable for attaching PEG to the CNP peptide (e.g., at the N-terminus), and (b) obtaining the reaction product(s). Because pegylating a CNP peptide might significantly alter its binding to NPR-B, depending on the size of the PEG moiety and the location of PEGylation, different kinds of PEG and PEGylation reaction conditions can be explored. The chemistry that can be used for PEGylation of a CNP peptide includes acylation of reactive primary amine(s) of the peptide using the NHS-ester of methoxy-PEG (O—[(N-Succinimidyloxycarbonyl)-methyl]-O'-methylpolyethylene glycol). Acylation with methoxy-PEG-NHS or methoxy-PEG-SPA results in an amide linkage that eliminates any charge of the original primary amine. PEG-CNP peptides designated with the symbol "PEO12" or "PEO24", as well as those designated with the symbol "PEG1K", "PEG2K", "PEG5K" or "PEG20K", are PEGylated via reaction of a primary amino group on the peptide with an NHS ester-activated, methoxy-end capped PEG reagent. PEG-CNP variants can also be prepared by other methods, e.g., via reductive amination involving a primary amino group on the peptide and a PEG aldehyde, such as, e.g., PEG-propionaldehyde, or mono-$C_1$-$C_{10}$ alkoxy or aryloxy derivatives thereof (see U.S. Pat. No. 5,252,714).

Unlike ribosome protein synthesis, synthetic peptide synthesis proceeds from the C-terminus to the N-terminus. Accordingly, Boc-PEG (containing tert-butyloxycarbonyl (Boc)) is one method to attach PEG to the C-terminus of a peptide (R. B. Merrifield, J. Am. Chem. Soc., 85(14): 2149-2154 (1963)). Alternatively, Fmoc (fluorenylmethoxycarbonyl) chemistry can be employed (E. Atherton and R. C. Sheppard, Solid Phase Peptide Synthesis: a Practical Approach, IRL Press (Oxford, England (1989)).

The present methods for preparing PEG-CNP variants provide a substantially homogenous mixture of polymer-protein conjugates. After purification, discrete PEG-CNP preparations are sufficiently pure for in vitro and in vivo testing of biological properties. As demonstrated herein, certain PEG-CNP variants exhibit reduced susceptibility to NEP cleavage and substantially similar or better functionality (e.g., stimulation of cGMP production).

As described herein, PEGylation reactions of CNP22 or variants thereof, using appropriate PEGylation reagent/CNP peptide ratios and reaction conditions, provide PEG-CNP derivatives. The nature and extent of PEGylation can be determined using, e.g., PAGE and HPLC analysis. In certain embodiments, at least about 50%, 60%, 70%, 80%, 90%, 95% or 99% of CNP22 or variants thereof are mono-PEGylated at the N-terminus. To optimize the beneficial effects of PEGylation on the biological properties of a CNP peptide, the polymer length, conformation (e.g., branched or linear), and/or functionalization (e.g., adding a negatively charged group) of a PEG moiety can be varied. PEGylated CNP variants are tested for NEP resistance, pharmacokinetics and bioactivity (e.g., the ability to bind to NPR-B and stimulate the generation of cGMP). PEGylated CNP variants that show improved NEP resistance and at least about 50% of the cGMP-stimulating activity of CNP22 can be further tested, e.g., in vitro in a rat chondrosarcoma cell-based achondroplasia model and in vivo in a murine achondroplasia animal model.

E. Methods of Using CNP Variants, Pharmaceutical Compositions of CNP Variants, and Routes of Administration
Methods of Using CNP Variants
Bone-Related Disorders Fibroblast growth factors (FGFs) play important roles in bone formation, and mutations in FGF receptor genes (FGFR 1, 2 and 3) give rise to a variety of inherited skeletal malformations (Curr. Biol., 5: 500-507 (1995)). In particular, activating mutations in FGFR-3 are responsible for disorders of the long bones, including achondroplasia, the most common form of human genetic dwarfism (Nature, 371: 252-254 (1994); Cell, 78: 335-342 (1994)), the milder disorder hypochondroplasia (Ann. N.Y. Acad. Sci., 785: 182-187 (1996)), and the more severe and neonatal lethal thanatophoric dysplasia (TD) types I and II (Hum. Mol. Genet., 5: 509-512 (1996); Nat. Genet., 9: 321-328 (1995)). Mouse models overexpressing FGF-2, and consequentially activating FGFR-3, show shortened long bones and macrocephaly (Mol. Biol. Cell, 6: 1861-73 (1995)). Consistent with this model, mice deficient in FGFR-3 show remarkable skeletal overgrowth with wider growth plates (Nature Genet., 12: 390-397 (1996)).

Complementary experiments with CNP, NPR-B and NPR-C suggest a link between the peptide ligand, the corresponding receptors, and bone growth. Activation of NPR-B by elevated plasma concentrations of CNP in transgenic mice causes skeletal overgrowth (Nat. Med., 10: 80-86 (2004)) histologically similar to that of the growth plate cartilage of FGFR-3 knockout mice (Nat. Genet., 4: 390-397 (1996)). In NPR-C knockout mice, NPR-C-mediated clearance of CNP should be eliminated; consistent with this prediction, the knockout animals show elongated long bones and elongated vertebrae with kyphosis (Proc. Natl. Acad. Sci. USA 96: 7403-08 (1999)). Conversely, CNP knockout mice are dwarfed with shorter long bones and vertebrae, a phenotype histologically similar to that of achondroplasia, and have increased mortality as a result of malocclusion and pulmonary restriction from the small rib cage (Proc. Natl. Acad. Sci. USA, 98: 4016-4021 (2001)). Consistent with the proposed role of CNP as an activator of NPR-B, the NPR-B knockout mouse has the same dwarfed skeletal phenotype and increased mortality as the CNP knockout mouse (Proc. Natl. Acad. Sci. USA, 101: 17300-05 (2004)). Furthermore, in a mouse model of achondroplasia with activated FGFR-3 in the cartilage, targeted overexpression of CNP in chondrocytes counteracts dwarfism (Yasoda et al., Nat. Med., 10: 80-86 (2004)). Additionally, CNP has been show to play a role in regulating endochondral bone growth and chondrocyte activity, including but not limited to chondrocyte proliferation and differentiation, inhibition of the mitogen activated protein (MAP) kinase/MEK (Raf-1) kinase signaling pathway, and promotion of endochondral ossification (Yasoda et al., Nat. Med., 10: 80-86 (2004)). These results suggest that activation of the CNP/NPR-B system is a potential therapeutic strategy for treatment of human achondroplasia.

By stimulating matrix production, proliferation and differentiation of chondrocytes and increasing long bone growth, the CNP variants of the invention are potentially useful for treating mammals, including humans, suffering from a bone-related disorder, such as a skeletal dysplasia. Non-limiting examples of CNP-responsive bone-related disorders include achondroplasia, hypochondroplasia, short stature, dwarfism, osteochondrodysplasias, thanatophoric dysplasia, osteogenesis imperfecta, achondrogenesis, chondrodysplasia punctata, homozygous achondroplasia, chondrodysplasia punctata, camptomelic dysplasia, congenital lethal hypophosphatasia, perinatal lethal type of osteogenesis imperfecta, short-rib polydactyly syndromes, hypochondroplasia, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, and spondyloepimetaphyseal dysplasia.

The CNP variants can also potentially be used to treat osteoarthritis. Osteoarthritis is a degenerative disease of the articular cartilage and occurs frequently in the elderly. Osteoarthritis involves destruction of the cartilage and proliferative change in the bone and cartilage resulting from degeneration of articular components, with the change resulting in a secondary arthritis (e.g., synovitis). The extracellular matrix proteins, which are the functional entity of the cartilage, are reduced, and the number of chondrocytes decreases in osteoarthritis (Arth. Rheum. 46(8): 1986-1996 (2002)). By promoting the matrix production, growth and differentiation of chondrocytes, the CNP variants can potentially be useful in treating osteoarthritis.

Vascular Smooth Muscle Disorders

CNP and other vasoactive peptides (including ANP, BNP and urodilatin) have vasodilator and diuretic properties and play an important role in cardiovascular homeostasis (J. Cardiovasc. Pharmacol., 117: 1600-06 (1998); Kidney Int., 49: 1732-37 (1996); Am. J. Physiol., 275: H1826-1833 (1998)). CNP is widely distributed in the cardiovascular system, especially in high concentration in vascular endothelial cells (J. Cardiovasc. Pharmacol., 117: 1600-06 (1998)). CNP is a potent relaxant of vascular smooth muscle, particularly in the coronary circulation (Biochem. Biophys. Res. Commun., 205: 765-771 (1994)), and is an inhibitor of smooth muscle cell proliferation (Biochem. Biophys. Res. Commun., 177: 927-931 (1991)). Although the vasodilator effect of CNP is less potent than that of ANP (about 1:100) (Hypertens. Res., 21: 7-13 (1998); Am. J. Physiol., 275: L645-L652 (1998)), CNP mRNA is increased in response to shear stress (FEBS Lett., 373: 108-110 (1995)) and plasma levels of CNP are elevated in inflammatory cardiovascular pathologies (Biochem. Biophys. Res. Commun., 198: 1177-1182 (1994)). CNP has been shown to suppress inflammation through inhibition of macrophage infiltration in injured carotid arteries of rabbits (Circ. Res., 91: 1063-1069 (2002)) and to directly inhibit cardiac fibroblast proliferation through an NPR-B/cGMP-dependent pathway (Endocrinology, 144: 2279-2284 (2003)).

The cardiovascular actions of CNP are mediated via activation of the NPR subtypes, NPR-B and NPR-C (Endocrinology, 130: 229-239 (1992)), the latter accounting for 95% of NPRs expressed in vivo (Science, 293: 1657-1662 (2001)). The CNP/NPR-B pathway leads to elevation of cGMP, a well-established secondary messenger in the cardiovascular system. NPR-C's 37-amino acid portion from the C-terminus has a consensus sequence that interacts with the heterotrimeric G protein $G_i$ (J. Biol. Chem., 274: 17587-17592 (1999)), which has been shown to regulate adenylate cyclase and phospholipase C activity (J. Biol. Chem., 276: 22064-70 (2001); Am. J. Physiol., 278: G974-980 (2000); J. Biol. Chem., 271: 19324-19329 (1996)). CNP mediates smooth muscle hyperpolarization and relaxation via activation of NPR-C and the opening of a G protein-regulated, inwardly rectifying $K^+$ channels (Proc. Natl. Acad. Sci. USA, 100: 1426-1431 (2003)). Likewise, CNP has important anti-proliferative effects in cardiac fibroblasts and, through interaction with NPR-C, regulates local blood flow and systemic blood pressure by hyperpolarizing smooth muscle cells (R. Rose and W. Giles, J. Physiol. 586: 353-366 (2008)).

By binding to NPR-B on vascular smooth muscle cells, CNP22 stimulates the production of cGMP, which acts as an intracellular secondary messenger to cause ultimately the relaxation of blood vessels. Based on the hypotensive actions of CNP, the CNP variants of the invention are potentially useful for treating hypertension, congestive heart failure, cardiac edema, nephredema, hepatic edema, acute and chronic renal insufficiency, and so on. In addition, activation of cGMP signaling suppresses the growth of vascular smooth muscle cells. Accordingly, the CNP variants of the invention can potentially be used to treat conditions or diseases caused by the abnormal growth of vascular smooth muscle cells, including but not limited to restenosis and arteriosclerosis.

The studies described above suggest that CNP may be a potential therapeutic candidate for vascular smooth muscle relaxation and remodeling. Pharmacological effects of CNP concerning certain disorders have been attributed, in part, to vasoprotective effects rather than to vasodilator activity (Am. J. Respir. Crit. Care Med., 170: 1204-1211 (2004)). Therefore, the CNP variants of the present invention can potentially be used to treat conditions, e.g., vascular smooth muscle disorders, in which CNP may have a vasoprotective effect, including without limitation inducing smooth muscle relaxation and inhibiting infiltration of macrophages into cardiac tissue. In one embodiment, the CNP variants are used to treat heart failure, including but not limited to acute decompensated heart failure and acute congestive heart failure.

Pharmaceutical Compositions of CNP Variants

A further embodiment of the present invention is directed to pharmaceutical compositions comprising an effective amount of a CNP variant, optionally another biologically active agent, and one or more pharmaceutically acceptable excipients, diluents, stabilizers, preservatives, solubilizers, emulsifiers, adjuvants and/or carriers. Such compositions can include diluents of various buffer content (e.g., Tris-HCl, phosphate), pH and ionic strength; additives such as detergents and solubilizing agents (e.g., Polysorbate 20, Polysorbate 80), anti-oxidants (e.g., ascorbic acid, sodium metabisulfite), preservatives (e.g., Thimerosol, benzyl alcohol) and bulking substances (e.g., lactose, mannitol). The use of excipients, diluents, carriers and so on in the formulation of pharmaceutical compositions is known in the art; see, e.g., Remington's Pharmaceutical Sciences, 18$^{th}$ Edition, pages 1435-1712, Mack Publishing Co. (Easton, Pa. (1990)), which is incorporated herein by reference in its entirety. An effective amount of an active ingredient is a therapeutically, prophylactically, or diagnostically effective amount, which can readily be determined by a person skilled in the art by taking into consideration such factors as body weight, age, and therapeutic goal.

The compositions comprising a CNP variant can also include a buffering agent to maintain the pH of a solution within a desired range. Exemplary agents include sodium acetate, sodium phosphate, and sodium citrate. Mixtures of these buffering agents can also be used. The amount of buffering agent useful in the composition depends largely on the particular buffer used and the desired pH of the solution. For example, acetate is a more efficient buffer at pH 5 than pH 6, so less acetate may be used in a solution at pH 5 than at pH 6. In one embodiment, the pH range for the compositions of the present invention is from about pH 3 to about pH 7.5.

The compositions of the present invention can further include an isotonicity-adjusting agent to render the solution isotonic and more compatible for injection. In an embodiment, the agent is sodium chloride within a concentration range of 0-150 mM.

The therapeutic methods described herein use pharmaceutical compositions comprising a CNP variant and one or more pharmaceutically acceptable excipients, diluents, carriers and/or vehicles, and optionally other therapeutic and/or prophylactic ingredients. Non-limiting examples of excipients include liquids such as water, saline, glycerol, polyethylene glycol, hyaluronic acid, ethanol, cyclodextrins, modified cyclodextrins (i.e., sufobutyl ether cyclodextrins), etc. Suitable excipients for non-liquid formulations are also known to those of skill in the art.

Pharmaceutically acceptable salts can be used in the compositions of the present invention and include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients and salts is available in Remington's Pharmaceutical Sciences, 18$^{th}$ Edition, Mack Publishing Company, (Easton, Pa. (1990)).

Auxiliary substances, such as wetting or emulsifying agents, biological buffering substances, surfactants, and the like, may also be present in vehicles. A biological buffer can be virtually any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

The pharmaceutical compositions can be tailored to the desired mode of administration of the compositions. For oral administration, the composition can take the form of, e.g., a tablet, capsule, or softgel capsule, or can be an aqueous or nonaqueous solution, suspension or syrup. Tablets and capsules for oral administration can include one or more commonly used carriers such as lactose and corn starch. Lubricating agents, such as magnesium stearate or sodium stearyl fumarate, can also be added. When liquid suspensions are used, the active agent can be mixed with emulsifying and suspending agents. If desired, flavoring, coloring and/or sweetening agents can also be added to solid and liquid formulations. Other optional components for incorporation into oral formulations include, but are not limited to, preservatives, suspending agents, thickening agents, and the like.

For solid compositions, conventional nontoxic solid carriers include, e.g., pharmaceutical grades of mannitol, lactose, starch, magnesium stearate, sodium saccharin, talc, cellulose, glucose, sucrose, magnesium carbonate, and the like. Liquid pharmaceutically administrable compositions can be prepared, e.g., by dissolving, dispersing, suspending, etc., an active agent and optional pharmaceutical adjuvants in an excipient, such as, e.g., water, saline, aqueous dextrose, glycerol, ethanol, and the like, to form a solution or suspension. If desired, the pharmaceutical compositions can also contain minor amounts of nontoxic auxiliary substances such as, e.g., wetting agents, emulsifying agents, pH buffering agents, tonicifying agents, and the like, e.g., sodium acetate, sorbitan monolaurate, triethanolamine sodium acetate, triethanolamine oleate, etc. Methods of preparing solid and liquid dosage forms are known, or will be apparent, to those skilled in this art (see, e.g., Remington's Pharmaceutical Sciences, referenced above).

Parenteral formulations can be prepared in conventional forms, e.g., as liquid solutions or suspensions, solid forms suitable for solubilization or suspension in liquid prior to injection, or as emulsions. For example, sterile injectable suspensions can be formulated according to techniques known in the art using suitable carriers, dispersing agents, wetting agents, suspending agents, and the like. The sterile injectable formulations can also be a sterile injectable solution or a suspension in a nontoxic, parenterally acceptable diluent or solvent. Among the acceptable vehicles and solvents that can be employed are water, Ringer's solution and isotonic sodium chloride solution. In addition, sterile fixed oils, fatty esters and/or polyols can be employed as solvents or suspending media.

The invention also provides containers, e.g., vials, tubes, bottles, and the like, comprising the sterile injectable compositions. Kits comprising such compositions may also include instructions for use, and optionally dispensing devices, such as aerosol dispensing device, syringe, and/or needle. In some embodiments, the composition is prepackaged within a syringe.

The pharmaceutical compositions can be formulated as a slow release, controlled release or sustained release system for maintaining a relatively constant level of dosage over a desired time period such as, e.g., 1 week, 2 weeks or 1 month. Slow release, controlled release and sustained release compositions can be prepared using, e.g., biodegradable polymeric systems, and can take the form of, e.g., microparticles, as is known in the art.

Dosages

As used herein, the term "therapeutically effective amount" of an active agent (e.g., a CNP variant) refers to an amount that provides therapeutic benefit to a patient. The amount may vary from one individual to another and may depend upon a number of factors, including the overall physical condition of the patient. A therapeutically effective amount of a CNP variant can be readily ascertained by one skilled in the art, using publicly available materials and procedures. For example, the amount of a CNP variant used for therapy should give an acceptable rate of growth based on growth charts for children ages 0-17 years with achondroplasia (214 females and 189 males), which list height for age, head circumference, and segmental growth (Horton W A et al., Standard growth curves for achondroplasia, J. Pediatr., 93: 435-8 (1978)). CDC charts can be used to assess weight for age and weight for height or BMI for age. Secondary outcomes with courses that are more chronic in nature can also be measured.

Having a longer serum half-life than wild-type CNP22, the CNP variants can potentially be administered less frequently than CNP22. The dosing frequency for a particular individual may vary depending upon various factors, including the disorder being treated and the condition and response of the individual to the therapy. In certain embodiments, a pharmaceutical composition containing a CNP variant is administered to a subject about one time per day, one time per two days, one time per three days, or one time per week. In one embodiment, for treatment of bone-related disorders (e.g., skeletal dysplasias, including achondroplasia), a daily or weekly dose of a CNP variant is administered to patients until and/or through adulthood.

The CNP variants described herein can be administered to patients at therapeutically effective doses to treat, ameliorate or prevent bone-related disorders (e.g., skeletal dysplasias, including achondroplasia) and conditions (e.g., vascular smooth muscle disorders) in which CNP can provide a vasoprotective effect. The safety and therapeutic efficacy of the CNP variants can be determined by standard pharmacological procedures in cell cultures or experimental animals, such as, for example, by determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Active agents exhibiting a large therapeutic index are normally preferred.

Data obtained from cell culture assays and animal studies can be used to formulate a range of dosage for use in humans. The dosage normally lies within a range of circulating concentrations that include the $ED_{50}$, with little or minimal toxicity. The dosage can vary within this range depending upon the dosage form employed and the route of administration utilized. The therapeutically effective dose can be determined from cell culture assays and animal studies.

Modes of Administration

The CNP variants, or pharmaceutical compositions comprising them, can be administered to subjects in various ways such as, e.g., by injection subcutaneously, intravenously, intra-arterially, intraperitoneally, intramuscularly, intradermally, or intrathecally. In an embodiment, the CNP variants are administered by a single subcutaneous, intravenous, intraarterial, intraperitoneal, intramuscular, intradermal or intrathecal injection once a day. The CNP variants can also be administered by direct injection at or near the site of disease. Further, the CNP variants can be administered by implantation of a depot at the target site of action (e.g., an abnormal or dysplasic bone). Alternatively, the CNP variants can be administered under the tongue (e.g., sublingual tablet) or by inhalation into the lungs (e.g., inhaler or aerosol spray), by delivery into the nasal cavity (e.g., intranasal spray), by delivery into the eye (e.g., eye drop), or by transdermal delivery (e.g., by means of a patch on the skin). The CNP variants may also be administered orally in the form of microspheres, microcapsules, liposomes (uncharged or charged (e.g., cationic)), polymeric microparticles (e.g., polyamides), microemulsions, and the like. It would be clear to one skilled in the art that the compositions can also be administered by other modes, and determination of the most effective mode of administration of the compositions is within the skill of the skilled artisan.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions include an effective amount of a CNP variant and one or more pharmaceutically acceptable excipients, carriers or diluents (e.g., buffers), and may optionally include other ingredients such as, e.g., adjuvants. In addition to a CNP variant, the composition also can optionally contain another active agent, which may enhance the effects of the CNP variant or may exert other pharmacological effects in addition to those of the CNP variant.

In general, the CNP variants can be administered as pharmaceutical formulations including those suitable for oral (including buccal and sub-lingual), rectal, nasal, topical, pulmonary, vaginal or parenteral (including intramuscular, intraarterial, intrathecal, subcutaneous and intravenous) administration, or in a form suitable for administration by inhalation or insufflation. One manner of administration is subcutaneous using a convenient daily or weekly dosage regimen, which can be adjusted according to the degree of affliction. A further method of administration is by osmotic pump or mini-pump, which allows for controlled, continuous delivery of the pharmaceutical composition over a pre-determined period.

A further method of administration is by osmotic pump (e.g., an Alzet pump) or mini-pump, which allows for controlled, continuous delivery of the pharmaceutical composition over a pre-determined period. The osmotic pump or mini-pump can be implanted subcutaneously, or near the target site (e.g., the long bones of limbs, the epiphyses, etc.).

As explained above, the CNP variants can potentially be used to treat conditions or diseases caused by the abnormal growth of vascular smooth muscle cells, including but not limited to restenosis and arteriosclerosis. For local delivery of a CNP variant to the diseased bodily vessel (e.g., blood vessel), the CNP variant can be delivered by means of a medical device (e.g., a stent) implanted at the diseased site. In one embodiment, the CNP variant is impregnated in a polymeric matrix or polymeric coating disposed over a stent. In another embodiment, the CNP variant is contained in reservoirs or channels formed in the body of a stent and covered by a porous polymeric membrane or layer through which the CNP variant can diffuse. The polymeric matrix, coating, membrane or layer can comprise at least one biodegradable (e.g., hydrophilic) polymer, as is known in the art. In a further embodiment, the CNP variant can be contained in micropores in the body of a stent. The CNP variant can be delivered from a stent by burst release, pulse release, controlled release or sustained release, or a combination thereof. For example, the stent can locally deliver the CNP variant to the diseased site in a burst release followed by a sustained release. Sustained release can be over a period up to about 2 weeks, 1 month, 2 months, 3 months, 6 months or 1 year.

Combination Therapy

In one embodiment, a CNP variant can be used in combination with one or more other active agents useful for treating, ameliorating or preventing CNP-responsive conditions or disorders such as, e.g., bone-related disorders (e.g., skeletal dysplasias) and vascular smooth muscle disorders. The other active agent(s) can enhance the effects of the CNP variant or exert other pharmacological effects in addition to those of the CNP variant. Non-limiting examples of active agents that can be used in combination with the CNP variants described herein are other natriuretic peptides (e.g., BNP) and inhibitors (e.g., antagonists) of peptidases (e.g., NEP and furin), NPR-C and tyrosine kinases (e.g., FGFR-3). By preventing NEP cleavage of the CNP variant, an NEP inhibitor can prolong the half-life of the variant. Examples of NEP inhibitors include, without limitation, thiorphan and candoxatril. Co-use of an NPR-C inhibitor can also prolong the half-life of the CNP variant via inhibition of the variant's clearance by NPR-C. A non-limiting example of an NPR-C inhibitor is the fragment FGIPMDRIGRNPR (SEQ ID NO: 82), which would be released at the target site (e.g., bone growth plate) upon proteolytic cleavage of the FGIPMDRIGRNPR-CNP22 chimera (Analog CZ) (SEQ ID NO: 82) or similar chimeras comprising variants of CNP22 (e.g., those containing amino acid substitution(s), addition(s), and/or deletion(s) relative to CNP22). Co-use of a tyrosine kinase inhibitor can accentuate the effects of a CNP therapy by inhibiting the tyrosine kinase receptor FGFR-3, a negative regulator of chondrocyte and bone growth. Non-limiting examples of tyrosine kinase inhibitors include those disclosed in U.S. Pat. Nos. 6,329,375 and 6,344,459.

To achieve the appropriate therapeutic outcome in the combination therapies, one would generally administer to the subject the CNP composition and other therapeutic(s) in a combined amount effective to produce the desired therapeutic outcome (e.g., restored bone growth). This process may involve administering the CNP composition and other therapeutic agent(s) at the same time. Simultaneous administration can be achieved by administering a single composition or pharmacological protein formulation that includes both the CNP variant and other therapeutic agent(s). Alternatively, the other therapeutic agent(s) can be taken separately at about the same time as a pharmacological formulation (e.g., tablet, injection or drink) of the CNP variant. The CNP variant can also be formulated into a foodstuff such as brownies, pancakes, or cake, suitable for ingestion.

In other alternatives, administration of the CNP variant can precede or follow administration of the other therapeutic agent(s) by intervals ranging from minutes to hours. In embodiments where the other therapeutic agent(s) and the CNP composition are administered separately, one would generally ensure that the CNP variant and the other therapeutic agent(s) are administered within an appropriate time of one another so that both the CNP variant and the other therapeutic agent(s) can exert, synergistically or additively, a beneficial effect on the patient. For example, one can administer the CNP composition within about 0.5-6 hours (before or after) of the other therapeutic agent(s). In one embodiment, the CNP composition is administered within about 1 hour (before or after) of the other therapeutic agent(s).

Identifying and Monitoring Patient Populations

Protocols can be established to identify subjects suitable for CNP therapy and to determine whether a given patient is responsive to CNP therapy. For example, for treatment of bone-related disorders, indicators of growth can be measured, such as long bone growth measurements in utero and neonatal and measurements of bone growth biomarkers such as CNP, cGMP, Collagen II, osteocalcin, and Proliferating Cell Nuclear Antigen (PCNA).

Additional aspects and details of the invention will be apparent from the following examples, which are intended to be illustrative rather than limiting.

F. EXAMPLES

Example 1

Synthesis of CNP Variants

CNP variants were prepared using the methods described herein. Substitutions with natural or unnatural amino acids or peptidomimetics were made, as indicated in Tables 1-3 (shown in Example 2), at the respective amino acid residues in the wild-type sequence of CNP22. In certain variants, additional amino acids were added to the N-terminal and/or C-terminal ends of the whole or a portion of the wild-type CNP22 sequence (see Table 3).

Also prepared were CNP variants in which a PEG (or PEO) moiety was conjugated to the N-terminus of CNP22 or variants thereof (see Table 4, shown in Example 2). PEGylation reagents can be obtained from the commercial sources shown in Table 5.

TABLE 5

| Vendor | Product Name | Name | MW (Da) | PEGylation Reagent |
|---|---|---|---|---|
| NOF | Sunbright ME-200CS | mPEG20K | 20,000 | $CH_3(CH_2CH_2O)450—(CH_2)5COO—NHS$ |
| NOF | Sunbright ME-050CS | mPEG5K | 5,000 | $CH_3(CH_2CH_2O)110—(CH_2)5COO—NHS$ |
| Pierce | (Methyl-PEG12)3-PEG4-NHSEster | (mPEG12)3-PEG4 | 2,400 | $[CH_3(CH_2CH_2O)12]3—(CH_2CH_2O)4—NHCO(CH_2)3—COO—NHS$ |
| NOF | Sunbright ME-020HS | mPEG2K | 2,000 | $CH_3(CH_2CH_2O)45—(CH_2)5COO—NHS$ |
| NOF | Sunbright ME-020CS | mPEG2K | 2,000 | $CH_3(CH_2CH_2O)45—(CH_2)5COO—NHS$ |
| NOF | Sunbright ME-010HS | mPEG1K | 1,000 | $CH_3(CH_2CH_2O)23—CO(CH_2)2COO—NHS$ |
| Pierce | Methyl PEG24-NHS Ester | MS(PEG)24 | 1,200 | $CH_3(CH_2CH_2O)24—(CH_2)2COO—NHS$ |
| Pierce | EZ-Link NHS-PEG12-Biotin | PEO12-Biotin | 940 | $Biotin-(CH_2CH_2O)12—(CH_2)2COO—NHS$ |
| Pierce | Methyl PEG12-NHS Ester | MS(PEG)12 | 690 | $CH_3(CH_2CH_2O)12—(CH_2)2COO—NHS$ |
| Pierce | EZ-Link NHS-PEG4-Biotin | PEO4-biotin | 590 | $Biotin-(CH_2CH_2O)4—(CH_2)2COO—NHS$ |

TABLE 5-continued

| Vendor | Product Name | Name | MW (Da) | PEGylation Reagent |
|---|---|---|---|---|
| Pierce | Mono(lactosylamido) mono(succinimidyl)suberate | LSS | 590 | |
| Pierce | EZ-link NHS-LC-LC-Biotin | LC-LC-Biotin | 570 | |
| Pierce | EZ-link NHS-LC-Biotin | LC-Biotin (LC = long chain) | 450 | |
| Pierce | EZ-link NHS-Biotin | Biotin | 340 | |

The PEG (also called PEO) polymers purchased from Pierce Biotechnology (Rockford, Ill.) are monodispersed—i.e., they contain a single discrete polymer of a particular molecular weight. By contrast, the PEG polymers purchased from NOF (Nippon Oil and Fat) are polydispersed—i.e., they contain a mixture of polymers having a distribution of molecular weights.

To PEGylate CNP22 or variants thereof, reaction and purification conditions are optimized for each PEG-CNP conjugate. According to a general PEGylation procedure, reaction mixtures contain about 1 mM CNP22 or a variant thereof, and about 1 to 5 mM NHS-activated PEG in potassium phosphate buffer, pH between about 5.0 and 6.5. To mono-PEGylate selectively at the peptide N-terminus and minimize PEGylation at an internal site (e.g., Lys4 of CNP22), the PEGylation reaction can be conducted under more acidic conditions (e.g., at a pH between about 5.5 and 6.5) to protonate selectively and hence deactivate the more basic primary amino group on the lysine side chain. After about 1 to 3 hours of incubation at room temperature, the PEGylation reaction is quenched by addition of aqueous glycine buffer. Reaction products are then separated by reverse-phase HPLC, optimized for each PEG-CNP conjugate. Fractionation samples are speedvacced to dryness, and reconstituted/formulated in 1 mM HCl. Identification and purity of each PEG-CNP product are determined by liquid chromatography-mass spectrometry (LC/MS).

Example 2

Cleavage of CNP Variants by Neutral Endopeptidase In Vitro

To determine the effects of amino acid substitutions, amino acid extensions, backbone modifications, side chain modifications and PEGylation on the susceptibility of CNP variants to neutral endopeptidase (NEP) cleavage, peptide cleavage assays were carried out using an in vitro assay that monitored disappearance of the non-cleaved CNP variant.

Recombinant human NEP (1 ug/mL final concentration) was added to 100 uM CNP variant diluted in 0.1 M Tris, pH 7. The reaction mixture was incubated at 37° C. for various periods of time, and the reaction was quenched with EDTA (10 mM final) followed by heat denaturation. The reaction mixture was reduced and then the reaction products were analyzed using HPLC and mass spectroscopy. The half-life of the CNP variant was calculated based on the disappearance of intact CNP variant over time. The results for digested CNP variants were compared to a parallel wtCNP22 digestion and normalized to the results for 100 uM CNP22 digested by 1 mg/mL NEP ($t_{1/2}$=80 min).

Table 1 lists the half-lives, based on the in vitro NEP cleavage assay, of various CNP variants having backbone or side chain modifications. Removal of three of the six NEP cleavage sites in Analog L nevertheless resulted in a significantly shorter half-life. The greatest resistance to NEP cleavage was exhibited by Analog N, which contains the D-enantiomer of all 22 amino acids of CNP22, and by Analog M, which has an N-methylated amide bond at both Leu9 and Leu11. However, both Analogs N and M failed to stimulate production of cGMP (see below).

Concerning Analogs A, B, E, F, G and H, half-lives were determined to be about 1.5- to about 2.5-fold longer for analog E and G. All of these six analogs showed resistance or improved resistance to cleavage at the Cys6-Phe7 bond relative to wtCNP22 (data not shown). The rank order of analog resistance to NEP at 1 ug/ml, based on half-life, is Analog G (3-Cl-Phe)≧Analog E (D-Phe)>Analog H ("beta-2 Phe"), Analog B (N-Me-Phe), and Analog F (t-Bu-Gly)= wtCNP22>Analog A (Cys-$CH_2$—NH). Analogs E and G have about 1.5 times longer half-life in comparison to wtCNP22. Besides resistance to cleavage of the Cys6-Phe7 bond, Analogs B, E, F, G and H also exhibited resistance to cleavage of the Gly8-Leu9 bond in the presence of 1 ug/mL NEP (data not shown). These results indicate that CNP variants having backbone or side chain modifications between Cys6 and Gly8 can be resistant to NEP cleavage of the Cys6-Phe7 bond and/or Gly8-Leu9 bond, but do not necessarily have improved overall resistance to NEP or a longer half-life than CNP22. The results seem to be contrary to reports in the literature that NEP first cleaves at the Cys6-Phe7 bond of CNP22 and then elsewhere.

TABLE 1

| | | | cGMP Response rel. to 1 uM CNP22[1] | | NEP Cleavage |
|---|---|---|---|---|---|
| Analog | Natriuretic Peptide | | 10 nM | 1 uM | ($t_{1/2}$, min) |
| | CNP22 (SEQ ID NO: 1) | | 46 ± 10 | 100 ± 13 | 80[2] |
| N | D-CNP22 (all D-amino acids) (SEQ ID NO: 115) | | 2 | 1 | >>160 |
| A | CNP22, C6—CH2—NH (reduced carbonyl) (SEQ ID NO: 56) | | 6 | 66 | 55 |
| B | CNP22, N-methyl-F7 (methylated amide) (SEQ ID NO: 57) | | 2 | 38 | 80 |

TABLE 1-continued

| Analog | Backbone and Side Chain Modifications Natriuretic Peptide | cGMP Response rel. to 1 uM CNP22[1] | | NEP Cleavage ($t_{1/2}$, min) |
|---|---|---|---|---|
| | | 10 nM | 1 uM | |
| BD | CNP22, N-methyl-L9 (SEQ ID NO: 116) | 2 | 8 | ND |
| BN | CNP22, N-methyl-L11 (SEQ ID NO: 117) | 10 | 51 | ND |
| BE | CNP22, N-methyl-L20 (SEQ ID NO: 118) | 2 | 5 | ND |
| M | CNP22, N-methyl-L9, N-methyl-L11 (SEQ ID NO: 94) | 1 | 11 | >>160 |
| K | CNP22, N-methyl-L9, N-methyl-L20 (SEQ ID NO: 92) | 1 | 1 | 80 |
| L | CNP22, N-methyl-L9, N-methyl-L11, N-methyl-L20 (SEQ ID NO: 93) | 18 | 10 | 30 |
| J | CNP22, C6—CH2—NH, N-methyl-L9, N-methyl-L20 (SEQ ID NO: 91) | ND | ND | 50 |
| E | CNP22, D-F7 (D-Phe) (SEQ ID NO: 136) | 2 | 6 | 130 |
| H | CNP22, Beta-2-F7 (3-amino-2-phenylpropionyl) (SEQ ID NO: 57) | 2 | 2 | 80 |
| G | CNP22, 3-chloro-F7 (SEQ ID NO: 137) | 17 | 93 | 135 |
| F | CNP22, t-butyl-G8 (SEQ ID NO: 58) | 2 | 18 | 80 |
| V | CNP22, K4G, 3,4-dichloro-F7 (SEQ ID NO: 119) | ND | ND | 68 |
| X | CNP22, K4G, 3-methyl-F7 (SEQ ID NO: 120) | ND | ND | 68 |
| | ANP | 10 | 23 | ND |

[1]Stimulation of cGMP production in NIH3T3 cells by natriuretic peptide relative to cGMP production in the presence of 1 uM CNP22
[2]CNP22 NEP resistance $t_{1/2}$ averaged 80 min. Due to variations in NEP catalytic activity between experiments, all CNP22 $t_{1/2}$ digestions were normalized to 80 min and the difference coefficient was used to calculate analog $t_{1/2}$ in each experiment to obtain an adjusted $t_{1/2}$.
ND = Not Determined Table 2 lists the half-lives, based on the in vitro NEP cleavage assay, of various CNP variants having substitutions with natural and/or unnatural amino acids. The greatest resistance to NEP cleavage was shown by Analog BK, which has K4R and G15S substitutions, and Analog BJ, which has K4R and G15N substitutions.

TABLE 2

| Analog | Specificity Mutations Natriuretic Peptide | cGMP Response relative to 1 uM CNP22[1] | | NEP Cleavage ($t_{1/2}$, min) |
|---|---|---|---|---|
| | | 10 nM | 1 uM | |
| | CNP22 (SEQ ID NO: 1) | 46 ± 10 | 100 ± 13 | 80 |
| AH | CNP22, K4R (SEQ ID NO: 35) | 59 | 121 | 80 |
| BP | CNP22, K4R, G5S (SEQ ID NO: 121) | 45 | ND | ND |
| BO | CNP22, K4R, G5R (SEQ ID NO: 122) | 18 | 80 | ND |
| P | CNP22, K4G (SEQ ID NO: 123) | ND | ND | 68 |
| Z | CNP22, K4R, F7Y (SEQ ID NO: 95) | 2 | 18 | ND |
| AB | CNP22, K4R, G8S (SEQ ID NO: 97) | 26 ± 26 | 86 ± 17 | ND |
| AA | CNP22, K4R, G8V (SEQ ID NO: 96) | 3 | 25 | ND |
| AC | CNP22, K4R, G8T (SEQ ID NO: 98) | 11 ± 2 | 66 ± 16 | 80 |
| AD | CNP22, K4R, L9T (SEQ ID NO: 99) | 4 | 68 | ND |
| BH | CNP22, K4R, K10R (SEQ ID NO: 112) | 12 | 80 | ND |
| BF | CNP22, K4R, K10Cit (SEQ ID NO: 110) | 6 | 33 | ND |
| BG | CNP22, K4R, K10Q (SEQ ID NO: 111) | 9 | 45 | ND |
| BY | CNP22, K4R, K10S (SEQ ID NO: 124) | 16 | 53 | ND |
| BK | CNP22, K4R, G15S (SEQ ID NO: 114) | 13 ± 1 | 71 ± 11 | ≧160 |
| BJ | CNP22, K4R, G15N (SEQ ID NO: 113) | 4 | 41 | 150 |
| AE | CNP22, K4R, G15R (SEQ ID NO: 100) | 0.3 | 0.3 | ND |
| AF | CNP22, K4R, G15Cit (SEQ ID NO: 101) | 1.4 | 2 | ND |
| BZ | CNP22, K4R, S16Q (SEQ ID NO: 125) | 42 | 116 | ND |
| BX | CNP22, K4R, M17N (SEQ ID NO: 126) | 40 ± 2 | 103 ± 17 | ND |
| AG | CNP22, K4R, M17V (SEQ ID NO: 102) | 10 | 65 | ND |
| BQ | CNP22, K4R, G19S (SEQ ID NO: 127) | 21 | 63 | ND |
| BR | CNP22, K4R, G19R (SEQ ID NO: 128) | 22 ± 6 | 84 ± 10 | ND |
| AJ | CNP22, K4R, L20V (SEQ ID NO: 103) | 0.2 | 8 | ND |
| AK | CNP22, K4R, L20t-butyl-Ala (SEQ ID NO: 104) | 1 | 21 | ND |
| AT | CNP22, G1E, K4E (SEQ ID NO: 105) | 11 | 54 | 60 |
| BS | CNP22, K4R, L20R (SEQ ID NO: 129) | 11 | 8 | ND |
| BT | CNP22, K4R, G21S (SEQ ID NO: 130) | 7 | 39 | ND |
| BU | CNP22, K4R, G21T (SEQ ID NO: 131) | 6 | 21 | ND |

TABLE 2-continued

| | Specificity Mutations | cGMP Response relative to 1 uM CNP22[1] | | NEP Cleavage |
|---|---|---|---|---|
| Analog | Natriuretic Peptide | 10 nM | 1 uM | ($t_{1/2}$, min) |
| BW | CNP22, K4R, G21R (SEQ ID NO: 132) | 20 | 21 | ND |
| | ANP | 10 | 23 | ND |

[1] Stimulation of cGMP production in NIH3T3 cells by natriuretic peptide relative to cGMP production in the presence of 1 uM CNP22

[2] CNP22 NEP resistance $t_{1/2}$ averaged 80 min. Due to variations in NEP catalytic activity between experiments, all CNP22 $t_{1/2}$ digestions were normalized to 80 min and the difference coefficient was used to calculate analog $t_{1/2}$ in each experiment to obtain an adjusted $t_{1/2}$.

ND = Not Determined

Table 3 lists the half-lives, based on the in vitro NEP cleavage assay, of CNP variants having N-terminal and/or C-terminal modifications, including amino acid extensions. Analogs AZ, CC, CF, BL, CS, CK and CL were most resistant to NEP degradation.

TABLE 3

| | N- and C-Terminal Modifications | cGMP Response rel. to 1 uM CNP22[1] | | NEP Cleavage |
|---|---|---|---|---|
| | Natriuretic Peptide | 10 nM | 1 uM | ($t_{1/2}$, min) |
| | CNP22 | 46 ± 10 | 100 ± 13 | 80 |
| BC | Pentanoic acid (N-term.)-CNP22, G1E (SEQ ID NO: 109) | ND | ND | ND |
| BB | Heptanoic acid (N-term.)-CNP22, G1E (SEQ ID NO: 108) | 32 ± 4 | 84 ± 19 | 45-65 |
| AV | Pentanoic acid (N-term.)-CNP22, G1E, K4E (SEQ ID NO: 106) | ND | ND | 120 |
| AW | Heptanoic acid (N-term.)-CNP22, G1E, K4E (SEQ ID NO: 107) | ND | ND | <20 |
| AX | CNP17 (delta N-term) (SEQ ID NO: 2) | 18 | 69 | ND |
| AZ | R-CNP22, K4R (SEQ ID NO: 41) | 54 ± 11 | 106 ± 15 | ≧160 |
| BA | ER-CNP22, K4R (SEQ ID NO: 39) | 38 ± 10 | 113 ± 10 | 90 |
| AY | GANRR-CNP22, K4R (CNP-27) (SEQ ID NO: 36) | 59 ± 9 | 105 ± 20 | 65 |
| CH | GANQQ-CNP22, K4R (SEQ ID NO: 69) | 44 ± 8 | 95 ± 11 | ND |
| CI | GANPR-CNP22, K4R (SEQ ID NO: 37) | 50 ± 1 | 105 ± 12 | ND |
| CG | GANSS-CNP22, K4R (SEQ ID NO: 70) | 27 ± 1 | 88 ± 1 | 95 |
| CA | AAWARLLQEHPNA-CNP22 (SEQ ID NO: 61) | 24 | 76 | ND |
| CB | AAWARLLQEHPNAR-CNP22 (SEQ ID NO: 62) | 36 | 84 | ND |
| CC | DLRVDTKSRAAWAR-CNP22 (SEQ ID NO: 63) | 34 | 101 | >160 |
| CF | GQPREPQVYTLPPS-CNP22 (IgG1(Fc) fragment) (SEQ ID NO: 79) | 23 ± 9 | 72 ± 19 | >160 |
| BL | QEHPNARKYKGANKK-CNP22 (CNP37) (SEQ ID NO: 60) | 43 ± 15 | 97 ± 27 | >>160 |
| CE | GERAFKAWAVARLSQ-CNP22 (HSA fragment) (SEQ ID NO: 81) | 15 | 87 | ND |
| CY | GQHKDDNPNLPRGANPR-CNP22 (HSA fragment) (SEQ ID NO: 80) | ND | ND | ND |
| CQ | GHHSHEQHPHGANQQ-CNP22 (HRGP fragment) (SEQ ID NO: 76) | 16 | 95 | ND |

TABLE 3-continued

| Natriuretic Peptide | N- and C-Terminal Modifications | cGMP Response rel. to 1 uM CNP22[1] 10 nM | 1 uM | NEP Cleavage ($t_{1/2}$, min) |
|---|---|---|---|---|
| CX | GHHSHEQHPHGANPR-CNP22 (HRGP fragment) (SEQ ID NO: 78) | ND | ND | ND |
| CS | GQEHPNARKYKGANPK-CNP22 (modified CNP37) (SEQ ID NO: 129) | 19 | 61 | >>160 |
| CT | GQEHPNARKYKGANQK-CNP22 (modified CNP37) (SEQ ID NO: 130) | 60 | 121 | ND |
| CU | GQEHPNARKYKGANQQ-CNP22 (modified CNP37) (SEQ ID NO: 131) | 9 | 57 | ND |
|  | GQEHPNARKYKGANKK-CNP22 (modified CNP37) (SEQ ID NO: 132) | ND | ND | ND |
| CW | GQEHPNARKYKGANKP-CNP22 (modified CNP37) (SEQ ID NO: 74) | ND | ND | ND |
| CR | GAHHPEHDTHGANQQ-CNP22 (HRGP fragment) (SEQ ID NO: 128) | 14 ± 5 | 77 ± 12 | ND |
| CZ | FGIPMDRIGRNPR-CNP22 (osteocrin "NPR-C inhibitor") (SEQ ID NO: 82) | ND | ND | ND |
| DA | GKRTGQYKLGSKTGPGPK-CNP22 (FGF2 "heparin-binding domain" fragment) (SEQ ID NO: 83) | ND | ND | ND |
| CK | GQPREPQVYTGANQQ-CNP22, K4R (IgG1 fragment) (SEQ ID NO: 84) | 2 | 32 | ≧160 |
| CL | GVPQVSTSTGANQQ-CNP22, K4R (HSA fragment) (SEQ ID NO: 85) | 3 | 35 | >160 |
| CN | GQTHSSGTQSGANQQ-CNP22, K4R (fibrinogen) (SEQ ID NO: 87) | 12 | 115 | ND |
| CM | GQPSSSQSTGANQQ-CNP22, K4R (fibronectin) (SEQ ID NO: 86) | ND | ND | ND |
| CO | GSTGQWHSESGANQQ-CNP22, K4R (fibrinogen) (SEQ ID NO: 88) | 2 | 33 | ND |
| CP | GSSSSSSSSSGANQQ-CNP22, K4R (zinc finger) (SEQ ID NO: 89) | ND | ND | ND |
| CD | SPKMVQGSG-CNP17-KVLRRH ("BNP tails") (SEQ ID NO: 109) | 25 | 102 | ND |
| CJ | RSSCFGGRIDRIGAC ("C-ANP4-23", ANP-derived) (SEQ ID NO: 133) | ND | ND | ND |
|  | CNP22, K4R, K10R, N.-term.--N.-term. dimer/disuccinimidyl glutarate (SEQ ID NO: 134) | 19 | 44 | ND |
|  | CNP22, K4R, K10R, N-term.--N.-term. dimer/Bis-PEO5 (SEQ ID NO: 135) | 19 | 41 | ND |
| BM | CNP53 (SEQ ID NO: 4) | 61 | 101 | >>160 |
|  | ANP | 10 | 23 | ND |

[1]Stimulation of cGMP production in NIH3T3 cells by natriuretic peptide relative to cGMP production in the presence of 1 uM CNP22
[2]CNP22 NEP resistance $t_{1/2}$ averaged 80 min. Due to variations in NEP catalytic activity between experiments, all CNP22 $t_{1/2}$ digestions were normalized to 80 min and the difference coefficient was used to calculate analog $t_{1/2}$ in each experiment to obtain an adjusted $t_{1/2}$.
ND = Not Determined Table 4 lists the half-lives, based on the in vitro NEP cleavage assay, of CNP variants conjugated to PEG (or PEO) polymers at the N-terminus. All the PEGylated CNP variants tested and shown in Table 4 displayed resistance or enhanced resistance to NEP cleavage except for PEO12-CNP27(Pro4) (i.e., PEO12-GANPR-CNP22(K4R)), which had the same half-life as wtCNP22. Interestingly, N-terminal PEGylation of CNP22 having a K4G substitution does not seem to confer significant improvement in NEP resistance. For example, PEG2K-CNP22(K4G) was only slightly more resistant to NEP cleavage than CNP22 (data not shown), whereas PEG2K-CNP22 had a much longer half-life in vitro than CNP22.

N-terminus. PEGylation of CNP27(Arg4) greatly improved the NEP resistance of this CNP variant, with PEO24-CNP27 (Arg4) being completely resistant to NEP cleavage over the assay period of 160 minutes. Increasing the mass of the PEO moiety from about 0.6 kDa (PEO12) to about 1.2 kDa (PEO24) improved the NEP resistance of PEGylated CNP27 (Arg4). PEGylation of CNP27(Arg4) to a monodispersed PEO24 moiety rather than a polydispersed PEG1K moiety also improved NEP resistance. Finally, although both PEO24-CNP27(Arg4) and PEG2K-CNP17 have a similar total mass (keeping in mind that PEG2K is polydispersed), the former displayed significantly better NEP resistance.

TABLE 4

| N-Terminal PEGylation | | cGMP Response rel. to 1 uM CNP22[1] | | NEP Cleavage |
| --- | --- | --- | --- | --- |
| Natriuretic Peptide | PEG | 10 nM | 1 uM | ($t_{1/2}$, min) |
| CNP22 | | 46 ± 10 | 100 ± 13 | 80 |
| CNP22 | PEG20K | 0 | 15 | >>160 |
| CNP22 | PEG5K | 8 ± 1 | 20 ± 7 | >>160 |
| CNP22 | PEG2K | 6 ± 2 | 32 ± 4 | >>160 |
| CNP22 | PEO4-(PEO12)$_3$ (branched) | 17 ± 1 | 52 ± 6 | >>160 |
| CNP22 | PEO24 (1.2 kDa) | 8 ± 5 | 46 ± 10 | >>160 |
| CNP22 | PEG1K | 15 ± 3 | 68 ± 17 | >>160 |
| CNP22 | PEO12 (0.6 kDa) | 12 ± 7 | 57 ± 18 | ≧160 |
| CNP22 | (PEO12)-Biotin | 19 | 81 | 140 |
| CNP22, K4G | (PEO12)-Biotin | 10 | 27 | 100 |
| CNP22, K4R | PEO24 | 15 | 56 | ND |
| CNP22, K4R | PEO12 | 13 | 44 | ND |
| CNP-17 | PEG2K | 5 | 50 | >160 |
| R-CNP22, K4R | PEO24 | 15 ± 2 | 75 ± 12 | ND |
| R-CNP22, K4R | PEO12 | 23 ± 2 | 93 ± 19 | ≧160 |
| ER-CNP22, K4R | PEO24 | 6 ± 2 | 60 ± 10 | ND |
| ER-CNP22, K4R | PEO12 | 20 ± 1 | 92 ± 25 | ND |
| GANRR-CNP22, K4R (CNP27) | PEG2K | 15 ± 2 | 45 ± 18 | ND |
| GANRR-CNP22, K4R (CNP27) | PEO24 | 28 ± 9 | 82 ± 18 | >>160 |
| GANRR-CNP22, K4R (CNP27) | PEG1K | 15 ± 0.4 | 56 ± 23 | >>160 |
| GANRR-CNP22, K4R (CNP27) | PEO12 | 40 ± 2 | 99 ± 13 | >>160 |
| GANQQ-CNP22, K4R | PEO24 | 16 ± 13 | 73 ± 30 | ND |
| GANQQ-CNP22, K4R | PEO12 | 30 | 78 | ND |
| GANPR-CNP22, K4R | PEO24 | ND | ND | ND |
| GANPR-CNP22, K4R | PEO12 | ND | ND | 80 |
| GANSS-CNP22, K4R | PEO24 | 8 ± 5 | 46 ± 21 | ND |
| GANSS-CNP22, K4R | PEO12 | 8 ± 0.3 | 52 ± 13 | ND |

[1]Stimulation of cGMP production in NIH3T3 cells by natriuretic peptide relative to cGMP production in the presence of 1 uM CNP22
[2]CNP22 NEP resistance $t_{1/2}$ averaged 80 min. Due to variations in NEP catalytic activity between experiments, all CNP22 $t_{1/2}$ digestions were normalized to 80 min and the difference coefficient was used to calculate analog $t_{1/2}$ in each experiment to obtain an adjusted $t_{1/2}$.
ND = Not Determined FIG. 1 shows the NEP resistance profile of five N-terminal PEGylated conjugates of CNP22. The CNP22 peptides conjugated to PEG (or PEO) polymers of increasing mass exhibited increasing resistance to NEP degradation. In particular, PEO24-CNP22, PEG2K-CNP22 and PEG5K-CNP22 were resistant to NEP degradation over the assay period of 160 minutes.

Figure 2:
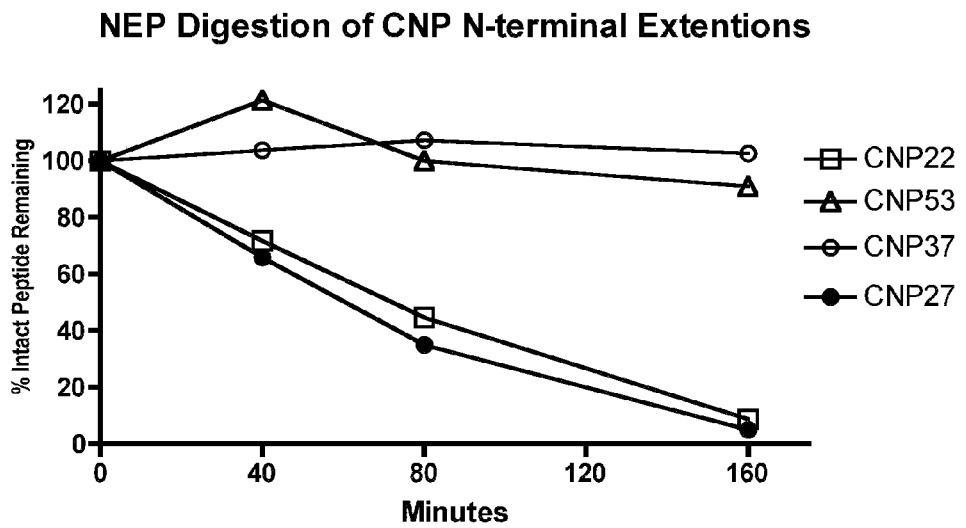
FIG. 2 depicts the degree of NEP resistance of CNP variants having an amino acid extension at the N-terminus. CNP27 in FIG. 2 is CNP27(Arg4), i.e., GANRR-CNP22(K4R).

FIG. 2 displays the NEP resistance profile of CNP variants CNP37, CNP53 and CNP27(Arg4) (i.e., GAN RR-CNP22(K4R)) having an N-terminal amino acid extension. As can be clearly seen, both CNP37 and CNP53 were resistant to NEP degradation in this in vitro assay, whereas CNP27(Arg4) had the same lability to NEP hydrolysis as CNP22.

Figure 3:
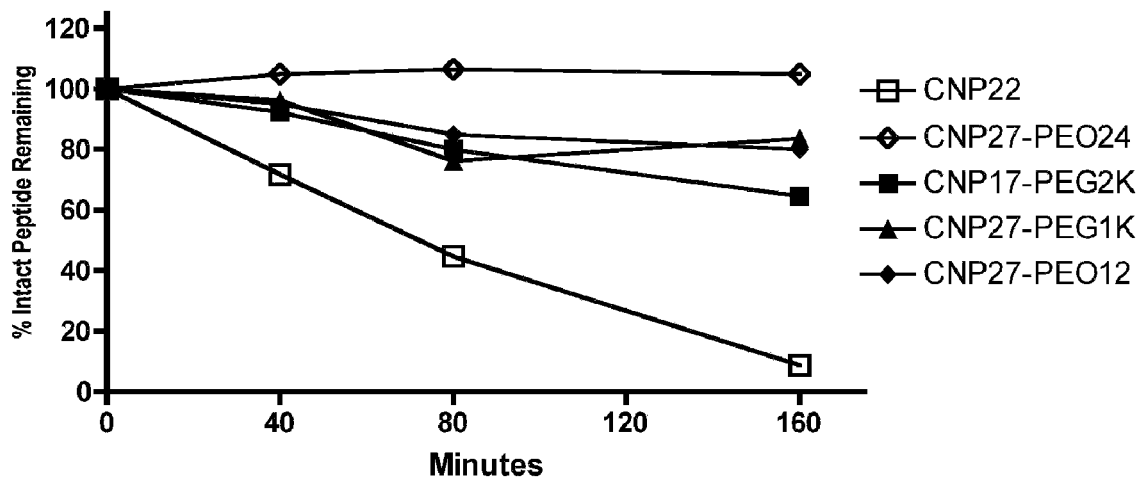
FIG. 3 illustrates the degree of NEP resistance of N-terminal PEGylated CNP17 and CNP27(Arg4).

FIG. 3 depicts the NEP resistance profile of CNP17 and CNP27(Arg4) conjugated to a PEG (or PEO) moiety at the Example 3

CNP Variant Stimulation of cGMP Production in NIH3T3 Cells

To determine the functional activity of CNP variants, the production of GMP was measured in NIH3T3 cells exposed to the CNP variants. Murine NIH3T3 cells express endogenously the CNP signaling receptor, NPR-B, which shares 98% protein sequence identity with human NPR-B. NIH3T3 cells were cultured in high glucose Dulbecco's Modified Eagle Medium supplemented with 10% fetal calf serum and antibiotics at 37° C. with 5% $CO_2$. Twenty four to 48 hours prior to signaling, cells were passaged to 12-well plates with a density of 2-5×10$^5$ cells per well at the time of the assay. CNP variants were resuspended in 1 mM HCl to a stock concentration of 1 mg/mL (455 uM for wtCNP22) and subsequently diluted to a 30 uM working stock solution with phosphate-buffered saline (PBS). Ten-fold serial dilutions were prepared in phosphate-buffered saline. Culture medium was removed from the cells and replaced with 0.4 mL PBS/ Dulbecco's modified Eagle medium (50/50, v/v) containing 0.75 mM isobutylmethylxanine. Plates were incubated at 37° C., 5% $CO_2$ for 15 minutes before addition of 0.2 mL CNP variant in PBS and continued incubation at 37° C. for 15 minutes. Reactions were stopped by the addition of 0.2 mL lysis buffer supplied with the CatchPoint cGMP assay kit (Molecular Devices), and cGMP production was determined with the CatchPoint cGMP Assay (Molecular Devices). All stimulation experiments were performed in duplicate.

Tables 1-4 summarize the ability of CNP variants having backbone or side chain modifications, amino acid substitutions, N-terminal amino acid extensions, and/or N-terminal PEGylation, respectively, to stimulate cGMP production in NIH3T3 cells. In all four tables, the values for cGMP production in NIH3T3 cells exposed to 10 nM or 1 uM CNP variant are normalized to cell number and cGMP production in the presence of 1 uM wtCNP22.

Regarding the results in Table 1, only Analog G having 3-Cl-Phe at position 7 displayed substantially the same NPR-B stimulation activity at 1 uM as wtCNP22. With respect to Table 2, various CNP variants with amino acid substitutions, including Analogs BO, AB, BH, BK, BZ, BX and BR, showed substantially similar NPR-B stimulation activity as wtCNP22. Worthy of note is that Analog AH, which has a K4R substitution, stimulated significantly greater cGMP production than wtCNP22.

Figure 4:
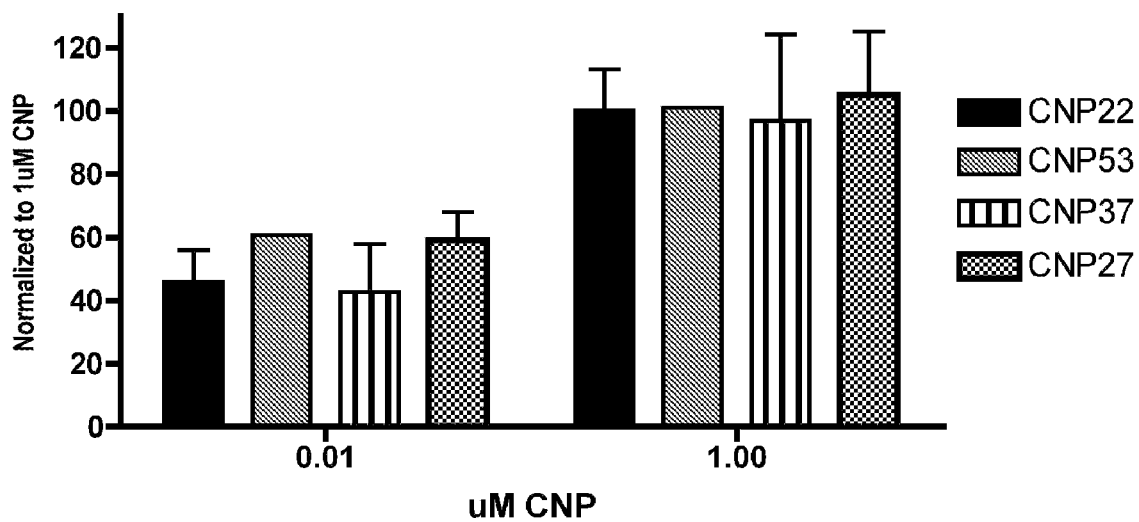
FIG. 4 shows the ability of CNP variants having an N-terminal amino acid extension to stimulate cGMP production in NIH3T3 cells in vitro. The results are relative to the level of cGMP produced in the presence of 1 uM CNP22. CNP27 in FIG. 4 is CNP27(Arg4).

Considering the results in Table 3, many CNP variants having N-terminal and/or C-terminal modifications, including amino acid extensions, exhibited comparable NPR-B stimulation activity as wtCNP22. The functional CNP variants include Analog BB, which is CNP22(G1E) attached to heptanoic acid at the N-terminus, and Analog CD, which is the cyclic domain of CNP22 ("CNP17" retaining the Cys6 to Cys22 sequence) conjugated to the N-terminal and C-terminal "tails" of BNP. FIG. 4 illustrates that CNP27(Arg4) (i.e., GANRR-CNP22(K4R)), CNP37 and CNP53 all had equivalent NPR-B stimulation activity as wtCNP22 in the in vitro assay.

Of note from Table 3 is that among the CNP variants assayed for both CNP functionality and NEP resistance, Analog AZ (R-CNP22(K4R)), Analog CA, Analog CB, Analog CC, Analog CF, Analog BL (CNP37), Analog CE, Analog CS and Analog CD (CNP17 having N- and C-terminal BNP tails) all had comparable NPR-B stimulation activity as CNP22 while being much more resistant to NEP cleavage than CNP22.

Figure 5:
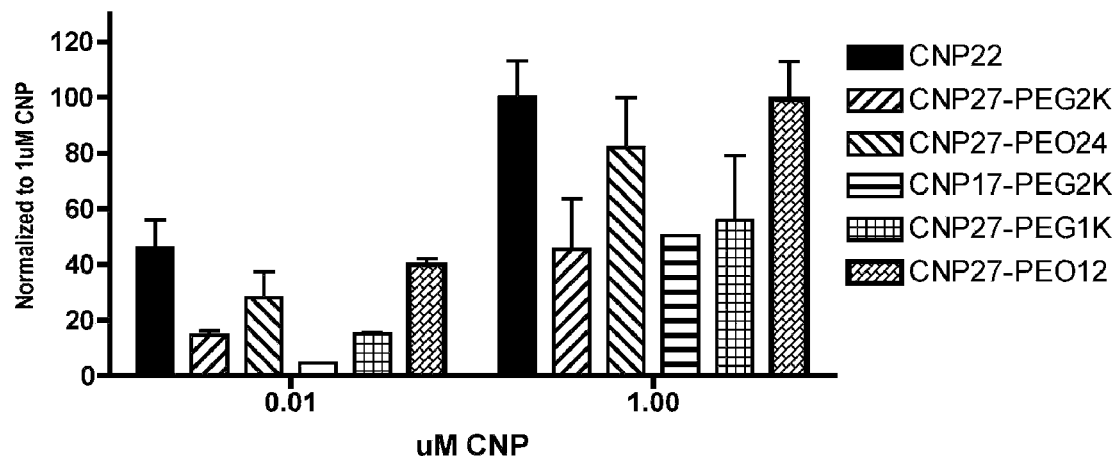
FIG. 5 displays the ability of N-terminal PEGylated CNP17 and CNP27(Arg4) to stimulate cGMP production in NIH3T3 cells.
Figure 6:
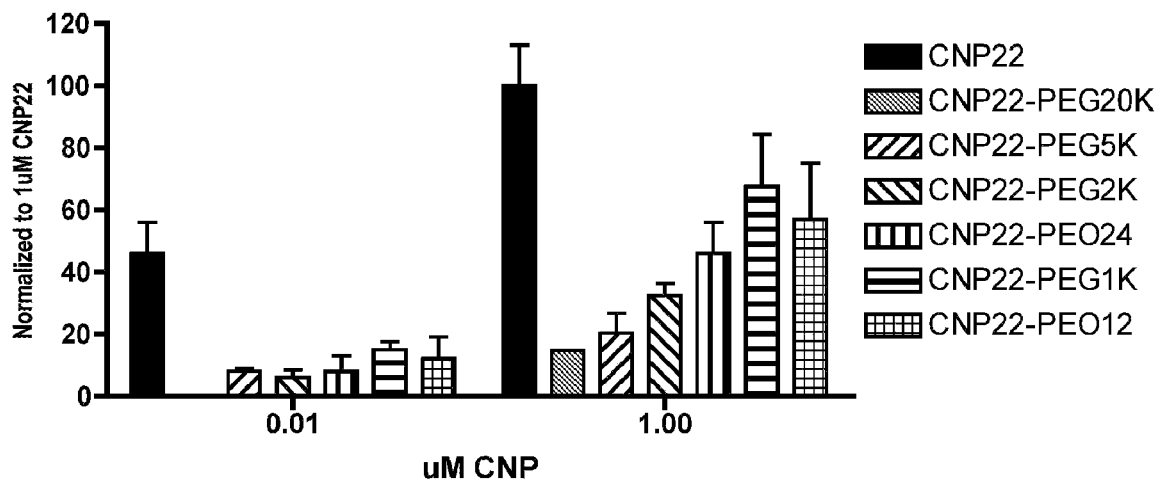
FIG. 6 illustrates the effects of N-terminal PEGylation of CNP22 on cGMP production.

With regard to the results in Table 4, eight N-terminal PEGylated CNP variants at 1 uM stimulated cGMP production to at least 70% of the level achieved by wtCNP22. Several interesting aspects appear in Table 4. First, N-terminal PEGylation of CNP27(Arg4) with a monodispersed PEO polymer (PEO12 is about 0.6 kDa, PEO24 about 1.2 kDa) resulted in significantly better NPR-B functionality than that with a polydispersed PEG polymer (PEG1K has a polymer number average molecular weight ($M_n$) of around 1 kDa, PEG2K around 2 kDa) (see also FIG. 5). Second, N-terminal PEGylation of wtCNP22 with a polydispersed PEG polymer of increasing $M_n$ (PEG1K, PEG2K, PEG5K and PEG20K) or with a monodispersed PEO polymer of greater mass (PEO12 and PEO24) correspondingly decreased the NPR-B activation ability of the CNP variants (see also FIG. 6). Third, PEO24-CNP27(Arg4), having the N-terminal GANRR extension, stimulated significantly greater cGMP production than PEO24-CNP22 and PEO24-CNP22(K4R). Also of note is that among the N-terminal PEGylated CNP variants assayed for both CNP functionality and NEP resistance, PEO12-R-CNP22(K4R), PEO12-CNP27(Arg4) and PEO24-CNP27(Arg4) all had substantially the same NPR-B stimulation activity as CNP22 while being much more resistant to NEP degradation than CNP22.

Example 4

Binding Specificity for NPR-A, NPR-B and NPR-C

Signaling Competition Assay

To determine the binding specificity of CNP variants for the clearance receptor NPR-C, a signaling competition assay is carried out. An expression plasmid for human NPR-C (purchased from OriGene) is transiently expressed in NIH3T3 cells. Twenty-four hours after transfection, NIH3T3 cells are processed for the NPR-B/cGMP stimulation assay described in Example 3. Addition of wtCNP22 is expected to bind to both the endogenous NPR-B and the transiently expressed NPR-C, resulting in decreased cGMP production and a shift in the dose-response curve to the right. CNP variants having reduced affinity for NPR-C are expected not to induce a shift, or to induce a smaller shift, in the dose-response curve.

Alternatively, the relative affinities of CNP variants for NPR-A, NPR-B and NPR-C are determined in a signaling competition assay (U.S. Pat. No. 5,846,932; B. Cunningham, EMBO J. 13(11): 2508-2515 (1994); H. Jin et al., J. Clin. Invest. 98(4): 969-976 (1996)). HEK293T cells, or another suitably transfectable cell line (e.g., HeLa cells, HEK293 cells, etc) are transiently transfected with expression plasmids for NPR-A (OriGene) or NPR-B (cDNA cloned with standard molecular biology techniques into pcDNA3.1 (Invitrogen)) with or without NPR-C (OriGene).

Determination of Binding Affinities ($K_i$) for NPR-A, NPR-B and NPR-C

The binding affinities ($K_i$) of CNP variants for NPR-A, NPR-B and NPR-C are determined in a heterologous competition binding assay (U.S. Pat. No. 5,846,932; B. Cunningham, EMBO J. 13(11): 2508-2515 (1994); H. Jin et al., J. Clin. Invest. 98(4): 969-976 (1996)). Membranes from HEK293 cells, or another suitably transfectable cell line (e.g., HeLa cells), expressing human NPR-A, NPR-B or NPR-C are prepared for radio-labeled ligand binding assays. Membrane preparations are diluted in an appropriate buffer and varying concentrations of wtCNP22 or CNP variant (competitor) are added with $I^{125}$-labeled wtCNP22 (Bachem). Samples are incubated at room temperature to allow for ligand/receptor equilibration and bound peptide is separated from free peptide by filtration through PVDF filter membranes. Filters are washed before the addition of scintillant and counting by a scintillation counter. Binding is measured in duplicate for each concentration of competitor peptide. CNP variant affinity ($K_i$, equilibrium dissociation constant) and $B_{max}$ (receptor number) are calculated by non-linear regression analysis and/or the Cheng-Prusoff equation.

Example 5

Effect of CNP Variants on the Growth of Rat Chondrosarcoma (RCS) Cells and cGMP Production in RCS Cells To assess the ability of CNP variants to stimulate bone growth, skeletal dysplasia is simulated in cell culture by treating rat chondrosarcoma (RCS) cells with fibroblast growth factor 2 (FGF-2), which activates fibroblast growth factor receptor 3 (FGFR-3) and induces growth arrest (Krejci et al., J. Cell Sci., 118(21):5089-5100 (2005)).

Optimal CNP treatment parameters are determined by varying CNP concentration (0.05, 0.1, 0.2 and 0.5 uM), and treatment duration and interval (continuous; 2.5 min, 10 min, 30 min, 1 hr, 2 hr, 4 hr and 8 hr once a day; 2.5 min, 10 min, 30 min, 1 hr, 2 hr and 4 hr twice a day). After 72 hours, cells are counted using an automated cell counter, and the amount of extracellular matrix is estimated using alcian blue staining.

RCS cells are then treated with a CNP variant using the optimal conditions determined from the growth experiments with wtCNP22. The concentration of cGMP is measured by competitive ELISA for untreated RCS cells, RCS cells treated with CNP, and RCS cells treated with the CNP variant. Cell growth and matrix synthesis resulting from treatment with the CNP variant are also monitored and compared to those resulting from CNP treatment.

To assess the effect of CNP variants in a human cell culture system, primary re-differentiated human chondrocytes in alignate beads are treated with wtCNP22 and CNP variants, and cGMP concentration is determined by competitive ELISA as a measure of effective CNP signaling.

The methods described herein can be employed to assess the ability of CNP variants to stimulate cGMP production in and growth of rat chondrosarcoma cells in vitro.

Example 6

Dose Response Study in Rat Chondrosarcoma Cells

The tyrosine kinase receptor fibroblast growth factor receptor 3 (FGFR-3), a negative regulator of chondrocyte growth, is contitutively on in achondroplasia subjects. Continuous exposure of rat chondrosarcoma (RCS) cells to fibroblast growth factor 2 (FGF-2) simulates achondroplasia in cell culture by activating FGFR-3 and inducing growth arrest (Krejci et al., J. Cell Sci., 118(21): 5089-5100 (2005)). To determine the dose of CNP variant and frequency of dosing that stimulate sufficient growth of bone cells, a dose response study was performed using the RCS cell assay as described in Example 5.

RCS cells were seeded at $10 \times 10^3$ cells per well in 24-well plates, grown for 24 hr, treated for 72 hr, and then counted. RCS cells were continuously exposed to FGF-2 (5 ng/mL) to simulate a constitutively active FGFR-3, which induced cell growth arrest (see bar #5 in FIG. 7). Wild-type CNP22 (0.2 uM) was cultured continuously (72 hr), 1 hr daily or 2 hr daily. All stimulants were changed daily. Continuous exposure of RCS cells to 0.2 uM CNP22 in the presence of 5.0 ng/mL FGF-2 partially reversed FGF2-induced growth arrest, leading to the growth of approximately $200 \times 10^3$ cells per well (bar #6 in FIG. 7), compared to approximately $100 \times 10^3$ cells per well in the absence of CNP22 (bar #5 in FIG. 7).

Figure 7:
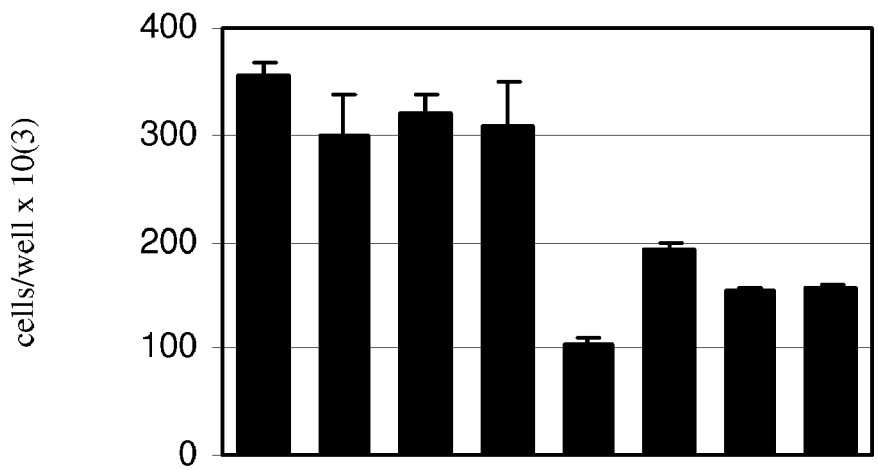
FIG. 7 demonstrates that exposure of rat chondrosarcoma cells to CNP22 1 hour once daily or 2 hours once daily has substantially similar effectiveness in reversing FGF2-induced arrest of chondrocyte growth as continuous exposure to CNP22.

Both 1 hr exposure to CNP22 (0.2 uM) once a day and 2 hr exposure to CNP22 (0.2 uM) once a day achieved about 84% of the effect of continuous CNP22 (0.2 uM) exposure on chondrocyte growth (bars #7 and 8 in FIG. 7). These results demonstrate that continuous exposure of growth-arrested chondrocytes to CNP22 is not required for reversal of cell growth arrest. Furthermore, histological and cell morphological analysis of the extracellular matrix showed that CNP22 treatment antagonized FGF2-mediated loss of chondrosarcoma extracellular matrix and increased matrix synthesis (data not shown).

Similar dose response studies can be conducted with the CNP variants described herein to determine their effective dose for reversing FGF2-induced growth arrest of RCS cells.

Example 7

Ex Vivo Studies on Stimulation of Tibial and Femoral Growth

Mouse tibial organ culture model has been used to demonstrate the efficacy of wild-type CNP22 in stimulating longitudinal bone growth. Treatment of wild-type tibiae with CNP22 at $10^{-8}$, $10^{-7}$ or $10^{-6}$ M for 6 days increased longitudinal growth by 31%, 40% and 42%, respectively. Histological evaluation also showed expansion of the hypertrophic zone, e.g., an increase in the number and size of hypertrophic chondrocytes in the growth plate (Agoston et al., BMC Dev. Biol. 7:18 (2007)). Similar findings were observed in tibiae isolated from $FGFR3^{Ach}$ mice (Yasoda et al., Nat. Med. 10: 80-86 (2004)).

To determine the efficacy of CNP variants in stimulating longitudinal bone growth, CNP variants are tested in a mouse organ culture model of endochondral bone growth in wild-type and $FGFR3^{wt/Ach}$ (heterozygote) mice. In brief, the pharmacological activity of wild-type CNP22 and CNP variants is compared in an organ culture model of embryonic or neonatal mouse tibiae, isolated from wild-type and $FGFR3^{wt/Ach}$ littermates. Overall bone growth and histological changes within the growth plate are assessed. Conditioned culture medium is assessed for CNP, as well as biomarkers of intracellular signaling (cGMP), cartilage metabolism (type II collagen, other collagens, aggrecan, chondroitin sulfate), bone metabolism (bone alkaline phosphatase, osteocalcin, type I collagen [C-telopeptide, N-telopeptide]), and inflammation (interleukin-1, interleukin 6, interleukin-11). In addition, the effects of various treatment regimens of wild-type CNP22 are compared to determine the optimal conditions to enhance longitudinal bone growth.

Effective CNP variants are identified by their ability to stimulate production of cGMP, and bone growth as measured by increased longitudinal bone length and expansion of the cells in the hypertrophic zone of the growth plate.

The efficacy of wtCNP22, CNP37 and PEO24-CNP27 (Arg4) (i.e., PEO24-GANRR-CNP22(K4R)) in stimulating longitudinal femoral growth was evaluated in the mouse organ culture model. For these experiments femora were isolated from 2-3 day old wild-type mice and cultured in alphaMEM supplemented with 0.2% BSA, 0.5 mM L-glutamine, 40 units penicillin/mL and 40 ug streptomycin/mL, for 8 days in the presence of vehicle, CNP22 or CNP variants. The treatment commenced at day 0 and was repeated every two days thereafter, as the medium was changed. Bones were measured prior to treatment and every two days thereafter, using a dissection microscope fitted with a 1 cm eyepiece reticule. Conditioned medium was used for biomarker analysis. At day 8 bones were fixed in 4% paraformaldehyde for 24 hr, decalcified in 5% formic acid for 24 hrs, dehydrated and embedded in paraffin. Bones were sectioned at 5 um (microns), which were then deparaffinized, rehydrated, and stained with Alcian Blue for 30 min (pH 2.5; MasterTech) and van Gieson (EM Sciences) for 5 min. Alcian Blue stains cartilage blue and van Gieson stains osteoid (unminerlized bone) red. Stained sections were visualized and photographed by brightfield microscopy. The thickness of the hypertrophic region of the growth plate cartilage was determined by image analysis.

Figure 8:
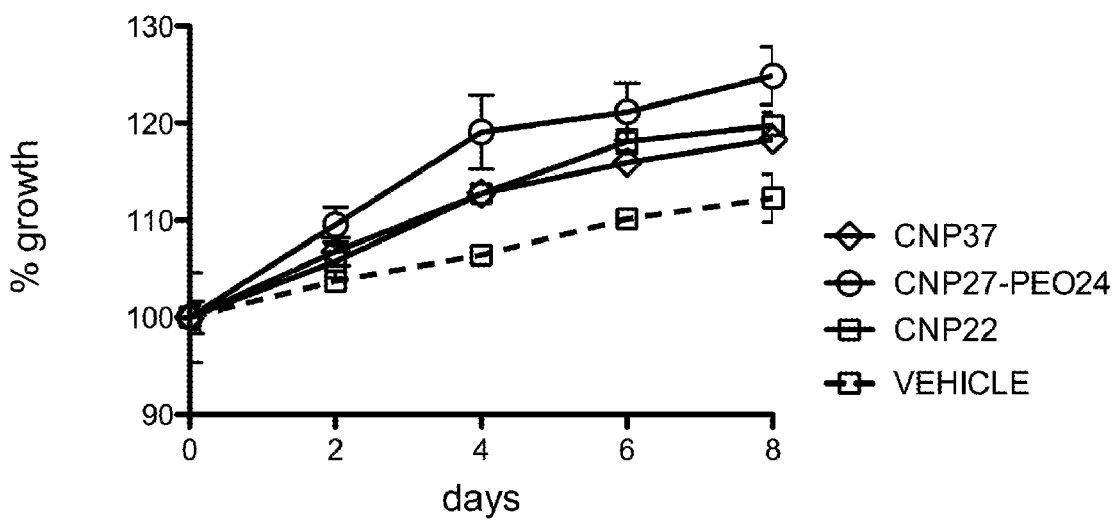
FIG. 8 shows the efficacy of CNP37 and PEO24-CNP27 (Arg4) in stimulating longitudinal growth of wild-type femur in an ex vivo mouse organ model.

FIG. 8 illustrates the effect of wtCNP22, CNP37 and PEO24-CNP27(Arg4) on longitudinal growth of 3-day old wild-type femurs treated with the CNP peptides every two days. The results were normalized to measurements prior to treatment (day 0). The studies were performed in triplicate (vehicle) or quadruplicate (CNP peptides). As shown in FIG. 8, CNP37 and PEO24-CNP27(Arg4), as well as CNP22, were effective in stimulating longitudinal femoral growth, with the N-terminal PEGylated CNP variant being the most effective.

Example 8

Serum/Plasma Stability of CNP Variants In Vitro

In preparation for pharmacokinetics (PK) studies, the stability of CNP variants in serum and/or plasma is evaluated.

Briefly, the analyte is isolated by the removal of serum or plasma proteins by either a 2% trichloroacetic acid precipitation or a 1:3 serum:acetonitrile precipitation. The precipitation mixture is vortexed at 14,000 rpm for five minutes, and a portion of the supernatant is removed and diluted with water prior to transfer to a silanized autosampler vial for analysis. Serum extracts are then analyzed by reverse-phase high performance liquid chromatography (RP-HPLC) with electrospray ionization mass spectrometry (ESI-MS). A single mass (m/z), shown to be specific for the CNP variant, is monitored for quantitation purposes.

Initially, analytical stability and recovery is determined. Analytical (RP-HPLC and ESI-MS) parameters are optimized through the analysis of matrix standards (serum extracts fortified with analyte post-precipitation). After optimization, analytical recovery is determined by spiking serum samples at known concentrations and comparison of the analyte response to that of matrix standards prepared at similar concentrations. Analyte stability in serum extracts is also determined to assure no significant losses occur after serum precipitation and prior to actual analysis. To test the effect of freezing on serum stability, a two-cycle freeze/thaw study is also performed. In this study a serum sample is spiked with CNP variant and analyzed prior to freezing overnight at $-20°$ C. The sample is then thawed at room temperature and re-analyzed. The process is repeated for a second freeze/thaw cycle.

Serum stability of CNP variant is determined by spiking of serum/plasma samples with CNP variant at a concentration of 10 ug/mL. The sample is placed in a 37° C. water bath for a period of three hours. At 30 minute intervals duplicate aliquots of serum are removed and analyzed. If rapid losses of analyte are evident (>50% in 30 minutes), the study may be repeated with 10 minute timepoints.

In an exemplary method for determining the stability of CNP variants in murine plasma, a mixture of CNP variant (10 uL of a stock solution of about 2.5-5.0 mg/mL), heparinized murine plasma (50 uL, Bioreclamation, CD-1 Lith Hep 62231), and 5 M NaCl (10 uL) is incubated at 37° C. and 5% $CO_2$ for 0-5 hr, and then quenched with 10× protease inhibitor cocktail (15 uL, Sigma P2714). For extraction, 150 uL of MeOH/0.1% FA is added to 85 uL of the reaction mixture, and the resulting mixture is vortexed for 1 min and then centrifuged at 15° C. for 15 min. 75 uL of the supernatant is added to 300 uL of aqueous 0.1% FA. A small portion of the resulting mixture is subjected to analysis by LC/MS.

Example 9

Pharmacokinetics and cGMP Production in Rats and Mice

Studies were conducted in normal rats to evaluate the pharmacokinetics (PK) profile of CNP22 and certain CNP variants and the time courses of plasma cGMP concentration after single intravenous (i.v.) or subcutaneous (s.c.) administration of the CNP peptides. Plasma CNP immunoreactivity was determined by using a competitive radioimmunoassay (RIA) with an anti-CNP rabbit polyclonal antibody. Plasma cGMP concentration was determined by RIA using a commercially available kit (YAMASA cyclic GMP Assay kit, YAMASA Corporation).

Normal male rats, 7-8 weeks of age, were used. Recombinant wild-type CNP22, CNP37 and PEO24-CNP27(Arg4) (i.e., PEO24-GANRR-CNP22(K4R)) were evaluated. A dosage of 20 nmol/kg of each CNP peptide as a solution in 5% mannitol was intravenously injected once into the tail, or a dosage of 50 nmol/kg of each CNP peptide as a solution in 0.03 mol/L acetic acid buffer solution, pH 4.0, containing 1% (w/v) benzyl alcohol and 10% (w/v) sucrose, was subcutaneously injected once into the back.

Plasma CNP immunoreactivity was determined by the competitive RIA using anti-CNP rabbit polyclonal antibody. Standard and QC samples were prepared. Fifty uL of the standard, QC and assay samples were added, respectively, to test tubes containing 50 uL of RIA buffer. Diluted anti-CNP rabbit polyclonal antibody (100 uL) was added to the tubes. All tubes were kept at 4° C. overnight. $^{125}$I-[Tyr$^0$]-CNP22 solution (100 uL) and rabbit IgG solution (100 uL) were added and left at approximately 4° C. overnight. One milliliter of anti-rabbit IgG goat serum containing 10% polyethylene glycol was added, vortexed and left at approximately 4° C. for at least 1 hour, and then the insoluble fraction was precipitated by centrifugation. After aspiration of the supernatant, the amount of radiation (gamma line) in the sediment was measured by a gamma-counter. Each sample was measured in duplicate, and the mean was adopted as the value determined.

Plasma cGMP concentrations in the sample at 5, 30, 60 and 90 minutes after i.v. dosing, or at 5, 30, 60, 120 and 180 minutes after s.c. dosing, were determined by the competitive RIA using anti-cGMP monoclonal antibody. Standard samples were prepared. 100 uL of the assay samples (standard solutions for the calibration curve or the diluted plasma samples for cGMP determination) were transferred to test tubes. Then 100 uL of anti-cGMP monoclonal antibody solution and 100 uL of $^{125}$I-labeled succinyl cGMP tyrosine methyl ester solution were added to the tubes, respectively. All tubes were kept at 4° C. overnight. After the addition of 500 uL dextran charcoal solution, the tubes were vortexed and then placed on ice for 10 minutes. The reaction mixture was centrifuged and 500 uL of the supernatant was transferred from each sample to a new test tube. The amount of radiation (gamma line) in the supernatant was measured by a gamma-counter. Each sample was measured in duplicate, and the mean was adopted as the value determined.

Plasma CNP immunoreactivity was employed for pharmacokinetics (PK) analysis. PK analysis was performed using WINNONLIN® Professional (Pharsight Corporation). The PK profiles of CNP22, CNP37 and PEO24-CNP27(Arg4) after i.v. administration were calculated using PK parameters such as concentration at 0 hour ($C_0$: extrapolation, pmol/mL), total body clearance ($CL_{tot}$: mL/min/kg), distribution volume at steady state ($V_{dss}$: mL/kg), area under the plasma concentration-time curve (AUC: pmol·min/mL), mean residence time (MRT: min), and half-life ($T_{1/2}$: min). The PK profiles of the CNP peptides after s.c. administration were calculated using PK parameters such as maximum plasma concentration ($C_{max}$: pmol/mL), time to reach $C_{max}$ ($T_{max}$: min), area under the plasma concentration-time curve (AUC: pmol·min/mL), mean residence time (MRT: min), and half-life ($T_{1/2}$: min).

In plasma spike recovery experiments, the RIA detected CNP22, CNP37 and PEO24-CNP27(Arg4) similarly (data not shown).

Procedures similar to those described above are employed to study in mice the PK profiles of CNP22 and variants thereof and their ability to stimulate cGMP production.

Figure 9:
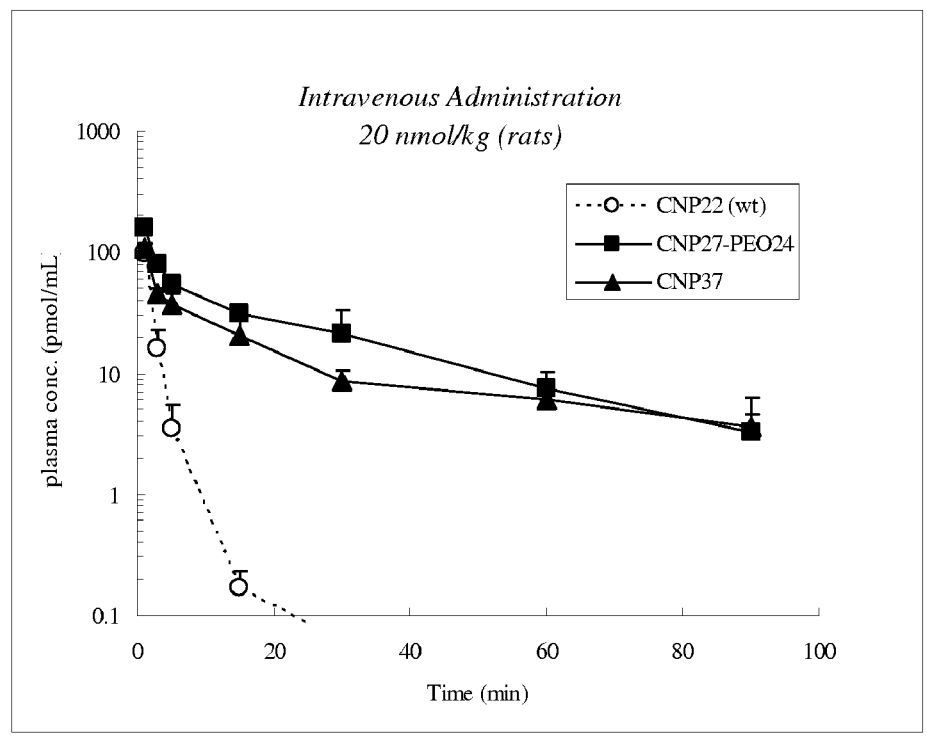
FIG. 9 shows that CNP37 and PEO24-CNP27(Arg4) intravenously (i.v.) administered to rats have a much longer half-life and a much greater bioavailability in the plasma than CNP22.

The PK profiles of CNP22, CNP37 and PEO24-CNP27 (Arg4) after i.v. administration in three rats are illustrated in FIG. 9. As shown by FIG. 9, CNP37 and PEO24-CNP27 (Arg4) had a much longer half-life and a much greater bioavailability than CNP22. The half-life, $T_{1/2}$ (min), is 1.42 (±0.45) for CNP22, 22.3 (±1.5) for PEO24-CNP27(Arg4), and 49.5 (±28.0) for CNP37. The area under the curve, AUC (pmol·min/mL), is 320 (±54) for CNP22, 1559 (±568) for CNP37, and 2084 (±424) for PEO24-CNP27(Arg4).

Figure 10:
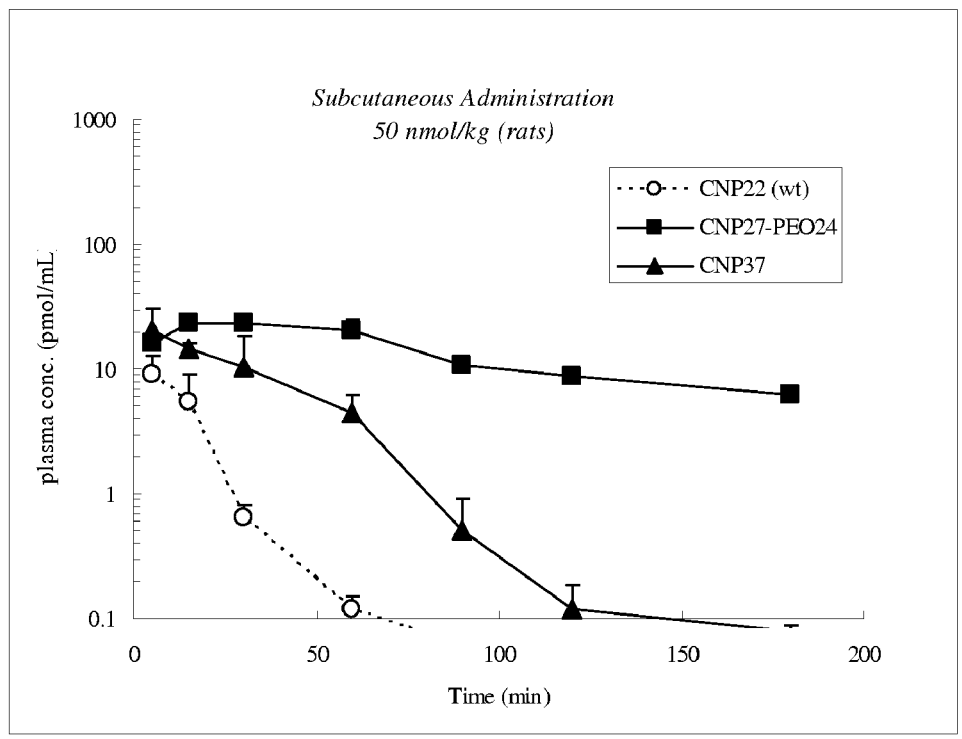
FIG. 10 illustrates that PEO24-CNP27(Arg4) subcutaneously (s.c.) administered to rats also has a much longer half-life and a much greater bioavailability in the plasma than CNP22.

The PK profiles of the three CNP peptides after s.c. administration in three rats are depicted in FIG. 10. Compared to CNP22, PEO24-CNP27(Arg4) had a much longer half-life (78.1 min (±16.4) vs. 10.0 (±5.0)) and a much greater bioavailability (60% (±6%) vs. 19% (±9%)).

Figure 11:
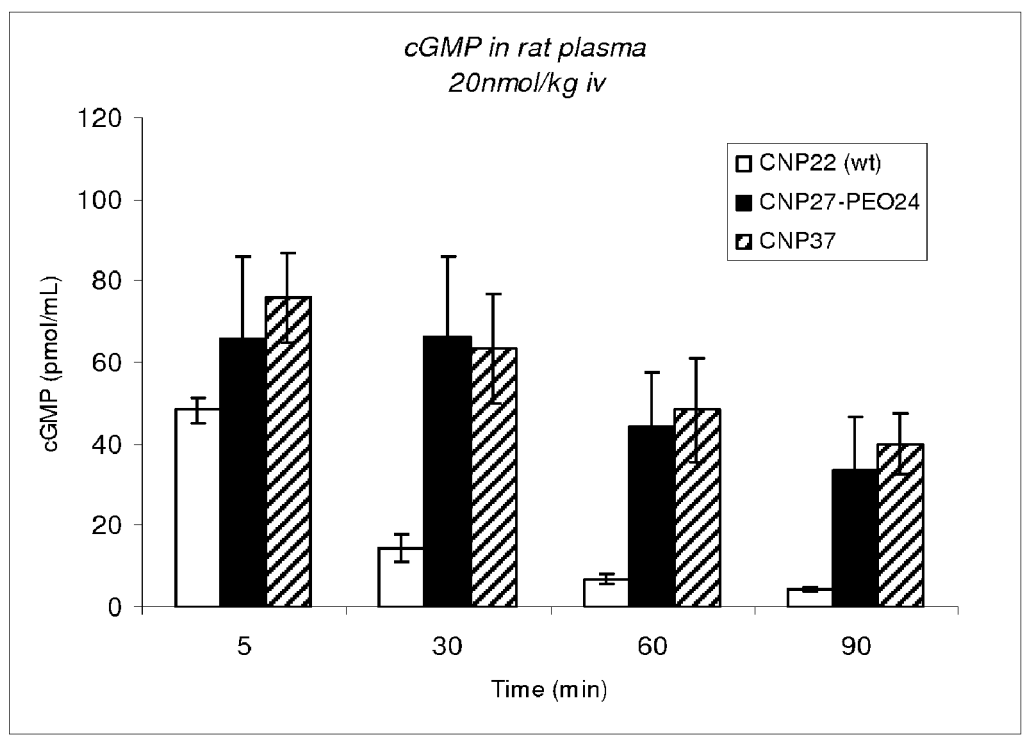
FIG. 11 demonstrates that i.v. administered CNP37 and PEO24-CNP27(Arg4) stimulate a much greater level of cGMP production in rats than CNP22.

The time courses of plasma cGMP concentrations after i.v. administration of the three CNP peptides in three rats are displayed in FIG. 11. FIG. 11 clearly demonstrates that i.v. administration of CNP37 and PEO24-CNP27(Arg4) resulted in much higher plasma levels of cGMP at 30, 60 and 90 minutes than i.v. administration of CNP22.

Figure 12:
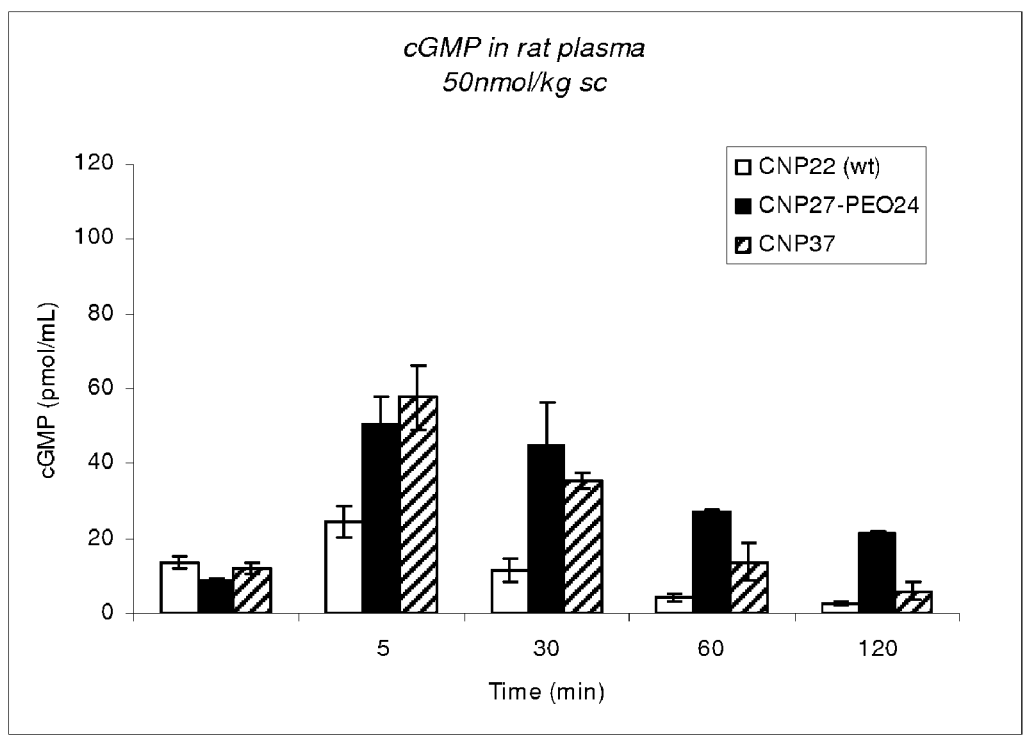
FIG. 12 shows that s.c. administered PEO24-CNP27 (Arg4) and, to a lesser extent, CNP37 are substantially more effective in stimulating cGMP production in rats than CNP22.

The time profiles of plasma cGMP concentrations after s.c. administration of the three CNP peptides in three rats are shown in FIG. 12. Subcutaneous administration of PEO24-CNP27(Arg4) and CNP37 also resulted in substantially higher plasma concentrations of cGMP than s.c. administration of CNP22, with the difference relative to CNP22 increasing over time for PEO24-CNP27(Arg4), but decreasing over time for CNP37.

The rat studies indicate that compared to wtCNP22, the CNP variants CNP37 and PEO24-CNP27(Arg4) had a substantially longer half-life in vivo, had a substantially greater bioavailability in vivo, and stimulated substantially higher levels of cGMP production in vivo for an extended period of time. The resistance of CNP37 and PEO24-CNP27(Arg4) to NEP degradation correlates to a longer plasma half-life in vivo, which in turn correlates to prolonged NPR-B/cGMP signaling in vivo. These results show that unlike CNP22, the CNP variants of the invention, administered by i.v. or s.c. injection (e.g., once daily), can potentially be effective in treating CNP-responsive conditions or disorders, such as bone-related disorders and vascular smooth muscle disorders.

Example 10

Pharmacokinetics Study in Mice

To determine CNP variants having increased NEP resistance, for efficacy study in FGFR3$^{ach}$ mice (see Example 11), a pharmacokinetics (PK) study is carried out that compares the pharmacokinetics properties of CNP variants to wild-type CNP22. The FGFR3$^{ach}$ mouse is a mutant mouse model of achondroplasia, containing a single transgene on a background of FVB mice.

Wild-type CNP22 or variant thereof is administered as a single intravenous (i.v.) dose in 6-week old wild-type FVB mice. Exemplary PK studies were conducted using wtCNP22. Six-week old FVB/N mice were intravenously administered wtCNP22 in a single dose at 100 nmol/kg. Mean plasma levels of CNP22 were calculated, and the estimated half-life of CNP22 was determined to be from 0.76 min to 1.03 min.

CNP variants displaying greater resistance to NEP degradation are expected to exhibit increased serum concentrations over time and a longer half-life in vivo.

Example 11

Efficacy in Mouse Model of Achondroplasia

The efficacy of CNP22 and variants thereof in enhancing growth and correcting achondroplasia is tested in a mouse model of achondroplasia, using a strain of transgenic mice expressing the mutated human FGFR-3 gene (FGFR3$^{ach}$) (Wang et al., Proc. Natl. Acad. Sci. USA, 96(8): 4455-4460 (1999); Naski et al., Development USA, 125: 4977-4988 (1998); U.S. Pat. Nos. 6,265,632 and 6,136,040).

At 3 weeks of age, FGFR3$^{ach}$ mice and their wild-type littermates are anesthetized by 2.5% Avertin to have lateral whole-body X-ray images taken by Faxitron, and randomized by body weight into the following treatment groups (n=8/group): (1) wild-type/vehicle, (2) FGFR3$^{ach}$/vehicle, (3) FGFR3$^{ach}$/CNP22, (4) FGFR3$^{ach}$/first CNP variant, (5) FGFR3$^{ach}$/second CNP variant, and (6) FGFR3$^{ach}$/third CNP variant. Mice undergo once daily subcutaneous administration of designated test article for 5 weeks. Satellite groups (n=3) are used to confirm exposure of each test article following a single subcutaneous administration on Day 1.

On Day 37, all mice are sacrificed by terminal anesthesia and whole-animal photographs and X-ray images by Faxitron are taken. Left and right tibia, femur, humerus, and ulna are collected and measured using a digital caliper. The left portions of each bone are processed for histology, and the right portions are snap-frozen for archival. Samples obtained from the bones are used to evaluate and compare the effects of CNP22 and CNP variants on endochondral bone growth.

Example 12

Clinical Evaluation of CNP Variants

The following example provides guidance on the parameters to be used for the clinical evaluation of compositions comprising CNP22 or variants thereof in the therapeutic methods of the present invention. As discussed herein, CNP22 or variants thereof will be used in the treatment of disorders responsive to CNP, including disorders of the bone and vascular smooth muscle. Clinical trials will be conducted which will provide an assessment of doses of CNP22 or variants thereof for safety, pharmacokinetics, and initial response of both surrogate and defined clinical endpoints. The trial will be conducted for a minimum, but not necessarily limited to, 24 weeks to collect sufficient safety information on about 100 evaluable patients. The initial dose for the trials will vary from about 0.001 to about 1.0 mg/kg/week. In the event that the initial dose in this range does not produce a significant direct clinical benefit, the dose should be increased within this range or beyond this range as necessary, and maintained for an additional minimal period of, but not necessarily limited to, 24 weeks to establish safety and to evaluate efficacy further.

Measurements of safety will include adverse events, allergic reactions, complete clinical chemistry panel (including kidney and liver functions), urinalysis, and CBC with differential. In addition, other parameters relevant to clinical benefit will be monitored. The present example also includes the determination of pharmacokinetic parameters of CNP22 or variants thereof, including absorption, distribution, metabolism, excretion, and half-life and bioavailability in the blood. It is anticipated that such analyses will help relate dose to clinical response.

Methods

Patients will undergo a baseline medical history and physical exam, and a standard set of clinical laboratory tests (including CBC, Panel 20, CH50, and UA). The patients will be followed closely with weekly visits to the clinic. The patients will return to the clinic for a complete evaluation one week after completing the treatment period. Should dose escalation be required, the patients will follow the same schedule outlined above. Safety will be monitored throughout the trial.

Diagnosis and Inclusion Criteria

The patients may be male or female, with a documented diagnosis of a potentially CNP-responsive disorder. A specific example of a potentially CNP-responsive, bone-related disorder is achondroplasia, which may be confirmed by genetic testing and other evidence of an FGFR-3 mutation or dysfunction. The ideal age range of achondroplasia patients will be from infant (<1 year of age) to pre-adolescent (<13 years of age). A patient will be excluded from this study if the patient is pregnant or lactating; has received an investigational drug within 30 days prior to study enrollment; or has a medical condition, serious intercurrent illness, or other extenuating circumstance that may significantly decrease study compliance.

Safety

Therapy with CNP22 or variants thereof will be determined to be safe if no significant acute or chronic drug reactions occur during the course of the study. The longer-term administration of the drug will be determined to be safe if no significant abnormalities are observed in the clinical examinations, clinical labs, or other appropriate studies.

It has been shown that compared to wild-type CNP22, certain CNP variants of the invention are much more resistant to NEP degradation in vitro, have a much longer plasma half-life and bioavailability in rats, stimulate a much higher level of cGMP production in rats, and induce a greater amount of bone growth of the femur from wild-type mice. Furthermore, it has been shown that short duration dose regimen treatments with CNP22 are nearly as effective as continuous CNP22 treatment in reversing FGF2-induced arrest of chondrocyte growth in vitro. These results demonstrate the potential use of CNP variants of the invention in treating CNP-responsive conditions or disorders such as, e.g., bone-related disorders and vascular smooth muscle disorders.

It is understood that every embodiment of the invention described herein may optionally be combined with any of the other embodiments described herein. Every patent literature and every non-patent literature cited herein are incorporated herein by reference in their entirety.

Numerous modifications and variations to the invention, as set forth in the embodiments and illustrative examples described herein, are expected to occur to those skilled in the art. Consequently only such limitations as appear in the appended claims should be placed on the invention.

What is claimed is:

1. A variant of C-type natriuretic peptide (CNP) having a total mass in the range from about 2.6 kDa to about 7.0 kDa, and having the formula:

(SEQ ID NO: 35)
(x)-Gly$_1$-Leu$_2$-Ser$_3$-(Arg)$_4$-Gly$_5$-(Cys)$_6$-(Phe)$_7$-(Gly)$_8$-

(Leu)$_9$-(Lys)$_{10}$-(Leu)$_{11}$-Asp$_{12}$-Arg$_{13}$-(Ile)$_{14}$-(Gly)$_{15}$-

Ser$_{16}$-(Met)$_{17}$-Ser$_{18}$-Gly$_{19}$-(Leu)$_{20}$-Gly$_{21}$-Cys$_{22}$-(z)

(x) is an amino acid sequence comprising from 1 to 40 amino acids and is optionally conjugated with a PEG polymer or a derivative thereof at the N-terminus of the variant; and (z) may be absent or may be selected from the group consisting of bone- or cartilage-targeting moieties; moieties that reduce renal clearance; hydrophilic polymers; amino acid sequences comprising one or more amino acids; carbohydrates;

hydrophobic acids; and combinations thereof.

2. The CNP variant of claim 1, wherein the bone- or cartilage-targeting moieties are selected from the group consisting of bisphosphonates;

hydroxyapatite; glucosamine; collagen type X; polyAsp; polyGlu; and amino acid sequences derived from bone-targeting domains of osteocrin, osteopontin, osteocalcin, and sialoprotein.

3. The CNP variant of claim 1, wherein the moieties that reduce renal clearance are hydrophilic polymers comprising at least one functional group that is negatively charged under physiological conditions.

4. The CNP variant of claim 1, wherein for (z) the amino acid sequences comprising one or more amino acids are derived from natriuretic polypeptides or non-natriuretic polypeptides, and wherein the amino acid sequences may optionally comprise amino acid addition(s), deletion(s), and/or substitution(s) relative to the wild-type sequences of the natriuretic polypeptides or non-natriuretic polypeptides.

5. The CNP variant of claim 4, wherein the natriuretic polypeptides are selected from the group consisting of CNP-22, CNP-53, Natriuretic Peptide Precursor C (NPPC), atrial natriuretic peptide (ANP), Natriuretic Peptide Precursor A (NPPA), brain natriuretic peptide (BNP), and Natriuretic Peptide Precursor B (NPPB).

6. The CNP variant of claim 4, wherein the non-natriuretic polypeptides are selected from the group consisting of albumin, immunoglobulins, histine-rich glycoproteins (HRGPs), fibronectin, fibrinogen, zinc finger-containing polypeptides, fibroblast growth factor 2 (FGF-2), and bone morphogenetic proteins (BMPs).

7. The CNP variant of claim 1, wherein for (z) the amino acid sequences comprising one or more amino acids comprise from 1 to 40 amino acids.

8. The CNP variant of claim 1, wherein the hydrophobic acids are selected from the group consisting of natural fatty acids and linear or branched, saturated or unsaturated $C_5$-$C_{12}$ carboxylic acids.

9. The CNP variant of claim 1, wherein the variant comprises an Arg residue immediately preceding the position corresponding to Gly1 of CNP-22.

10. A variant of C-type natriuretic peptide (CNP) comprising the amino acid sequence set out in SEQ ID NO:35 (CNP22K4R) which is selected from the group consisting of:

```
                                  (SEQ ID NO: 41)
R-CNP22(K4R) (Analog AZ);

(SEQ ID NO: 39)
ER-CNP22(K4R) (Analog BA);

(SEQ ID NO: 69)
GANQQ-CNP22(K4R) (Analog CH);

(SEQ ID NO: 70)
GANSS-CNP22(K4R) (Analog CG);

(SEQ ID NO: 84)
GQPREPQVYTGANQQ-CNP22(K4R) (Analog CK);

(SEQ ID NO: 85)
GVPQVSTSTGANQQ-CNP22(K4R) (Analog CL);

(SEQ ID NO: 87)
GQTHSSGTQSGANQQ-CNP22(K4R) (Analog CN);

(SEQ ID NO: 86)
GQPSSSSQSTGANQQ-CNP22(K4R) (Analog CM);

(SEQ ID NO: 88)
GSTGQWHSESGANQQ-CNP22(K4R) (Analog CO);

(SEQ ID NO: 89)
GSSSSSSSSSGANQQ-CNP22(K4R) (Analog CP);

(SEQ ID NO: 41)
PEO12-R-CNP22(K4R);

(SEQ ID NO: 41)
PEO24-R-CNP22(K4R);

(SEQ ID NO: 39)
PEO12-ER-CNP22(K4R);

(SEQ ID NO: 39)
PEO24-ER-CNP22(K4R);

(SEQ ID NO: 36)
PEG1K-GANRR-CNP22(K4R);

(SEQ ID NO: 36)
PEO12-GANRR-CNP22(K4R);

(SEQ ID NO: 36)
PEO24-GANRR-CNP22(K4R);

(SEQ ID NO: 70)
PEO12-GANSS-CNP22(K4R);

(SEQ ID NO: 70)
PEO24-GANSS-CNP22(K4R);

(SEQ ID NO: 134)
CNP22(K4R), N-term. dimer/disuccinimidyl
glutarate;

(SEQ ID NO: 135)
CNP22(K4R), N-term. dimer/Bis-PEO5;

(SEQ ID NO: 69)
PEO12-GANQQ-CNP22(K4R);

and (SEQ ID NO: 69)
PEO24-GANQQ-CNP22(K4R).
```

11. The CNP variant of claim 1, which has a total mass in the range from about 2.8 kDa to about 6.0 kDa.

12. The CNP variant of claim 1, which has at least a two-fold longer half-life than wild-type CNP-22 in an in vitro assay evaluating susceptibility to neutral endopeptidase (NEP) cleavage.

13. The CNP variant of claim 1, which in vitro stimulates the production of at least about 50% of the cGMP level produced under the same concentration of wild-type CNP-22.

14. A pharmaceutical composition comprising a CNP variant of claim 1, and a pharmaceutically acceptable excipient, carrier or diluent.

15. A method for treating a patient with a bone-related disorder comprising administering to said patient an amount of a CNP variant, which is not pegylated, of claim 1 or claim 10 wherein the bone-related disorder is selected from the group consisting of achondroplasia, hypochondroplasia, short stature associated with FGFR3 activity, dwarfism, thanatophoric dysplasia, and homozygous achondroplasia.

16. A method of increasing the size of a growth plate of a bone, longating a bone, increasing long bone growth, enhancing matrix production, increasing proliferation of chondrocytes or differentiation of chondrocytes comprising administering a CNP variant, which is not pegylated, of claim 1 or claim 10.

17. The CNP variant of claim 1, wherein for (z) the hydrophilic polymer is poly(ethylene glycol) (PEG) polymer or derivative thereof.

18. The CNP variant of claim 1 wherein for (x) the PEG polymer or derivative thereof and has a polymer number-average molecular weight in the range from about 0.6 kDa to about 1.5 kDa.

19. The CNP variant of claim 18, wherein the PEG polymer or derivative thereof is monodispersed.

20. The CNP variant of claim 1 where the amino acid sequences of (x) and (z), when (z) is an amino acid sequence, are 1 to 20 amino acids.

21. The variant of claim 20 where (x) does not comprise two consecutive basic amino acids at the positions immediately preceding the position corresponding to $Gly_1$.

22. The variant of claim 20 where the N-terminus of (x) ends in Gly.

23. The CNP variant of claim 1 where (z) is absent.

24. A variant of C-type natriuretic peptide (CNP) having a total mass in the range from about 2.6 kDa to about 7.0 kDa, which comprises:
 (a) a hydrophilic polymer, and
 (b) any one of ER-CNP22(K4R) (SEQ ID NO: 39), R-CNP22(K4R) (SEQ ID NO: 41), and GANQQ-CNP22(K4R) (SEQ ID NO: 69),
 wherein the hydrophilic polymer is attached to the peptide at the N-terminus, the C-terminus or an internal site, or a combination thereof.

* * * * *

UNITED STATES PATENT AND TRADEMARK OFFICE
CERTIFICATE OF CORRECTION

PATENT NO. : 8,377,884 B2  
APPLICATION NO. : 12/744079  
DATED : February 19, 2013  
INVENTOR(S) : Wendt et al.

Page 1 of 1

It is certified that error appears in the above-identified patent and that said Letters Patent is hereby corrected as shown below:

In the Claims

In Column 176, Line 29, in Claim 16, delete "longating" and insert -- elongating --, therefor.

In Column 176, Line 42, in Claim 19, delete "TheCNP" and insert -- The CNP --, therefor.

In Column 176, Line 48, in Claim 21, delete "The variant of claim 20" and insert -- The CNP variant of claim 20 --, therefor.

In Column 176, Line 51, in Claim 22, delete "The variant of claim 20" and insert -- The CNP variant of claim 20 --, therefor.

Signed and Sealed this  
Twenty-third Day of December, 2014

Michelle K. Lee  
*Deputy Director of the United States Patent and Trademark Office*